US012758284B2

(12) United States Patent
Dean et al.

(10) Patent No.: US 12,758,284 B2
(45) Date of Patent: Oct. 13, 2026

(54) METHODS, DEVICES, AND MANUFACTURE OF THE DEVICES FOR MUSCULOSKELETAL RECONSTRUCTIVE SURGERY

(71) Applicants: OHIO STATE INNOVATION FOUNDATION, Columbus, OH (US); THE UNIVERSITY OF TOLEDO, Toledo, OH (US)

(72) Inventors: Howard David Dean, Columbus, OH (US); Mohammad H Elahinia, Sylvania, OH (US); Christoph Haberland, Bochum (DE); Michael J. Miller, Columbus, OH (US); Alok Sutradhar, Dublin, OH (US); Narges Shayesteh Moghaddam, Toledo, OH (US); Jason M. Walker, Columbus, OH (US); Roman Skoracki, Columbus, OH (US)

(73) Assignees: OHIO STATE INNOVATION FOUNDATION, Columbus, OH (US); THE UNIVERSITY OF TOLEDO, Toledo, OH (US)

( * ) Notice: Subject to any disclaimer, the term of this patent is extended or adjusted under 35 U.S.C. 154(b) by 44 days.

(21) Appl. No.: 18/943,388

(22) Filed: Nov. 11, 2024

(65) Prior Publication Data

US 2025/0302512 A1 Oct. 2, 2025

Related U.S. Application Data

(63) Continuation of application No. 18/098,272, filed on Jan. 18, 2023, now Pat. No. 12,137,952, which is a (Continued)

(51) Int. Cl.
*A61B 34/10* (2016.01)
*A61B 17/80* (2006.01)

(Continued)

(52) U.S. Cl.
CPC .......... *A61B 17/8071* (2013.01); *A61B 34/10* (2016.02); *A61F 2/2803* (2013.01);

(Continued)

(58) Field of Classification Search
CPC ........ A61B 2034/104; A61B 2034/105; A61B 2034/108; A61B 34/10; A61B 17/8071;

(Continued)

(56) References Cited

U.S. PATENT DOCUMENTS 5,380,328 A 1/1995 Morgan
5,549,680 A 8/1996 Gordon (Continued)

FOREIGN PATENT DOCUMENTS

WO WO2000/059409 A1 10/2000
WO WO2014/085809 A1 6/2014

OTHER PUBLICATIONS

Abbas, "Reconstruction skeleton for the lower human jaw using CAD/CAM/CAE," Journal of King Saud University—Engineering Sciences, 2012, 24:159-64.

(Continued)

*Primary Examiner* — Samuel S Hanna
(74) *Attorney, Agent, or Firm* — MICHAEL BEST & FRIEDRICH LLP

(57) ABSTRACT

A device used in conjunction with fixation hardware to provide a two-stage process to address the competing needs of immobilization and re-establishment of normal stress-strain trajectories in grafted bone. A method of determining a patient-specific stress/strain pattern that utilizes a model based on 3D CT data of the relevant structures and cross- (Continued)

sectional data of the three major chewing muscles. The forces on each of the chewing muscles are determined based on the model using predetermined bite forces such that a stiffness of cortical bone in the patient's mandible is determined. Based on the stiffness data, suitable implantation hardware can be designed for the patient by adjusting external topological and internal porous geometries that reduce the stiffness of biocompatible metals to thereby restore normal bite forces of the patient. A method of 3D printing nitinol to create a patient-specific device to facilitate the establishment of a normal stress-strain trajectory in grafted bone.

2 Claims, 36 Drawing Sheets

Related U.S. Application Data continuation of application No. 15/124,660, filed as application No. PCT/US2015/020043 on Mar. 11, 2015, now Pat. No. 11,628,001.

(60) Provisional application No. 62/110,281, filed on Jan. 30, 2015, provisional application No. 61/951,028, filed on Mar. 11, 2014.

(51) Int. Cl.
*A61F 2/28* (2006.01)
*A61F 2/30* (2006.01)
*A61B 17/00* (2006.01)

(52) U.S. Cl.
CPC .................... *A61F 2/30942* (2013.01); *A61B 2017/00004* (2013.01); *A61B 2034/104* (2016.02); *A61B 2034/105* (2016.02); *A61B 2034/108* (2016.02); *A61F 2002/30014* (2013.01); *A61F 2002/30303* (2013.01); *A61F 2002/3092* (2013.01); *A61F 2002/30962* (2013.01)

(58) Field of Classification Search
CPC ................ A61F 2/30942; A61F 2/2803; A61F 2002/30014; A61F 2002/3092; A61F 2002/30303; A61F 2002/30962
See application file for complete search history.

(56) References Cited

U.S. PATENT DOCUMENTS

| | | | |
|---|---|---|---|
| 2002/0123750 | A1 | 9/2002 | Eisermann et al. |
| 2002/0143336 | A1 | 10/2002 | Hearn |
| 2003/0074081 | A1 | 4/2003 | Ayers |
| 2006/0041262 | A1 | 2/2006 | Calvert et al. |
| 2008/0060725 | A1 | 3/2008 | Demetriou et al. |
| 2010/0215718 | A1 | 8/2010 | Swords et al. |
| 2010/0268278 | A1 | 10/2010 | Foley et al. |
| 2010/0305569 | A1 | 12/2010 | Leuenberger et al. |
| 2011/0014081 | A1 | 1/2011 | Jones et al. |
| 2011/0076316 | A1 | 3/2011 | Sivananthan et al. |
| 2011/0190904 | A1 | 8/2011 | Lechmann et al. |
| 2012/0191139 | A1 | 7/2012 | Stevens et al. |
| 2012/0289965 | A1 | 11/2012 | Gelaude et al. |
| 2013/0164707 | A1 | 6/2013 | Ali |
| 2014/0003695 | A1 | 1/2014 | Dean et al. |
| 2014/0147814 | A1 | 5/2014 | Collins et al. |
| 2015/0112443 | A1* | 4/2015 | Gelaude .............. A61F 2/30734 700/98 |
| 2017/0014169 | A1 | 1/2017 | Howard et al. |

OTHER PUBLICATIONS

Abukawa et al., "Reconstruction of mandibular defects with autologous tissue-engineered bone," Journal of oral and maxillofacial surgery, 2004, 62(5):601-606.
Abu-Serriah et al., "Contour and vol. assessment of reparing mandibular osteoperiosteal continuity defects in sheep using recombinant human osteogenic protein 1," Journal of Cranio-Maxillofacial Surgery, 2006, 34:162-7.
Abu-Serriah et al., "Mechanical evaluation of mandibular defects reconstructed using osteogenic protein-1 (rhOP-1) in a sheep model: a critical analysis," International journal of oral and maxillofacial surgery, 2005, 34:287-93.
Andani et al., "An Investigation of Effective Process Parameters on Phase Transformation Temperature of Nitinol Manufactured by Selective Laser Melting," ASME Conference on Smart Materials, Adaptive Structures and Intelligent Systems (SMASIS), 2014. (Abstract).
Andani et al., "Design, modeling and experimental evaluation of a minimally invasive cage for spinal fusion surgery utilizing superelastic Nitinol hinges," Journal of Intelligent Material Systems and Structures, 2014, p. 1045389X14541499.
Andani et al., "Metals for bone implants. Part 1. Powder metallurgy and implant rendering," Acta Biomaterialia, 2014.
Baggi et al., "The influence of implant diameter and length on stress distribution of osseointegrated implants related to crestal bone geometry: a three-dimensional finite element analysis," The Journal of Prosthetic Dentistry, 2008, 100:422-31.
Bahr et al., "Use of the "double barrel" free vascularized fibula in mandibular reconstruction," Journal of oral and maxillofacial surgery, 1998, 56(1):38-44.
Bahraminasab et al., "Aseptic loosening femoral components—A review of current and future trends in materials used," Materials & Design 2012, 42:459-70.
Barone et al., "Temporalis muscle resuspension using titanium miniplates and screws: technical note," Neurosurgery, 2001, 48:450-1.
Bidabadi et al., "Thermophoresis effect on volatile particle concentration in micro-organic dust flame," Powder Technology, 2012, 217:69-76.
Blackwell et al., "The bridging lateral mandibular reconstruction plate revisited," Archives of Otolaryngology—Head & Neck Surgery, 1999, 125:988.
Bormann et al., "Tailoring selective laser melting process parameters for NiTi implants," Journal of materials engineering and performance, 2012, 21(12):2519-2524.
Bornapour et al., "Biocompatibility and biodegradability of Mg—Sr alloys: the formation of Sr-substituted hydroxyapatite," Acta Biomaterialia, 2012.
Boyd et al., "Case Report Removal of Exposed Titanium Reconstruction Plate After Mandibular Reconstruction With a Free Fibula Osteocutaneous Flap With Large Surgical Pin Cutters: A Case Report and Literature Review," Eplasty, 2012.
Brar et al., "A study of biodegradable Mg—3Sc—3Y alloy and the effect of self-passivation on in-vitro degradation," Acta Biomaterialia, 2012.
Brar et al., "Investigation of the mechanical and degratation properties of Mg—Sr and Mg—Zn—Sr alloys for use as potential biodegradable implant materials," Journal of the mechanical behavior of biomedical materials, 2012, 7:87-95.
Bravo et al., "NiTi superelastic orthodontic archwires with polyamide coating," Journal of Materials Science: Materials in Medicine, 2014, 25(2):555-560.
Cao et al., "Ca—Mg—Zn bulk mettalic glasses as bioresorbable metals," Acta Biomaterialia, 2012, 8(6):2375-2383.
Chacon et al., "Using resorbable screws for fixation of cortical onlay bone grafts: An in vivo study in rabbits," Journal of oral and maxillofacial surgery, 2004, 62(11):1396-1402.
Chang et al., "Dental implant outcome after primary implantation into double-barreled fibula osteoseptocutaneous free flap-reconstructed mandible," Plast Reconstr Surg, 2011, 128(6):1220-8.
Cheal et al., "Role of Loads and Prosthesis Material Properties on the Mechanics of the Proximal Femur After Total Hip Arthroplasty," Journal of Orthopaedic Research 10(3):405 (1992).

(56) References Cited

OTHER PUBLICATIONS

Cho et al., "Biocompatibility and strength retention of biodegradable Mg—Ca—Zn alloy bone implants," J Biomed Mater Res B Appl Biomater, 2013, 101(2):201-12.
Choukas et al., "The reattachment of the masseter muscle to the mandible," Oral Surgery, Orakl Medicine, Oral Pathology, 1968, 25:889-95.
Clare et al., "Selective laser melting of high aspect ratio 3D nickel-titanium structures two way trained for MEMS applications," International Journal of Mechanics and Materials in Design, 4(2):181-187.
Cohen et al., "Mandibular reconstruction using stereo; ithographic 3-dimensional printing modeling technology," Oral Surgery, Oral Medicine, Oral Pathology, Oral Radiology and Endodontology, 2009, 108:661-6.
Das et al., "Physical aspects of process control in selective laser sintering of metals," Advanced Engineering Materials 5.10, 2003, pp. 701-711.
Dean et al., "Multiple Initiators and Dyes for continuos Digital Light Processing (cDLP) Additive Manufacture of Resorbable Bone Tissue Engineering Scaffolfs," Virtual and Physical Prototyping, 2014, DOI: 10.1080/17452759.2013.873337. (Abstract).
Deberg et al., "An SMA Passive Ankle Foot Orthosis: Design, Modeling, and Experimental Evaluation," Smart Materials Research, 2014.
Derand et al., "Imaging, Virtual Planning, Design, and Production of Patient-Specific Implants and Clinical Validation in Craniomaxillofacial Surgery," Cranialmaxillofacial Trauma and Reconstruction, 2012, 5: 137.
Dinh et al., "Reconstruction of osteomylitis defects," Seminars in plastic surgery, 2009.
Duerig et al., "An overview of nitinol medical applications," Materials Science and Engineering: A, 1999, 273:149-160.
Eggeler et al., "Structural and functional fatigue of NiTi shape memory alloys," Materials Science and Engineering: A, 2004, 378(1):24-33.
Elahinia et al., "Manufacturing and processing of NiTi implants: A review," Progress in Materials Science, 2012, 57:911-46.
Elahinia et al., "Shape Memory and Superelastic Alloys," High Temperature Materials and Mechanisms, 2014, p. 355.
Elsaghir et al., "Mini-open approach combined with percutaneous transarticular screw fixation for C1—C2 fusion," Neurosurg Rev., 2005, 28(1):59-63.
Fakourand et al., "Evaluation of the use of Self-reinforced Absorbable versus Metallic Plates and Screws in the Fractures of Symphysis and Parasymphysis Area," Life Science Journal—Acta Zhengzhou University Overseas Edition, 2012, 9(3):1538-1542.
Fujinaga et al., "Direct observation of keyhole behavior during pulse modulated high-power Nd: YAG laser irradiation," Journal of Physics D: Applied Physics, 2000, 33(5):492.
Ganesh et al., "Biomechanics of bone-fracture fixation by stiffness-graded plates in comparison with stainless-steel plates," Biomed Eng Online, 2005, 4:46.
Gerlach et al., "Bite forces in patients after treatment of mandibular angle fractures with miniplate osteosynthesis acording to Champy," International journal of oral and maxillofacial surgery 31, No. 4, 2002, 345-348.
Goh et al., "Mandibular reconstruction in adults: a review," International journal of oral and maxillofacial surgery, 2008, 37:597-605.
Gregory et al., "Improving the mandibular reconstruction plate: technical innovation," Journal of the Royal College of Surgeons of Edinburgh, 2000, 45:120-1.
Greiner et al., High strength, low stiffness, porous NiTi with superelastic properties, Acta Biomaterialia, 2005, 1:705-16.
Gu et al., "In vitro and in vivo studies on a Mg—Sr binary alloy system developed as a new kind of biodegradable metal," Acta Biomaterialia, 2012, 8(6):2360-2374.
Guan et al., "Development and Evaluation of a Magnesium-Zinc-Strontium Alloy for Biomedical Applications-Alloy Processing, Microstructure, Mechanical Properties, and Biodegradation," Materials Science and Engineering: C, 2013.
Guo et al., "A plastic Ni-free Zr-based bulk mettalic glass with high specific strength and good corrosion properties in simulated body fluid," Materials Letters, 2012, 84:81-84.
Gusarov et al., "Heat transfer modeling and stability analysis of selective laser melting," Applied Surface Science, 2007, 254(4):975-979.
Haberland et al., "Additive Manufacturing Of Shape Memory Devices And Pseudoelastic Components," ASME 2013 Conference on Smart Materials, Adaptive Structures and Intelligent Systems, 2013. (Abstract).
Haberland et al., "On the development of high quality NiTi shape memory and pseudoelastic parts by additive manufacturing," Smart Materials and Structures, 2014.
Haberland et al., "On the Properties of NiTi Shape Memory Parts Produced by Selective Laser Melting," ASME 2012 Conference on Smart Materials, Adaptive Structures and Intelligent Systems, American Society of Mechanical Engineers, pp. 97-104. (Abstract).
Haberland et al., "Visions, Concepts And Strategies For Smart Nitinol Actuators And Complex Nitinol Structures Produced By Additive Manufacturing," ASME 2013 Conference on Smart Materials, Adaptive Structures and Intelligent Systems, 2013. (Abstract).
Haberland, "Additive Verarbeitung von NiTi-Formgedächtniswerkstoffen mittels Selective-Laser-Melting," 2012. (English Abstract).
Hayden et al., "Reconstruction of the segmental mandibular defect: current state of the art," Curr Opin Otolaryngol Head Neck Surg, 2012, 20:231-236.
He et al., "Double-barrel fibula vascularized free flap with dental rehabilitation for madibular reconstruction," Journal of Oral and Maxillofacial Surgery, 2011, 69(10):2663-2669.
Henderson et al., "Magnesium alloys as a biomaterial for degradable cranofacial screws," Acta Biomater, 2013.
Hernandez et al., "Characteristics of porous nickel-titanium alloys for medical applications," Bio-Medical Materials and Engineering, 2002, 12:37-45.
Hidalgo et al., "Free-flap mandibular reconstruction: a 10 year follow-up study," Plastic and reconstructive surgery, 2002, 110:438-49.
Hohlweg-Majert et al., "Significance of osteoporosis in craniomaxillofacial surgery: A review of the literature," Osteoporosis international, 2006, 17(2):167-179.
Hort et al., "Magnesium alloys as implant materials—Principles of property design for Mg-RE alloys," Acta Biomaterialia, 2010, 6(5):1714-1725.
Huang et al., "Bio-corrosion study on zirconium-based bulk-metallic glasses," Intermetallics, 2009, 17(4):195-199.
Huang et al., Magnesium alloys as implant materials—Principles of property design for Mg-RE alloys, Acta biomaterialia, 2010, 6(5):1714-1725.
Huang et al., "Responses of bone-forming cells on pre-immersed Zr-based bulk metallic glasses: effects of composition and roughness," Acta Biomaterialia, 2011, 7(1):395-405.
Huiskes et al., "The relationship between stress shielding and bone resorption around total hip stems and the effects of flexible materials," Clinical orthopaedics and related research, 1992, 247:124-134.
Jacobs, "Rapid Prototyping & Manufacturing: Fundamentals of StereoLithography," Jan. 15, 1992, Journal of Manufacturing Systems, vol. 12, No. 5, pp. 430-433.
Johnson et al., "A Study on Factors Affecting the Degradation of Magnesium and a Magnesium-Yttrium Alloy for Biomedical Applications," PLOS One, 2013, 8(6):e65603.
Joshi et al., "Analysis of a femoral hip prosthesis designed to reduce stress shielding," Journal of Biomechanics, 2000, 33:1655-62.
Kavanagh et al., "Use of finite element analysis in presurgical planning: treatment of mandibular fractures," Irish Journal of Medical Science, 2008, 177:325-31.
Keller et al., "Endosseous implant and autogenous bone graft reconstruction of mandibular discontinuity: a 12-year longitudinal study of 31 patients," The International journal of oral & Maxillofacial implants, 1998, 13:767.

(56) References Cited

OTHER PUBLICATIONS

Kennady et al., "Histomorphometric evaluation of stress shielding in mandibular continuity defects treated with rigid fixation plates and bone grafts," International journal of oral and maxillofacial surgery, 1989, 18:170-4.
Khalil-Allafi et al., "Ni4Ti3-precipitation during aging of NiTi shape memory alloys and its influence on martensitic phase transformations," Acta Materialia, 2002, 50(17):4255-4274.
Kienapfel et al., "Implant fixation by bone ingrowth," The Journal of Arthroplasty, 1999, 14:355-68.
Korioth et al., "Three-dimensional finite element stress analysis of the dentate human mandible," American Journal of Physical Anthropology, 1992, 88(1):69-96.
Krishna et al., "Laser Processing of Net-Shape NiTi Shape Memory Alloy," Metallurgical and Materials Transactions A, 2007, 38(5):1096-1103.
Kunz, Proceedings of the 7th Annual Meeting of CAOS—International, 2007, 159-161.
Laschi et al., "Soft robotics: new perspectives for robot bodyware and control," Bionics and Biomimetics, 2014, 2:3.
Lee et al., "A modular endoprosthesis for reconstruction of the body, condyle and ascending ramus of the madible in an animal model," 2009.
Lee et al., "Concomitant reconstruction of madibular basal and alveolar bone with a free fibular flap," International journal of oral and maxillofacial surgery, 2004, 33(2):150-156.
Li et al., "In vitro investigation of novel Ni free Zr-based bulk metallic glasses as potential biomaterials," Materials Letters, 2012, 75:74-76.
Li et al., "Optimal design of an individual endoprosthesis for the reconstruction of extensive mandibular defects with finite element analysis," Journal of Cranio-Maxillofacial Surgery, 2014, (42) 73-78.
Liu et al., "Bio-activation of Ni-free Zr-based bulk metallic glass by surface modification," Intermetallics, 2010, 18(10):1978-1982.
Liu et al., "Corrosion behavior of Zr-based bulk metallic glasses in different artificial body fluids," Journal of alloys and compounds, 2006, 425(1):268-273.
Liu et al., "Effects of alloying elements (Mn, Co, Al, W, Sn. B. C and S) on biodegradability and in vitro biocompatibility of pure iron," Acta Biomaterialia, 2011, 7(3):1407-1420.
Liu et al., "In vitro investigation of Fe30Mn6Si shape memory alloy as potential biodegradable metallic material," Materials Letters, 2011, 65(3):540-543.
Lovald et al., "Biomechanical optimization of bone plates used in rigid fixation of mandibular fractures," J Oral Maxillofac Surg, 2009, 67(5):973-85.
Machado et al., "Medical applications of shape memory alloys," Brazilian Journal of Medical and Biological Research, 2003, 36(6):683-691.
Malukhin et al., "Material Characterization of NiTi Based Memory Alloys Fabricated by the Laser Direct Metal Deposistion Process," Journal of Manufacturing Science and Engineering, 2006, 128(3):691.
Mataee et al., "Adaptive ankle-foot orthoses based on superelasticity of shape memory alloys," Journal of Intelligent Material Systems and Structures, 2014, 1045389X14544145.
Maurer et al., "Computergestützte Kaukraftanalyse bei Patienten mit Unterkieferkontinuitätsresektionen," Mund-, Kiefer-und Gesichtschirurgie 10, No. 1, 2006: 37-41.
Meier et al., "Experimental studies on selective laser melting of metallic parts," Materialwissenschaft und Werkstofftechnik, 2008, 39(9):665-670.
Meier et al., "Selective Laser Melting of NiTi shape memory components," Innovative Developments in Design and Manufacturing: Advanced Research in Virtual and Rapid Prototyping, 2009, p. 233-238. (Abstract).
Meier et al., "Structural and Functional Properties of NiTi Shape Memory Alloys Produced by Selective Laser Melting," Innovative Developments in Design and Manufacturing: Advanced Research in Virtual and Rapid Prototyping, 2011, p. 291-296.
Mentz et al., "Powder metallurgical processing of NiTi shape memory alloys with elevated transformation temperatures," Materials Science and Engineering: A, 2008, 491(1):470-278.
Merkx et al., "Reconstruction of the mandible using preshaped 2.3 mm titanium plates, autogenous particulate cortico-cancellous bone grafts and platelet rich plasma: a report on eight patients," International journal of oral and maxillofacial surgery, 2004, 33(8):733-739.
Morgan et al., "Use of finite element analysis to assess bone strength, " BoneKEy-Osteovision 2:8 (2005).
Morgan, "Medical shape memory alloy applications—the market and its products," Materials Science and Engineering: A, 2004, 378(1):16-23.
Murthy et al., "Symptomatic plate removal in maxillofacial trauma: a review of 76 cases," Annals of plastic surgery, 2005, 55:603-7.
Nagasao et al., "A comparison of stresses in implantation for grafted and plate-and-screw madible reconstruction," Oral Surgery, Oral Medicine, Oral Pathology, Oral Radiology, and Endodontology, 2010, 109(3):346-356.
Nagasao et al., "Biomechanical evaluation of implant placement in the reconstructed mandible," The International journal of oral & maxillofacial implants, 2008, 24(6):999-1005.
Nagels et al., "Stress shielding and bone resorption in shoulder arthroplasty," Journal of Shoulder and Elbow Surgery, 2003, 12:35-9.
Ng et al., "Fabrication of magnesium using selective laser melting technique," Rapid Prototyping Journal, 2011, 17(6):479-490.
Rafferty et al., "Mandibular mechanics following osteotomy and appliance placement II: Bone strain on the body and condylar neck," J Oral Maxillofac Surg., 2006, 64(4):620-7.
Rahmanian et al., Load Bearing and Stiffness Tailored Nitinol Implants Produced by Additive Manufacturing in SPIE Smart Structures and Materials, 2014, SPIE, San Diego, California. (Abstract).
Rahmanian et al., "Modeling and Validation of Additively Manufactured Porous Nitinol Implants," ASME Conference on Smart Materials, Adaptive Structures and Intelligent Systems (SMASIS), 2014. (Abstract).
Ramakrishna et al., "Design of fracture fixation plate for necessary and sufficient bone stress shielding," JSME International Journal Series C, 2004, 47(4):1086-1094.
Reilly et al., "The elastic and ultimate properties of compact bone tissue," Journal of biomechanics, 8(6):393-405.
Rosalbino et al., "Bio-corrosion characterization of Mg—Zn—X (X= Ca, Mn, Si) alloys for biomedical applications," Journal of Materials Science: Materials in Medicine, 2010, 21(4):1091-1098.
Sayyidmousavi et al., "Investigation of stress shielding around the Stryker Omnifit and Exeter periprosthetic hip implants using an irreversible thermodynamic-based model," Journal of Biomedical Materials Research Part B: Applied Biomaterials, 2012, 100(5):1416-1424.
Schmitz et al., "The critical size defect as an experimental model for craniomandibulofacial nonunions," Clinical Orthopaedics and Related Research, 1986, 205:299-308. (Abstract).
Schrag et al., "Complete rehabilitation of the mandible following segmental resection," Journal of surgical oncology, 2006, 94(6):538-545.
Shaker et al., "Additive Manufacturing of Complex NiTi Shape Memory Devices And Pseudoelastic Components," ASME Conference on Smart Materials, Adaptive and Intelligent Systems, 2013. (Abstract).
Shayesteh-Moghaddam et al., Enhancement of Bone Implants by Substituting Nitinol for Titanium (Ti—6Al—4V): A Modeling Comparison,: ASME 2014 Conference on Smart Materials, Adaptive Structures and Intelligent Systems, 2014, Newport, Rhoad Island. (Abstract).
Shayesteh-Moghaddam et al., "Metallic Fixation of Mandibular Segmental Defects: Graft Immobilization and Orofacial Functional Maintenance," British Journal of Oral and Maxillofacial Surgery, 2016, 8 pages.
Shayesteh-Moghaddam et al., "Metals for Mandibular Implants, Part 2: Safety, Design, and Efficacy," Journal of Biomedical Materials Research Part B: Applied Biomaterials, 2016, 16 pages.

(56) References Cited

OTHER PUBLICATIONS

Shayesteh-Moghaddam et al., "Stiffness-Tuned Reconstructive Surgery Immobilization Hardware: Metallic Fixation for Mandibular Segmental Defects," Biofabrication, 2014.
Shetty et al., "A finite element analysis for a comparative evaluation of stress with two commonly used esthetic posts," European Journal of Dentistry, 2013, 7(4):419.
Shin et al., "Finite Element Analysis of Schwarz P Surface Pore Geometries for Tissue- Engineered Scaffolds," Mathematical Problems in Engineering, 2012.
Shishkovsky et al., "Nanofractal surface structure under laser sintering of titanium and nitinol for bone tissue engineering," Applied Surface Science, 2007, 254(4):1145-1149.
Shishkovsky, "Shape memory effect in porous vol. NiTi articles fabricated by selective laser sintering," Technical physics letters, 2005, 31(3):186-188.
Song et al., "Biodegradable behaviors of AZ31 magnesium alloy in simulated body fluid," Materials Science and Engineering: C, 2009. 29(3):1039-1045.
Sun et al., "Mandibular mechanics after osteotomy and distraction appliance placement I: Postoperative mobility of the osteotomy site," J Oral Maxillofac Surg., 2006, 64(4):610-9.
Sun et al., "Masticatory mechanics of a mandibular distraction osteogenesis site: interfragmentary micromovement," Bone 41, No. 2, 2007, 188-196.
Sutradhar et al., "Topological optimization for designing patient-specific large craniofacial segmental bone replacements," PNAS, 2010.
Tardieu, "Computer-Assisted Implanted Placement: Scan Template, SimPlant, SurgiGuide, and SAFE System," Int. J. Periodontics Restorative Dent., 2007, 27(2):141-149.
Tarnita et al., Properties and medical applications of shape memory alloys, Rom J Morphol Embryol., 2009, 50:15-21.
Tate et al., "Bite forces in patients treated for madibular angle fractures: implications for fixation recommendations," Journal of oral and maxillofacial surgery 52, No. 7, 1994, 734-736.
Thomas et al., "Masseter muscle reattachment after mandibular angle surgery," Aesthetic Journal, 2009, 29:473-6.
Tie et al., "Three-dimensional finite-element analysis investigating the biomechanical effects of human mandibular reconstruction with autogenous bone grafts," Journal of Cranio-maxillofacial Surgery, 2006, 34:290-8.
Tsuchiya et al., "Clinical factors associated with postoperative complications and the functional outcome in madibular reconstruction," Microsurgery, 2013.
Urban et al., "The Bone-Implant Interface of Femoral Stems with Non-Circumferential Porous Coating. A Study of Specimens Retrieved at Autopsy," The Journal of Bone & Joint Surgery, 1996, 78:1068-81.
Van Eijden et al., "Architecture of the human jaw-closing and jaw-opening muscles," The anatomical record, 1997, 248(3):464-474.
Van Essen et al., "Anatomically based modeling of the human skull and jaw," Cells Tissues Organs, 2005, 180(1):44-53.
Van Rietbergen et al., "The mechanism of bone remodeling and resorption around press-fitted THA stems," Journal of Biomechanics, 1993, 26:369-82.
Vayvada et al., "Surgical management of ameloblasta in the mandible: segmental mandibulectomy and immediate reconstruction with free fibula or deep circumflex iliac artery flap (evaluation of the long-term esthetic and functional results)", Journal of oral and maxillofacial surgery, 2006, 64(10)1532-1539.
Velikokhatnyi et al., "First principles studies on alloying and simplified thermodynamic aqueous chemical stability of calcium-, zinc-, aluminum-, yttrium-and iron-doped magnesium alloys," Acta Biomaterialia, 2010, 6(5):1698-1704.
Vojtech et al., "Mechanical and corrosion properties of newly development biodegradable Zn-based alloys for bone fixation," Acta biomaterialia, 2011, 7(9):3515-3522.
Walker et al., "Additive Manufacturing of Nitinol Shape Memory Alloys to Overcome Challenges in Conventional Nitinol Fabrication," Proceedings of the International Mechanical Engineering Congress Exposition IMECE2014, 2014.
Walker et al., Additive Manufacturing towards the Realization of Porous and Stiffness-tailored NiTi Implants, 2014, University of Toledo.
Wang et al., "Enhanced mechanical properties and corrosion resistance of a Mg—Zn—Ca bulk metallic glass composite by Fe particle addition," Materials Letters, 2012.
Wang et al., "In vivo degradation behavior of Ca-deficient hydroxyapatite coated Mg—Zn—Ca alloy for bone implant application," Colloids and Surfaces D: Biointerfaces, 2011, 88(1):254-259.
Wang et al., "Mechanical properties of porous titanium with different distributions of pore size," Transactions of Nonferrous Metals Society of China, 2013, 23(8):2317-22.
Warnke et al., "Growth and transplantation of a custom vascularised bone graft in a man," The Lancet, 2004, 364:766-70.
Weinert et al., "Machining of NiTi based shape memory alloys," Materials Science and Engineering: A, 2004, 378(1):180-184.
Wen et al., "Processing and mechanical properties autogenous titanium implant materials," Journal of Materials Science: Materials in Medicine, 2002, 13:397-401.
Witte et al., "Biodegradable magnesium-hydroxyapatite metal matrix composites," Biomaterials, 2007, 28(13):2163-2174.
Wong et al., "Biomechanics of mandibular reconstruction: a review," International journal of oral and maxillofacial surgery, 2010, 39:313-9.
Wong et al., "The modular endoprosthesis for mandibular body replacement. Part 2: Finite element analysis of endoprosthesis reconstruction of the mandible," Journal of Cranio-Maxillofacial Surgery, 2012, 40(8):e487-497.
Wu et al., "A study on the machinability of a Ti49.6 Ni50.4 shape memory alloy," Materials Letters, 1999, 40(1):27-32.
Xu et al., "Controllable degradation of biomedical magnesium by chromium and oxygen dual ion implantation," Materials Letters, 2011, 65(14):2171-2173.
Yang et al., "One-step shaping of NiTi biomaterial by selective laser melting," Photonics Asia, 2007.
Yarlagadda et al., "Recent advances and current development in tissue scaffolding," Bio-Medical Materials and Engineering, 2005, 15:159-77. (Abstract).
Yerit et al., "Fixation of mandibular fractures with biodegradable plates and screws," Oral Surgery, Oral Medicine, Oral Pathology, Oral Radiology, and Endodontology, 2002, 94:294-300.
Zhang et al., "Biocorrosion properties of as-extruded Mg—Nd—Zn—Zr alloy compared with commercial AZ31 and WE43 alloys," Materials Letters, 2012, 66(1):209-211.
Zhang et al., "Effects of extrusion and heat treatment on the mechanical properties and biocorrosion behaviors of a Mg—Nd—Zn—Zr alloy," Journal of the Mechanical Behavior of Biomedical Materials, 2012, 7:77-86.
Zhim et al., "Personalized implant for high tibial opening wedge: combination of solid freeform fabrication with combustion synthesis process," J. Biomater Appl., 2012, 27(3):323-32.
Zineb, "Modeling and Simulation of Medical Devices Undergoing Complex Thermo-Mechanical Loadings," The International Conference on Shape Memory and Superelastic Technologies (SMST), AMS, 2013.
Zong et al., "Comparison of biodegradable behaviors of AZ31 and Mg—Nd—Zn—Zr alloys in Hank's physiological solution," Materials Science and Engineering: B, 2012, 177(5):395-401.
International Search Report and Written Opinion for Application No. PCT/US2015/020043 dated Jul. 28, 2015.
European Patent Office Partial Supplementary Search Report for Application No. 15761675.6 dated Jan. 31, 2018 (15 pages).
European Patent Office Extended Search Report for Application No. 15761675.6 dated May 23, 2018 (14 pages).
European Patent Office Action for Application No. 15761675.6 dated Dec. 18, 2019 (5 pages).

* cited by examiner (a) (b) (c)

(a) (b) (c)

(A) (B)

(a) P = 250 W, $v_s$ = 1.25 m/s (b) P = 100 W, $v_s$ = 0.5 m/s

| | Powder | SLM-NiTi |
|---|---|---|
| $M_s$ | 59 C | 62 C |
| $M_f$ | 26 C | 35 C |
| $A_s$ | 55 C | 65 C |
| $A_f$ | 93 C | 92 C |
| $M_{peak}$ | 34 C | 50 C |
| $A_{peak}$ | 66 C | 82 C |

| Material | Elastic Modulus (GPa) |
|---|---|
| 316 Stainless Steel | 193 |
| Titanium (Ti-6Al-4V) | 116 |
| SLM-NiTi | 38.5 |
| SLM-NiTi: 32% Porosity | 16.3 |
| SLM-NiTi: 45% Porosity | 13.7 |
| SLM-NiTi: 58% Porosity | 9.9 |
| Bone (Reilly & Burstein, 1975) | 11-18 |

METHODS, DEVICES, AND MANUFACTURE OF THE DEVICES FOR MUSCULOSKELETAL RECONSTRUCTIVE SURGERY

CROSS-REFERENCE TO RELATED APPLICATIONS

This application is a continuation of U.S. patent application Ser. No. 18/098,272, filed on Jan. 18, 2023, which is a continuation of U.S. patent application Ser. No. 15/124,660, filed on Sep. 8, 2016, now issued as U.S. Pat. No. 11,628, 001 on Apr. 18, 2023, which is the U.S. national phase of PCT/US2015/020043, filed on Mar. 11, 2015, which is a non-provisional of and claims priority to U.S. Provisional Application No. 61/951,028, filed on Mar. 11, 2014 and U.S. Provisional Application No. 62/110,281, filed on Jan. 30, 2015. The contents of all of these applications are incorporated herein by reference.

BACKGROUND OF THE INVENTION

Cancer, trauma, osteopenia, joint degradation, or reconstructive surgery can result in resection of bone. As a result, there is a significant and growing need for developing new sources of transplanted bone and bone substitute materials as well as developing surgical plans for how those materials will interact with artificial joints and fixation strategies that are aimed at restoring or creating normal musculoskeletal function. Currently, the standard of care for an area of bone deficit is to graft the patient's own bone to a defect site. However, surgeons must be very careful in their use of grafted bone due to a limited supply from the patient's own body. Not only is the supply very limited, but also, removal from a patient can result in tissue die-back as well as pain at the harvest site.

Current standards of care for musculoskeletal reconstructive surgery commonly involve utilization of an implant that may also include bone grafts and a combination of metal, plastic (polymeric), or ceramic materials to restore function and/or normal appearance. Traditional, off-the-shelf hip, knee, spine, and cranial implants and fixation hardware are often successful at immediately restoring ambulatory, protective, or other critical functions such as speech and chewing. Once the reconstructed bones have healed, the localized stiffness of current fixation and joint replacement hardware results in stress shielding and stress concentrations that over time can break or loosen these devices or damage the surrounding bone. As a result, these traditional implants can fail leading to pain. Revision surgery is often necessary.

The goals of reconstructive skeletal surgery are initially for the reconstructed bone to heal and then to remodel both its external geometry and internal structure in response to mechanical forces. The normal biological process of bone remodeling results in a strengthening of bone in response to its loading. Bone develops and maintains strength during remodeling by modifying calcified tissue mass and geometric properties in response to the new demands placed on the bone by the loading conditions. Bone remodeling is a continuous process that balances new bone formation and selective resorption. These are complementary processes that work together to optimize load bearing function. In response to a variation in local mechanical stimulus, bone forming cells (osteoblasts) and/or bone resorbing cells (osteoclasts) are activated to affect bone turnover rate, density, and/or geometry.

Under a new loading regimen, such as that which might be imposed after a reconstruction surgery, the bone remodeling process will continue with highly active bone formation and remodeling rates until stress and strain levels stabilize.

Traditional implants often include metallic components that are much stiffer than the bones to which they are attached. That stiffness differential can alter the normal distribution of forces in the anatomy (e.g., bone, joints, ligaments, tendons, etc.) that the implant device is attached to. Traditional implants may shield parts of the surrounding or fixated bones from load and concentrate forces in other parts of the surrounding anatomy (e.g., at the device's attachment site). If the stress-shielding reduces the load previously seen in areas fixated by or around the implant, those areas will not remodel and therefore will not regain their strength or may undergo subsequent resorption due to lack of loading. That will lead to the total amount and density of bone tissue decreasing (osteopenia and/or osteoporosis). The bone will become anatomically smaller (via external remodeling) and/or more porous (via internal remodeling) both of which will make it weaker. Additionally, if stress is concentrated in areas that have not previously been exposed to high loads there can be damage to the bone that results in fracture. This occurs when traditional implants continuously transfer a load too efficiently to areas that previously carried a different amount of strain (e.g., less strain) or could carry that strain if it were distributed over a larger area. Resorption resulting from post-implantation stress-shielding and/or the damage resulting from abnormal stress concentration can contribute to the breaking, failure, or loosening of the implant or the failure of grafted bone.

The geometry of traditional implants made from plastic, ceramic, and/or metal can change the distribution of stress that normally occurs in the fixated or replaced anatomical area (e.g., surrounding anatomy such as bone, femur, etc.). For example, traditional hip implant devices concentrate stress in distal regions of the diaphysis and transduce little stress to the proximal region of the femur where it is seen under normal conditions. This results in increasing the density of bone in the distal region which reduces axial stem displacement. It not only decreases the wedge effect of the stem within the diaphysis, but it also reduces the load on proximal regions. Therefore, bone in the proximal region of the femur starts to resorb and lose density.

Traditional bone implants can have very different material properties from the surrounding anatomy (i.e., bone) to which they are attached, which can result in a mismatch of modulus between the implant and the surrounding anatomy. The mismatched modulus can prevent the efficient transfer of load from the surrounding skeleton to the implant and vice-versa, this causes stress/strain concentrations and/or stress shielding that can prevent desirable stress-strain trajectories at previously seen levels (e.g., prior to the implantation of the implant). In the case of the femur this had been in the outer cortical surface, especially in the diaphysis (shaft) of the femur. This misoriented strain can result in pain in, and/or damage to, the surrounding anatomy. Accordingly, even with optimized implant geometries, the traditional medical devices' material stiffness mismatch with the surrounding anatomy can cause failure due to unhelpful stress shielding and/or stress concentrations. A high stiffness ratio can lead to high shear stress at the host/implant interface and reduced displacement in the surrounding bone.

Thus, at a boundary between the traditional implant and the surrounding anatomy, the change in physical properties (e.g., modulus) is sudden. This can cause loss of density over time in the surrounding anatomy that can lead to weakening of the surrounding anatomy and/or damage to the surrounding anatomy.

For example, FIGS. 1A and 1B show a comparative stress analysis of a natural hip joint (FIG. 1A) versus a conventional hip joint implant device (FIG. 1B). The natural hip joint shown in FIG. 1A shows that there is a higher strain medially just below the head and neck of the femur. However, as shown in FIG. 1B, after the conventional hip joint implant device has been implanted, strain is concentrated laterally near the greater trochanter and distally within the marrow cavity of the femur. This change in stress regions can lead to pain, change, and/or damage to the surrounding anatomy. The change and/or damage to the surrounding anatomy can occur over time. For example, over time, the conventional hip joint implant device can cause the density of the surrounding bone to change. FIG. 1C shows the bone density surrounding the conventional hip joint implant device (also shown in FIG. 1B) via an X-ray. FIG. 1D shows a bone density surrounding the conventional hip joint implant device (also shown in FIGS. 1B and 1C) via an X-ray after 10 years from the X-ray shown in FIG. 1C was taken. FIG. 1D shows that the bone density and cortical thickness increased in the distal marrow cavity in the femur, but there was a significant loss in bone density in the superomedial region of the femur. That is, FIGS. 1C and 1D clearly show that the bone density at the region surrounding the conventional hip joint implant device has weakened over time.

Additionally, grafted bone may be at risk. In many if not most cases, bone grafts do not have the same distribution of cortical bone that previously occupied the space where they are grafted. The transplanted bone is less likely to remodel to have the previously seen distribution of cortical bone if it is not under the same loading regime. Although the grafted bone's form may resemble the bone previously occupying the space, the grafted bone may fail in areas of stress concentration or resorb in areas of stress shielding caused by adjacent, metallic segmental gap, joint replacement, and/or osteotomy fixation devices.

Mandibular segmental defects present a specific example of segmental bone defect which is defined as a complete loss of bone in a portion of the mandible resulting in a gap. This gap is considered a "critical size" defect if it cannot be healed without an interventional procedure (Schmitz, J. P., et al., "*The critical size defect as an experimental model for craniomandibulofacial nonunions*," Clinical Orthopaedics and Related Research, 205: p. 299-308 (1986)). These defects may result from bone loss associated following tumor resection, trauma, infection, or radiation-induced tissue damage associated with cancer treatment (osteoradionecrosis) (Abukawa, H., et al., "*Reconstruction of mandibular defects with autologous tissue-engineered bone*," Journal of Oral and Maxillofacial Surgery, 62 (5): p. 601-606 (2004); Shayesteh Moghaddam, N., et al., "*Metals for Mandibular Implants, Part 2: Safety, Design, and Efficacy*," (in revision)).

Mandibular segmental defects may require grafting and metallic hardware devices to provide bone immobilization following reconstructive surgery, joint or dental prosthetic functional restoration, and the repair of large gaps using grafted bone or bone substitutes. Mandibular reconstruction can restore the mandible's function, normal appearance of a patient's face and jaw, mastication, speech, swallowing, and breathing (Schrag, C., et al., "*Complete rehabilitation of the mandible following segmental resection*," Journal of Surgical Oncology, 94 (6): p. 538-545 (2006)). Traditional clinical methods for mandibular reconstruction rely on using a traditional implant device for replacing the missing mandibular section with a combination of bone tissue (e.g., bone graft) and metal implants with screws for fixing the bone tissue in place. The most reliable means of restoring large mandibular segmental defects is the use of a vascularized bone transfer, usually harvested from the fibula or iliac crest (Shayesteh Moghaddam, N., et al., "*Metals for Mandibular Implants, Part 2: Safety, Design, and Efficacy*," (in revision); Dinh, P., et al., "*Reconstruction of osteomyelitis defects. in Seminars in plastic surgery*," Thieme Medical Publishers (2009)). Typically, one or more surgical grade Ti-6Al-4V fixation hardware devices are used to immobilize the graft (Shayesteh Moghaddam, N., et al., "*Enhancement of Bone Implants by Substituting Nitonol for Titanium (TI-6AL-4V): A Modeling Comparison," ASME 2014 Conference on Smart Materials, Adaptive Structures and Intelligent Systems*, Newport, Rhode Island (2014); Mataee, M. G., et al., "*Adaptive ankle-foot orthoses based on superelasticity of shape memory alloys*," Journal of Intelligent Material Systems and Structures, p. 1045389X14544145 (2014)). Because this hardware is often left in place after the bone has healed in place, it may subsequently cause stress shielding due to its high stiffness compared to the surrounding host bone. This may result in resorption of the shielded bone (Rahmanian, R., et al., "*Load bearing and stiffness tailored NiTi implants produced by additive manufacturing: a simulation study*," The International Society for Optical Engineering, San Diego, California (2014)).

Segmental defects of the mandible can occur in different lengths. Smaller defects (e.g., <6 cm) with healthy adjacent soft tissues can often be restored using a bone graft harvested from the iliac crest. A large amount of bone can be harvested from the iliac crest with minimal morbidity. Iliac crest grafts can provide sufficient bone to allow dental restoration using osteointegrated implants (Dinh, P., et al., "*Reconstruction of osteomyelitis defects. in Seminars in plastic surgery*," Thieme Medical Publishers (2009)). Larger defects with poor quality soft tissue require a vascularized bone graft. In this procedure the bone is transferred with a blood supply. It most often requires microvascular surgery to connect the blood vessels that supply the bone (i.e., a vascular pedicle) to blood vessels near the defect. The fibula is a common site for the harvest of a vascularized bone graft. It provides a long bone segment, a reliable (i.e., easily found) vascular pedicle, large diameter vessels and its removal causes minimal donor site morbidity (Schrag, C., et al., "*Complete rehabilitation of the mandible following segmental resection*," Journal of Surgical Oncology, 94 (6): p. 538-545 (2006); Dinh, P., et al., "*Reconstruction of osteomyelitis defects. in Seminars in plastic surgery*," Thieme Medical Publishers (2009)). The fibula also permits cutting and folding the bone segments upon themselves to create a "double barrel" of bone that is stronger and has roughly double the height of a single fibular barrel (Bähr, W., et al., "*Use of the 'double barrel' free vascularized fibula in mandibular reconstruction*," Journal of Oral and Maxillofacial Surgery, 56 (1): p. 38-44 (1998)). This procedure offers several advantages. It provides more vertical height resulting in an improved match to the normal mandible. The increased height improves the stability of dental implants (He, Y., et al., "*Double-barrel fibula vascularized free flap with dental rehabilitation for mandibular reconstruction*," Journal of Oral and Maxillofacial Surgery, 69 (10): p. 2663-2669 (2011)). The reduced height of a single-barrel fibular graft provides less depth for dental implant posts and results in more torque of the exposed portion of the dental implant post as it travels between the top of the graft and the occlusal plane (Lee, J., et al., "*Concomitant reconstruction of mandibular basal and alveolar bone with a free fibular flap*," International Journal of Oral and Maxillofacial Surgery, 33 (2): p. 150-156 (2004)). This unfilled gap may also cause a loss of facial contour (Bähr, W., et al., "*Use of the 'double barrel' free vascularized fibula in mandibular reconstruction*," Journal of Oral and Maxillofacial Surgery, 56 (1): p. 38-44 (1998); Bidabadi, M. et al., "*Thermophoresis effect on volatile particle concentration in micro-organic dust flame*," Powder Technology, 217: p. 69-76 (2012)).

It should be noted that the maximum width of a defect which can be filled by a double-barrel fibular graft taken from one calf is 10 cm. This limitation is due to the maximum fibular length which is 24 cm. This graft is usually removed with a vascular pedicle and a skin flap, and is then halved in length while preserving the blood supply. Next, the two segments are folded on top of each other (Bähr, W., et al., "*Use of the 'double barrel' free vascularized fibula in mandibular reconstruction*," Journal of Oral and Maxillofacial Surgery, 56 (1): p. 38-44 (1998)). The harvesting of a segment that is too long may increase the risk of donor site morbidity (He, Y., et al., "*Double-barrel fibula vascularized free flap with dental rehabilitation for mandibular reconstruction*," Journal of Oral and Maxillofacial Surgery, 69 (10): p. 2663-2669 (2011)) and/or knee or ankle joint instability.

Mandibular reconstruction with a double barrel fibular graft requires additional fixation devices to attach the upper barrel to the superior border of the remaining host mandible (Bähr, W., et al., "*Use of the 'double barrel' free vascularized fibula in mandibular reconstruction*," Journal of Oral and Maxillofacial Surgery, 56 (1): p. 38-44 (1998)). Often mini-plates are used to attach the upper barrel as they provide sufficient stability and reduce the surgical time and discomfort for patients (Lovald, S. T., et al., "*Biomechanical optimization of bone plates used in rigid fixation of mandibular fractures*," Journal of Oral and Maxillofacial Surgery, 67 (5): p. 973-985 (2009); Shayesteh Moghaddam, N., et al., "*Stiffness-Tuned Reconstructive Surgery Immobilization Hardware: Metallic Fixation for Mandibular Segmental Defects*," Biofabrication (under review)).

Healthy adult mandibles require certain properties that can withstand stress, strain, displacement, and reaction force distributions which are greatest during normal mastication. Mandibular segmental defect reconstructive surgeries typically use traditional hardware that has a stiffness mismatch of the immobilization hardware, graft, and the surrounding anatomy. This mismatch in stiffness between the traditional hardware and the graft/host bone can cause stress shielding at the implant-host tissue interface and stress concentration at fixation attachment sites. The abnormal stress-strain distribution over time may lead to host-graft discontinuity and, under masticatory loading may risk implant failure.

To successfully integrate a metallic fixation device (e.g., an implant), host cells are needed to colonize the fixation surface. When planktonic bacteria such as staphylococci adhere to the surface of metallic devices, the planktonic bacteria compete with the host cells for colonization. Bacterial gene expression changes and the organisms surround themselves with a matrix containing protein and mucopolysaccharides that form a protective covering called a biofilm that resists bacterial clearance by the host's natural defenses and antibiotics. It should be noted that bacteria can grow slowly or even remain dormant on metallic implants for several months to years and infection occurring suddenly once the numbers of bacteria reach sufficient levels to begin to invade the surrounding tissues. By adding porosity to implants, larger surface areas within and around the implant are vulnerable to bacterial colonization. It is important that the design of porous implants avoid deep porous spaces that are accessible to fluid, bacteria, or virii but not the immune system (i.e., well-vascularized adjacent tissue).

SUMMARY OF THE INVENTION

The methods and systems of the present invention provide for the design and fabrication of an implant that is restorative in the immediate and long term.

In addition, methods and systems are described herein for a precise analysis and matching of the geometric and mechanical stress/strain trajectories needed in the reconstruction of an anatomically and functionally correct musculoskeletal element. Patient-specific implants matching both the geometry (shape) and mechanical properties of the desired area of a patient's anatomy are then fabricated by additive manufacturing. The methods and systems of the present invention allow for the reproducible fabrication of patient-specific implants where the geometry and stiffness of the implant varies throughout the implant to allow for the closest possible fit with patient-specific normal anatomy (shape) and stress-strain trajectories (biomechanics) to facilitate creating or reconstructing normal function as a planned outcome of the intervention. The methods and systems of the present invention can be applied to bone as well as to numerous other organ systems in the body and to the development of patient specific surgical guides.

According to one embodiment, the present invention comprises a method of designing and fabricating a patient-specific implant involving the steps of first determining a stress and strain profile for an anatomic structure, where the anatomic structure is positioned in at least one organ or a portion of an organ of a patient. Then, a patient-specific implant for a segment of the anatomic structure is designed, where the stress and strain profile for the patient-specific implant matches the stress and strain profile for the anatomic structure from normal anatomy as well as the 3D geometry of that anatomic structure. The process of determining the stress/strain profile, matching it to the normal anatomic structure and matching the 3D geometric structure of the area where the implant is to be seated is referred to as designing the patient-specific implant. Finally, a patient-specific implant and/or surgical guide is fabricated. The organ system may be selected from the group consisting of the cardiovascular system, the lymphatic system, the digestive system, the endocrine system, the excretory system, the immune system, the musculoskeletal system, the nervous system, the urogenital system, integumentary, the respiratory system or any combination of the foregoing.

The patient-specific implant can incorporate autologous, allogeneic or alloplastic tissue, or be formed in-part or entirely from a bioabsorbable component. The bioabsorbable component may be fabricated using 3D printing (additive manufacturing).

In one embodiment, the patient—specific implant is formed from metal, which can be a magnesium or titanium alloy.

In another embodiment, the patient—specific implant or implant component can be a cured polymer, for example polypropylene fumarate).

In yet a third embodiment, the patient—specific implant or implant component can be a ceramic, e.g., hydroxyapatite (HA) or tricalcium phosphate (TCP).

The stress and strain profile for an anatomic structure can be developed by taking a 3D CT scan of the anatomic structure and then, using that data developing a finite element analysis (FEA) of the anatomic region of interest. Any anatomic structure may be identified and evaluated. In one embodiment, the anatomic structure is a bone such as a mandible or femur, but potentially any anatomic structure within the body may be analyzed.

The invention also encompasses patient-specific implants, patient-specific implant fixation devices, and patient-specific surgical guides either for transplanting, attaching or placing autologous, allogeneic, or alloplastic anatomical structures. The implants, fixation devices, or surgical guides are then fabricated according the methods of the present invention. The method also contemplates fabricating a patient-specific surgical guide comprising the steps of: (a) determining a stress and strain profile for an anatomic structure, wherein the anatomic structure is positioned in at least one organ of a patient; (b) designing a patient-specific implant for a segment of the anatomic structure, wherein the stress and strain profile for the patient-specific implant matches the stress and strain profile for the anatomic structure from normal anatomy; (c) forming a patient-specific surgical guide, wherein the patient-specific surgical guide matches the segment of the anatomic structure and comprises at least one cutting guide, positioning piece or drilling guide; and, (d) fabricating the patient-specific surgical guide.

In one embodiment, the invention provides a device (i.e., the "Bone Bandaid") used in conjunction with a fixation device to provide a two-stage process to address the competing needs of immobilization and re-establishment of normal stress-strain trajectories in grafted bone.

In another embodiment, the invention provides a method of 3D printing nitinol to create a patient-specific device to facilitate the establishment of a normal stress-strain trajectory in grafted bone.

In a further embodiment, the invention provides a method for reconstructing a mandible using the Bone Bandaid and releasable fixation hardware.

In another embodiment, the invention provides a method of determining a patient-specific stress/strain pattern that utilizes a model based on 3D CT data of the relevant structures and cross-sectional data of the three major chewing muscles. The forces on each of the chewing muscles are determined based on the model using predetermined bite forces such that a stiffness of cortical bone in the patient's mandible is determined. Based on the stiffness data, suitable implantation hardware can be designed for the patient by adjusting external topological and internal porous geometries that reduce the stiffness of biocompatible metals to thereby restore normal bite forces of the patient.

In yet another embodiment, the invention provides a method of determining a patient-specific stress/strain pattern in order to tune the material used in fixation hardware to match the stiffness of the cortical bone as closely as possible while also providing sufficient strength to allow bone healing (adequate fixation) following reconstructive surgery.

In still another embodiment, the invention provides a system and method for optimizing part orientation when manufacturing the part using 3D printing, e.g., selective laser melting techniques. The system utilizes a multi-objective approach to optimize orientation of complex metal parts using mathematical algorithms at different stages of the optimization. Initially, the part is decomposed into separate segments, and the orientation of each segment is optimized individually by taking into consideration accuracy, surface quality, support structures, anisotropy, heat management, and economy. After optimization of each segment, the segments are combined and then a second optimization occurs that considers heat management of the entire part and support structures considering the entire part. The resulting optimized orientation of the part is saved in memory and/or communicated to a 3D printing system for printing.

Other aspects of the invention will become apparent by consideration of the detailed description and accompanying drawings.

DETAILED DESCRIPTION

Figures 1A, 1B, 1C, 1D:
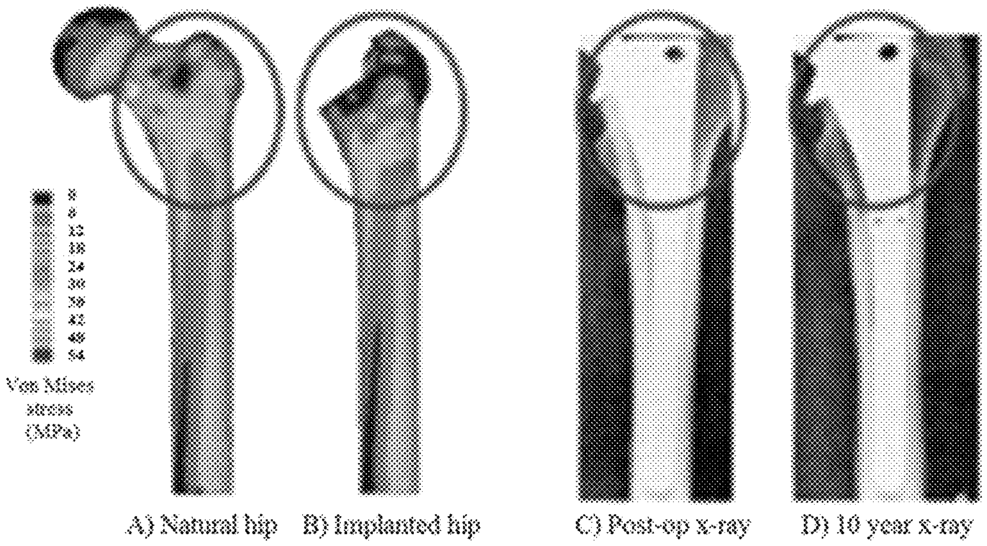
FIG. 1A shows a stress analysis of a natural hip joint.
FIG. 1B shows a stress analysis of a traditional hip joint implant device.
FIG. 1C shows the bone density surrounding the traditional hip joint implant device (also shown in FIG. 1B) via an X-ray.
FIG. 1D shows a bone density surrounding the traditional hip joint implant device (also shown in FIGS. 1B and 1C) via an X-ray after 10 years from the X-ray shown in FIG. 1C was taken.

Before any embodiments of the invention are explained in detail, it is to be understood that the invention is not limited in its application to the details of the configuration and arrangement of components set forth in the following description or illustrated in the accompanying drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processing units, such as a microprocessor and/or application specific integrated circuits ("ASICs"). As such, it should be noted that a plurality of hardware and software based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

Traditional, off-the-shelf hip, knee, spine, and cranial implants and fixation hardware are often successful at immediately restoring ambulatory, protective, or other critical functions such as speech and chewing. Once the reconstructed bones have healed, the localized stiffness of current fixation and joint replacement hardware results in stress shielding and stress concentrations that over time break or loosen these devices or damage the surrounding bone. Affected patients experience pain, and revision surgery is often necessary. Additive manufacturing (3D printing) of stiffness-matched, biocompatible metal implants would create an opportunity for patient-specific solutions to these problems. Three gap areas holding these advances back are (1) the absence of Computer Aided Design (CAD) software that accounts for patient-specific stress-strain trajectories, (2) a lack of 3D printable materials with tunable mechanical properties, and (3) technologies to fabricate devices that first stiffly immobilize and then become elastic and restorative following adequate bone healing.

There are three pressing problems that are based on the inventors' recent research breakthroughs. First, to address this knowledge gap we have extended our patient-specific implant CAD software to include material properties and biomechanical outcomes. Second, we have developed biocompatible nitinol alloys that can be 3D printed in high resolution powderbed devices. Finally, we have fabricated nitinol implants that have sufficient accuracy to create smooth host-implant mechanical property transitions and normal stress-strain trajectories in any part of the skeleton.

Preliminary studies have demonstrated that normal stress-strain trajectories can be predicted by querying two databases, one of normal anatomical shape, and another of normal in vivo mechanical performance, within the patient's own bone shape obtained from their 3D CT image. We have tested and propose to use these results for the design of external topological and internal porous geometries that reduce the stiffness of biocompatible metals. We have created nitinol fabrication strategies that we predict will accomplish these design goals via 3D printing. Finally, we have investigated the repair of mandibular segmental defects via standard autologous bone flap transfer methods. However, further studies are essential to successfully demonstrate restorative rather than high risk metallic mandibular fixation devices.

The specification describes aspects of the present invention(s) with direct applicability to the mandible, as the inventors have focused their work on the mandible. However, it is noted that the present invention is also applicable to other musculoskeletal devices that are implanted during reconstructive surgery and thus, the claims are not solely limited to the mandible unless otherwise indicated.

An implant as used herein is a medical device or tissue that replaces a missing biological structure, supports a damaged biological structure, or enhances an existing biological structure. By way of non-limiting examples, an implant includes bone segment replacement, joint replacements, and fixation devices.

"Stiffness matching" as used herein means: the matching of the modulus of elasticity between implant and metallic implant. Stiffness matching decreases stress shielding and may stimulate desired bone remodeling.

To describe various solutions to the problems noted above, this patent specification is divided into five sections. The first section discusses the biomechanical behavior of a normal mandible and the effects of stress/strain on the mandible that has been surgically reconstructed. Additionally, the first section demonstrates how to predict what material properties are needed for graft, fixation hardware, etc. at any point in the mandible based on its normal, full force (not 60% reduced as is usually seen following reconstruction with Ti-6Al-4V hardware).

The second section focuses on the use of alternative materials for fixation hardware used in reconstructions surgery to address the stiffness mismatch caused by existing fixation hardware materials. In particular, this section stiffness matches fixation hardware with porous NiTi. The matching may be a compromise between sufficient strength to fixate following reconstructive surgery and not to stress shield or stress concentrate following the healing period. Therefore, the hardware is not optimized, like the Bone Bandaid for both functions (i.e., fixation and promoting restoration of normal stress-strain trajectories).

Section three reveals a novel device used in conjunction with fixation hardware to provide a two-stage process to address the competing needs of immobilization and re-establishment of normal stress-strain trajectories in grafted bone. Section four demonstrates that nitinol can be 3D printed to create patient-specific metallic implants and fixation devices to take advantage of nitinol's unique properties. Finally, section five discusses a solution to ensuring proper part orientation during 3D printing.

Section I: Biomechanical Behavior of a Complete, Normal Mandible

As noted above, mandibular reconstruction may be necessary due to segmental defects caused by surgical resection of congenital deformities, tumor resection, other iatrogenic bone osteotomy, trauma damage, infection, or radiation-induced tissue damage associated with cancer treatment. The current standard of care procedures for mandibular reconstruction use Ti-6Al-4V (Surgical Grade 5 titanium) hardware along with a single or double fibular barrel graft. The inventors, through their studies, discussed below, have found that the current Ti-6Al-4V hardware provides a significant stiffness mismatch with the immobilization hardware, the graft, and the remaining host anatomy. As a result of this significant stiffness mismatch, the hardware may subsequently cause stress shielding due to its high stiffness compared to the surrounding host bone. This may result in resorption of the shielded bone.

Figure 2:
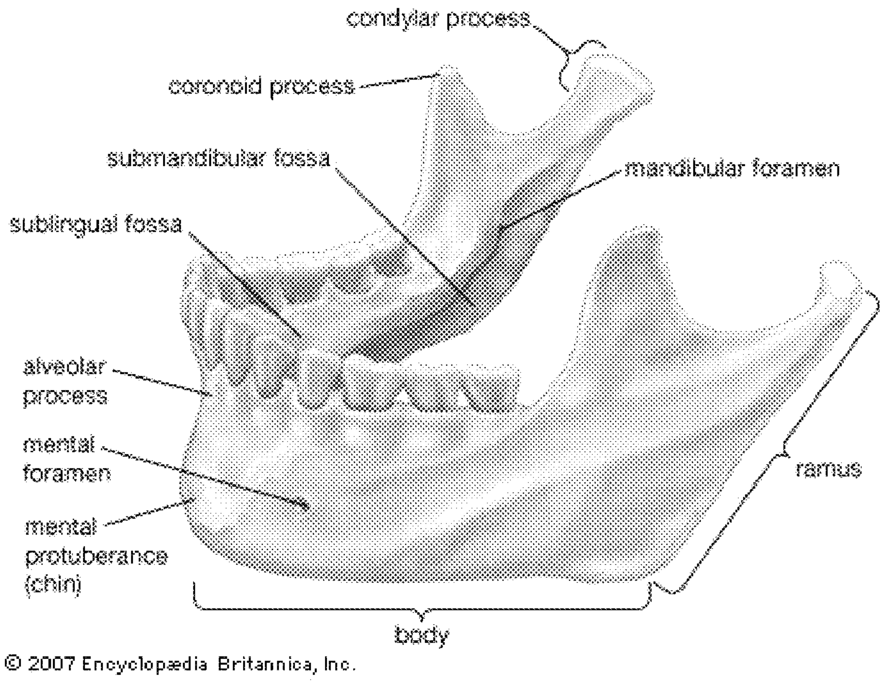
FIG. 2 illustrates the anatomy of the human mandible.
Figure 3:
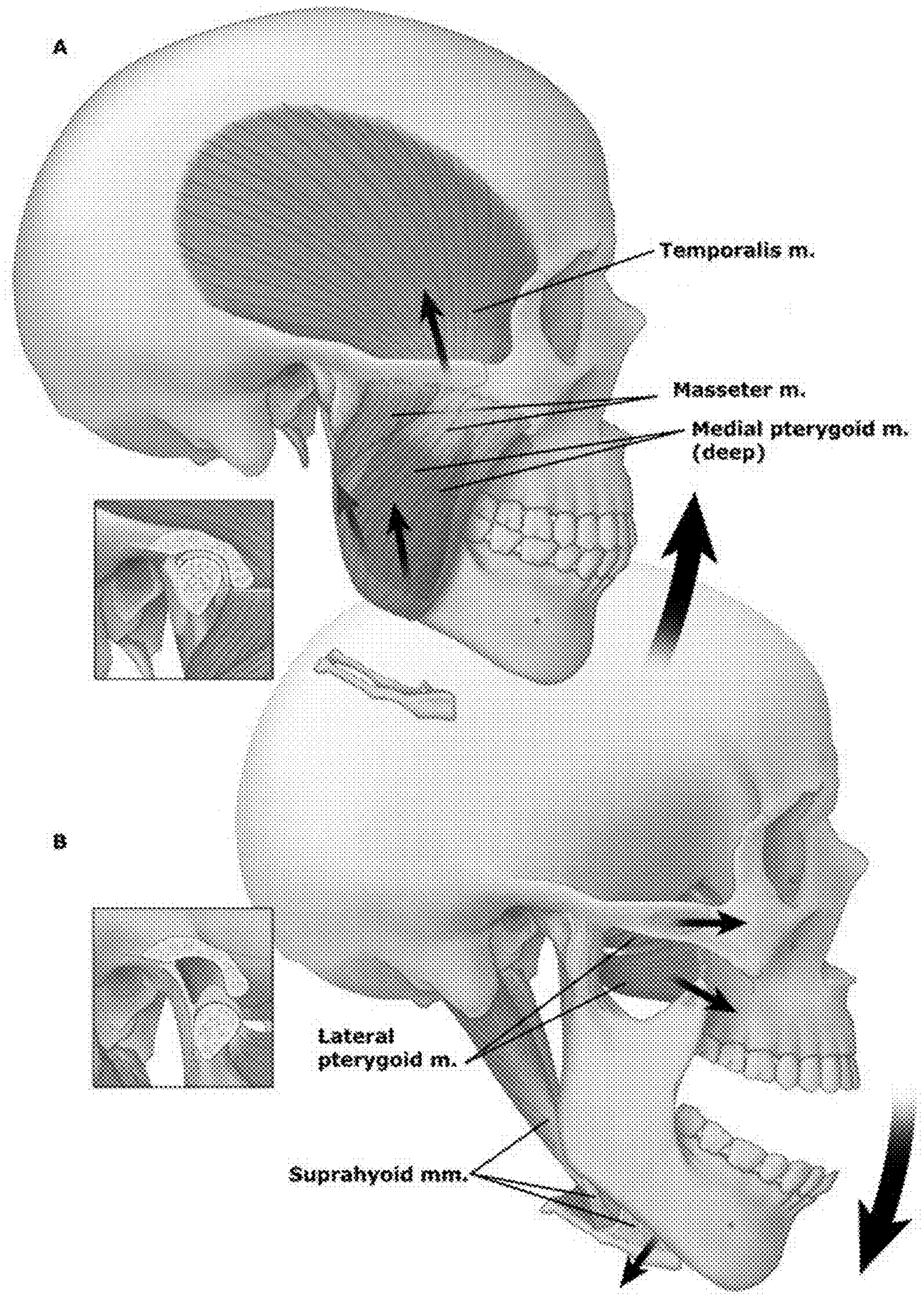
FIG. 3 illustrates the major muscles that move the human mandible during mastication.

For reference, FIG. 2 illustrates the mandible. It is the largest and strongest bone in the face. The mandible forms the lower jaw and holds the lower teeth in place ("*Gray's Anatomy—The Anatomical Basis of Clinical Practice,*" 40th Edition, page: 530). FIG. 3 illustrates the major muscles of the mandible.

The problems with the current standard of care procedures are demonstrated by a study of the biomechanical behavior (stress, strain, and displacement) of a complete, normal mandible during normal mastication. The biomechanical behavior of the mandible was studied using a finite element model that discriminates cortical and cancellous bone, muscle, periodontal ligament, and the different components of the teeth.

In the following example, the inventors investigated and contrasted stress distribution at similar areas of the mandible for these four cases of mastication: 1) normal chewing, 2) a resected mandible (i.e., segmental defect in the $M_1$-3 region) with a single barrel fibular graft and Ti-6Al-4V fixation hardware, 3) a resected mandible with a double barrel fibular graft and Ti-6Al-4V fixation hardware, and, finally (4) in so doing establish a model by which the maximum right or left molar or incisive bite force can be predicted and thereby restored following reconstructive surgery for mandibular segmental defects.

1. Materials and Methods

Modeling

Figure 4:
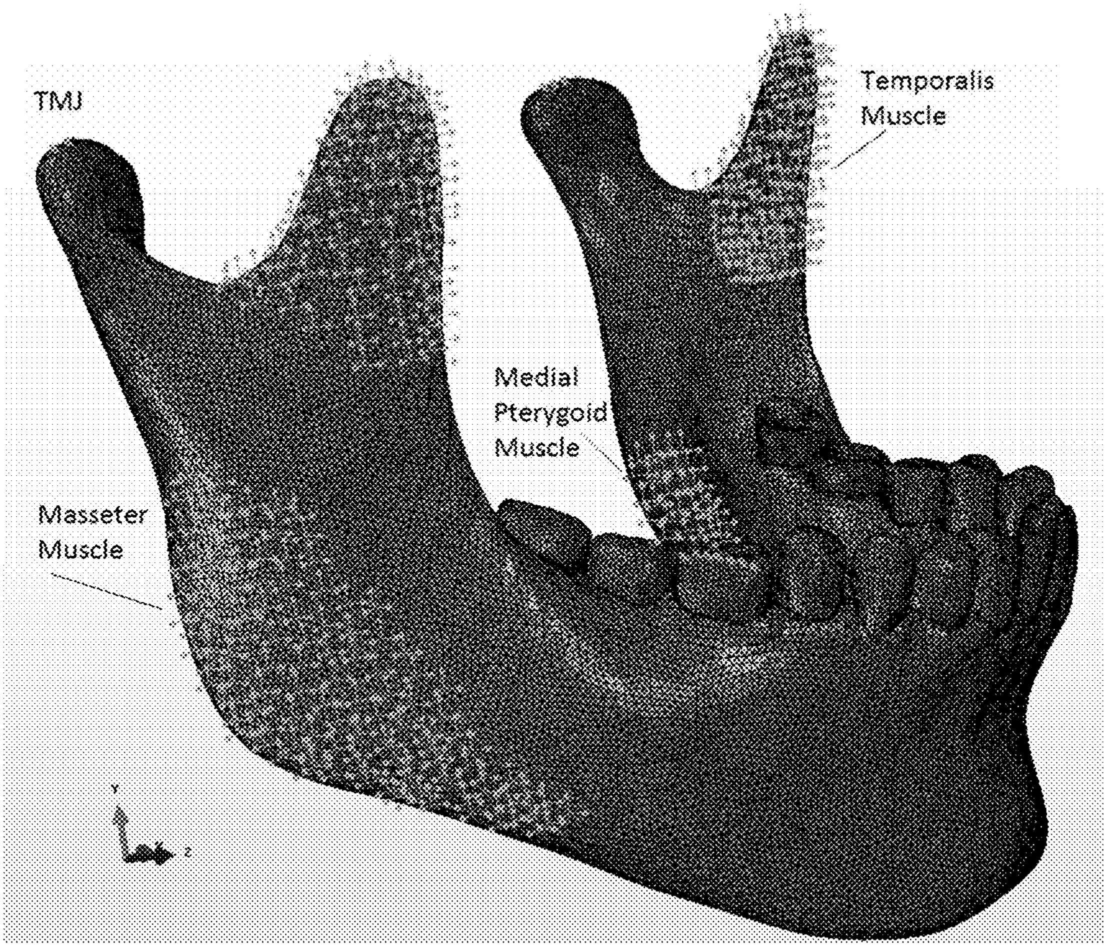
FIG. 4 illustrates a normal adult mandible presenting the Finite Element Model boundary conditions.

A finite element model of a normal (i.e., healthy adult) mandible, illustrated in FIG. 4, was created from a commercially obtained high resolution surface image data set (Print Ready 3D Model Lower Jaw Bone Human). This high resolution data allows us to more accurately model the occlusal surfaces than would be possible from current 3D CT data alone. High resolution occlusal data best obtained from direct intra-oral scans or high resolution scans of dental models. Separate CT data is fit to these surfaces in order to locate internal cortical bone, cancellous bone, periodontal ligament, and dental (i.e., enamel and dentin) surfaces, as well as the temporomandibular joint surface (i.e., thickness and distribution of that cartilage layer) on the head of the mandible. The resected area of the mandible includes the left segment bearing $M_{1-3}$ which has a length of 40 mm. Components of the reconstruction, including the fibular graft, the metallic fixation plates and screws, are all simulated in SolidWorks (Dassault Systèmes, Waltham, MA). The fixation plate holding the inferior fibular barrel graft has 9 threaded holes, a thickness of 1.5 mm, length of 78 mm, and a width of 4 mm (Lovald, S. T., et al., "*Biomechanical optimization of bone plates used in rigid fixation of mandibular fractures*," Journal of Oral and Maxillofacial Surgery, 67 (5): p. 973-985 (2009)). The inventors graphically bent the plate to match the shape of the buccal (external) surface of the grafted bone and the remaining host mandibular anatomy (i.e., the inferior border of the mandible) and verify its contact with a collision detection algorithm. (Note: These plates are usually bent in the Operating Room and their close contact with the underlying bone is verified manually.) For each fixation device a minimum of one screw is placed in each of the remaining mandible segments and one screw on the opposing side of the fibular barrel graft (i.e., screws are placed both sides of the host bone/graft gap). Bicortical screws (i.e., screws that pass through both the lingual and buccal cortices of the graft and the remaining host mandible) are used to fasten the large inferior plate (Lovald, S. T., et al., "*Biomechanical optimization of bone plates used in rigid fixation of mandibular fractures*," Journal of Oral and Maxillofacial Surgery, 67 (5): p. 973-985 (2009)). The simulated screws have a diameter of 1.4 mm. The single barrel fibular graft consists of cortical and cancellous bone layers with a height of 20 mm and a 14 mm width.

In order to fixate the upper (second) fibular barrel graft, the inventors simulated two mini-plates, both of which are slightly bent to fight tightly onto the graft and the superior border of remaining host mandible. Each mini-plate has three threaded holes and is 1 mm thick with a length of 18 mm and width of 2.8 mm. The mini-plates are secured by unicortical screws (Lovald, S. T., et al., "*Biomechanical optimization of bone plates used in rigid fixation of mandibular fractures*," Journal of Oral and Maxillofacial Surgery, 67 (5): p. 973-985 (2009)). The diameter of the four screws securing each mini-plate is 1.4 mm. The vascularized double barrel fibular graft consists of two single barrel grafts, placed together by the surgeon in order to best mimic the contour of the mandible (Lovald, S. T., et al., "*Biomechanical optimization of bone plates used in rigid fixation of mandibular fractures*," Journal of Oral and Maxillofacial Surgery, 67 (5): p. 973-985 (2009)). The height of the two adjacent pieces of the double barrel graft is 38 mm (He, Y., et al., "*Double-barrel fibula vascularized free flap with dental rehabilitation for mandibular reconstruction*," Journal of Oral and Maxillofacial Surgery, 69 (10): p. 2663-2669 (2011)). All of the components were imported into ABAQUS (Dassault Systèmes, Waltham, MA) for a Finite Element Analysis of the expected stress-strain trajectories during mastication at the right $M_1$.

Material Properties

All data pertaining to material properties of our model components are from studies by Andani et al. (Andani, M. T., et al., "*Metals for bone implants. Part 1. Powder metallurgy and implant rendering*," Acta Biomaterialia, 10:4058-70 (2014)), Shetty et al. (Shetty, P., et al., "*A finite element analysis for a comparative evaluation of stress with two commonly used esthetic posts*," European Journal of Dentistry, 7 (4): p. 419 (2013)), and Nagasao et al. (Nagasao, T., et al., "*Biomechanical evaluation of implant placement in the reconstructed mandible*," The International Journal of Oral & Maxillofacial Implants, 24 (6): p. 999-1005 (2008)) as shown in Table 1.

TABLE 1

Material properties for the mastication Finite Element Model components.

| Components | | Stiffness (MPa) | Poisson's ratio |
|---|---|---|---|
| Mandible | Cortical | 24,400 | 0.30 |
| | Cancellous | 3,000 | 0.30 |
| | Teeth | 18,600 | 0.31 |
| | Periodontal ligament | 69 | 0.45 |
| | Ti—6Al—4V | 112,000 | 0.30 |
| Fibular graft | Cortical | 26,800 | 0.30 |
| | Cancellous | 1,650 | 0.30 |

Finite Element Model Mesh

A 4-node linear tetrahedral mesh was used. The number of nodes is 318,814 and the number of elements is 1,512,877 for the normal mandible finite element model. Subsequently, the resected mandible finite element model includes either a single or a double fibular barrel graft and Ti-6Al-4V fixation hardware.

Finite Element Model Boundary Conditions

Boundary conditions including unilateral right first molar maximal occlusion are set as follows. We set up 24 nodes on the outer cortical surface of each mandibular condyle. This allows them to be restrained from movement in all three directions (Korioth, T. W., et al., "*Three-dimensional finite element stress analysis of the dentate human mandible*," American Journal of Physical Anthropology, 88 (1): 69-96 (1992)). The effect of the articular disc is ignored in this study because it is far from the region of our concern (i.e., around the graft). Seven nodes of bite contact on the buccal cusps of the lower right first molar are constrained from movement in all directions, simulating peak bite force (Lovald, S. T., et al., "*Biomechanical optimization of bone plates used in rigid fixation of mandibular fractures*," Journal of Oral and Maxillofacial Surgery, 67 (5): p. 973-985 (2009)) (i.e., these cusps reach maximal approximation between the buccal and lingual cusp rows of the upper molars). The bite force at maximum intercuspation was verified to be 483 N in this study. This represents an 8% discrepancy with the model presented by Korioth et al. (Korioth, T. W., et al., "*Three-dimensional finite element stress analysis of the dentate human mandible*," American Journal of Physical Anthropology, 88 (1): 69-96 (1992)). This discrepancy may be due to differences in mandibular shape, our inclusion of the periodontal ligament, minor differences in the muscle attachment sites, and/or, finally, differences in the summation of the seven node force values we obtain from bite contact. All muscle forces and directions pertaining to a bite force of 526 N on the first molar are taken from the study by Korioth et al. (Korioth, T. W., et al., "*Three-dimensional finite element stress analysis of the dentate human mandible*," American Journal of Physical Anthropology, 88 (1): 69-96 (1992)). Table 2 shows all of the muscle forces and directions, and also the area of each muscle attachment.

TABLE 2

The muscle force is distributed homogeneously across the area of attachment. The X vector direction (right-left) is normal to the sagittal plane with the positive direction pointing toward the left side of the mandible. The Y vector direction (superior-inferior) is normal to the occlusal plane with the positive direction pointing superiorly. The Z vector direction (anterior-posterior) is orthogonal to the remaining two orthogonal axes.

| Muscle Group | | Muscle group weight (N) | Scaling factors: Working side | Scaling factors: Balancing side | Muscle direction: Working side | Muscle direction: Balancing side | Area of attachment (mm$^2$) |
|---|---|---|---|---|---|---|---|
| Masseter | Superfacial | 190.40 | 0.72 | 0.60 | −0.207i + 0.995j + 0.419k | +0.207i + 0.995j + 0.419k | 10.31 ± 1.41 |
| | Deep | 81.60 | 0.72 | 0.60 | | | |
| Pterygoid | Medial | 174.80 | 0.84 | 0.60 | +0.486i + 0.791j + 0.372k | −0.486i + 0.791j + 0.372k | 6.00 ± 1.24 |

TABLE 2-continued

The muscle force is distributed homogeneously across the area of attachment. The X vector direction (right-left) is normal to the sagittal plane with the positive direction pointing toward the left side of the mandible. The Y vector direction (superior-inferior) is normal to the occlusal plane with the positive direction pointing superiorly. The Z vector direction (anterior-posterior) is orthogonal to the remaining two orthogonal axes.

| Muscle Group | | Muscle group weight (N) | Scaling factors Working side | Scaling factors Balancing side | Muscle direction Working side | Muscle direction Balancing side | Area of attachment ($mm^2$) |
|---|---|---|---|---|---|---|---|
| Temporalis | Anterior | 158.00 | 0.73 | 0.58 | −0.149i + | +0.149i + | 13.25 ± 3.3 |
| | Middle | 95.60 | 0.66 | 0.67 | 0.988j + 0.044k | 0.988j + 0.044k | |
| | Posterior | 75.60 | 0.59 | 0.39 | | | |

Muscle forces are distributed homogeneously across the area of attachment in all muscles. The values for area of attachment are taken from Van Eijden et al. (Van Eijden, T., et al., "*Architecture of the human jaw-closing and jaw-opening muscles*," The Anatomical Record, 248 (3): 464-474 (1997)). The area of attachment is not from a patient's CT image, but rather it is approximated based on our reading of reported anatomical data for this isolated mandible (*Gray's Anatomy* (*Barnes & Noble Collectible Editions*)). Muscle forces after mandibular reconstruction are assumed to be 60% of the average value recorded for a healthy adult (Lovald, S. T., et al., "*Biomechanical optimization of bone plates used in rigid fixation of mandibular fractures*," Journal of Oral and Maxillofacial Surgery, 67 (5): p. 973-985 (2009)). Following reconstruction all of the muscles are restored to their normal location. This meant that in some cases small amounts of the muscular sleeve would overlie the grafted bone as well as the remaining host mandible.

2. Results

The results of our analysis were based on the following assumptions: The intersections between teeth/periodontal ligament and periodontal ligament/mandible are tied together completely and homogenously; there is no gap initially between the grafted bone and the remaining host mandible; the screws fixate the hardware (i.e., large- or mini-plates) to the grafted bone and the remaining host mandible. Therefore, the fixation hardware keeps all of the components together securely with only insignificant micro-motion. There is no gap between the plate and the adjacent bone. The fixation hardware fits the bone closely when surgeons bend and attach these plates in the operating room.

Figure 5A:
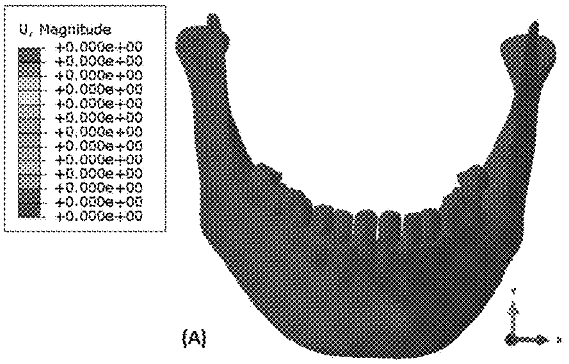
FIG. 5A illustrates the displacement trajectories for the mandible before normal masticatory loading.
Figure 5B:
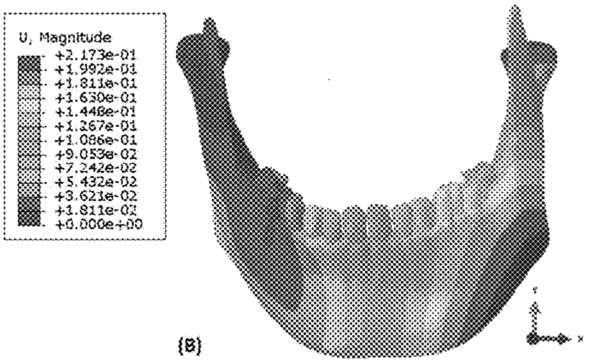
FIG. 5B illustrates the displacement trajectories for the mandible after normal masticatory loading.

Normal Mandibular Masticatory Loading:

FIG. 5 shows displacement loading for the mandible during normal mastication at the right $M_1$: a) before loading, and b) under right-side (i.e., so-called "working side") unilateral loading. Since the range of displacement is small (maximum of 0.2 mm), deformation is magnified 80 times to see it more clearly. The deformation is helically upward and toward the working side. The displacement around the restrained regions of bite contact and the two condyles is approximately zero. The greatest displacement is on the balancing side at the angle and along the inferior corpus (body) region of the mandible.

Figure 6:
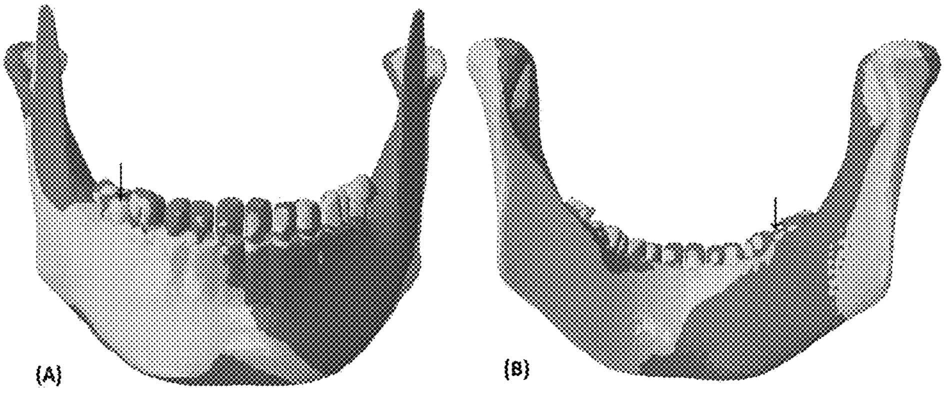
FIG. 6 illustrates compression and tension results for mastication at the right $M_1$ (arrow) in the normal mandible: a) buccal side, b) lingual side. White represents compression and brown represents tension.

We depict compression and tension during mastication at the right $M_1$ (at the arrow) in the normal mandible as a result of the aforementioned loading as shown in FIG. 6. Compression and tension are defined to be hydrostatic pressure which is the third invariant of the element stresses. The white and brown regions show areas under compression and tension, respectively. The buccal surface (6A) of the balancing (left) side corpus displays mostly tension stress and on the lingual surface (6B) of the balancing side we see mostly compressive stress.

Figure 7:
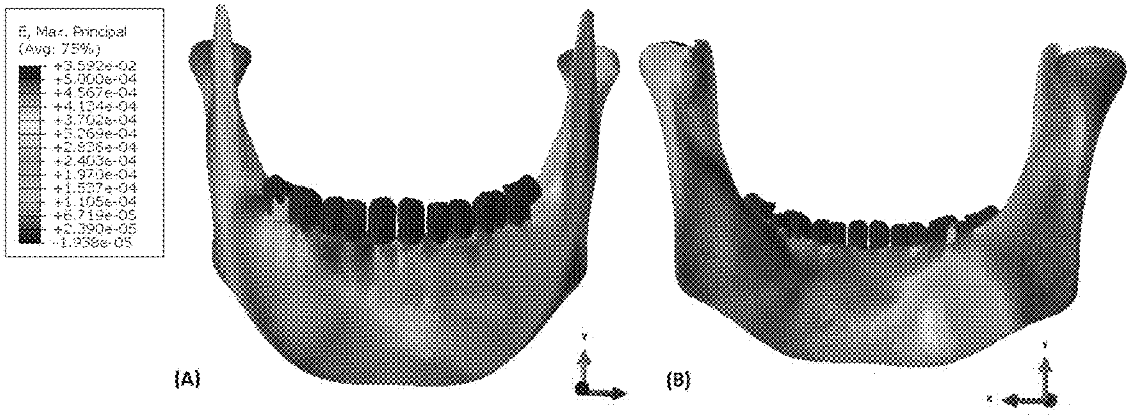
FIG. 7 illustrates strain distribution for a normal mandible during mastication at the right $M_1$; a) buccal view, b) lingual view.

FIG. 7 shows the strain distribution for a normal mandible during mastication at the right $M_1$. Highest principal strain can be seen in the periodontal ligament of the right first molar and at both mandibular heads (condyles). The neck of the left condyle, the mandibular notch, the medial ramus and symphysis (more on the balancing side than the working side) also show strain concentrations. It is interesting to see that strain is concentrated at the "corners" where the two corpi meet (i.e., the mental tubercles) on either side of the symphysis, externally on the balancing side and internally on the working side.

Figure 8:
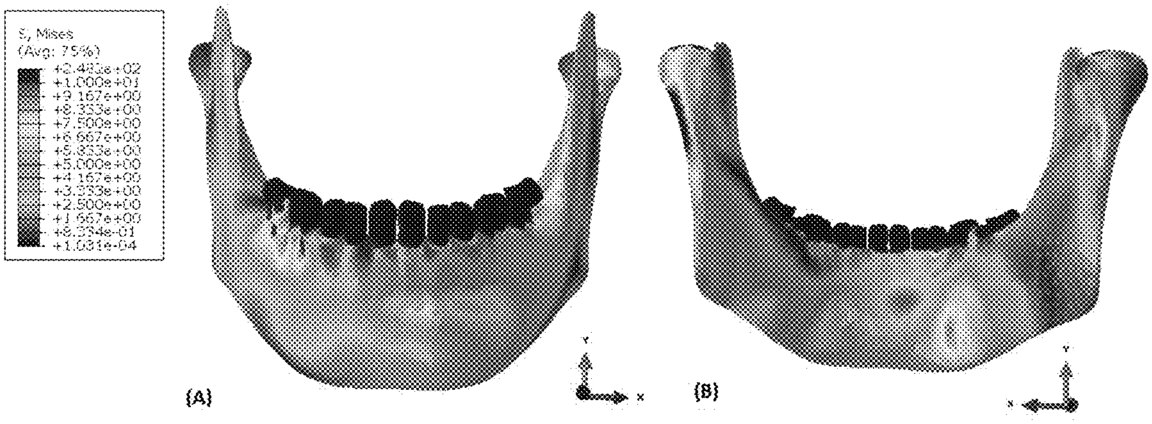
FIG. 8 illustrates von Mises stress distribution of a normal mandible during mastication at the right $M_1$; a) buccal view, b) lingual view.

FIG. 8 presents the von Mises stress that occurs during mastication at the right $M_1$ in the normal adult mandible. The maximum peak stress regions occur on the right first molar tooth and the buccal alveolar ridge in the right molar area and at the mandibular head of both condylar processes. The ramus, neck of the condylar process, symphyses, and the mandibular notch are some of the areas where we can see von Mises stress concentration. These concentrations are lower on the balancing side than on working side. This is expected as the stress created by the balancing side muscles pulling on the mandible is less concentrated than that that occurring between the teeth during chewing.

The Effect of Using Ti-6Al-4V Fixation Hardware and a Fibular Graft on Masticatory Stress Distribution We graphically illustrate the change in stress at peak exertion during the chewing stroke for the case of a normal adult mandible, a resected mandible with a single barrel fibular graft and Ti-6Al-4V fixation hardware, and a resected mandible with a double barrel fibular graft and Ti-6Al-4V fixation hardware. The regions of peak stress can be investigated. This analysis leads to two concerns for patients where the fixation hardware is not removed after the grafted fibular bone has healed with the remaining host mandible: (1) the possibility of fixation hardware causing both: (1) stress shielding of some of the grafted bone and host mandible, and (2) stress concentration, especially at fixation screws.

Figure 9:
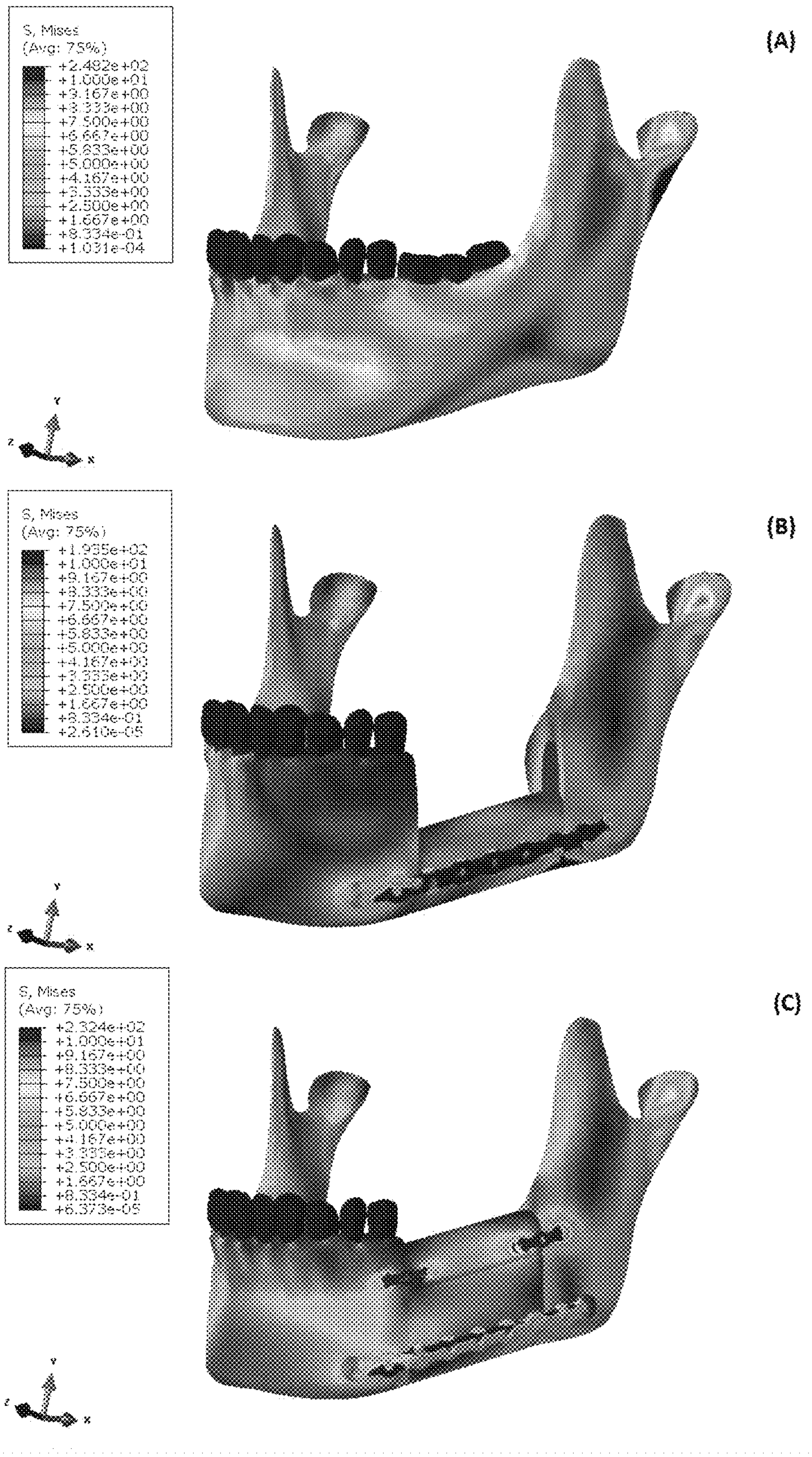
FIG. 9 illustrates stress distribution patterns around the implanted fibular graft during mastication; A) normal mandible, B) mandible reconstructed using Ti-6Al-4V hardware and a single fibular barrel graft, and C) mandibular reconstruction using Ti-6Al-4V hardware and a folded double fibular barrel graft; (Unit: Megapascal).

FIG. 9 illustrates abnormal stress shielding and abnormal stress concentration in the mandible as a result of the Ti-6Al-4V fixation plate that is attached to either a single fibular barrel graft or a double fibular barrel graft.

The highest stress concentration is carried by the Ti-6Al-4V fixation plate for the single fibular barrel graft at 2.05 times that seen when a double fibular barrel graft is used. However, the stress concentration at the mini-plates used in a double fibular barrel graft is also high, especially at the superodistal mini-plate. A similar stress concentration is seen inferiorly in the case of a single fibular barrel graft (FIG. 9C). In addition, the stress concentration on the screws, which is a common reason for implant failure, reduced by the factor of 1.63 when double-barrel fibular graft is used.

For the case of a single barrel fibular graft, FIG. 9B graphically shows high stress shielding of the superior regions of remaining host mandible, and also in the corpus region. Stress shielding on these regions is less the case when a double fibular barrel graft is used. This may be due to the increased continuity between the grafted bone and the mandible. On the other hand, overall stress shielding of a single fibular barrel graft is less that seen with a double fibular barrel graft.

Figure 10:
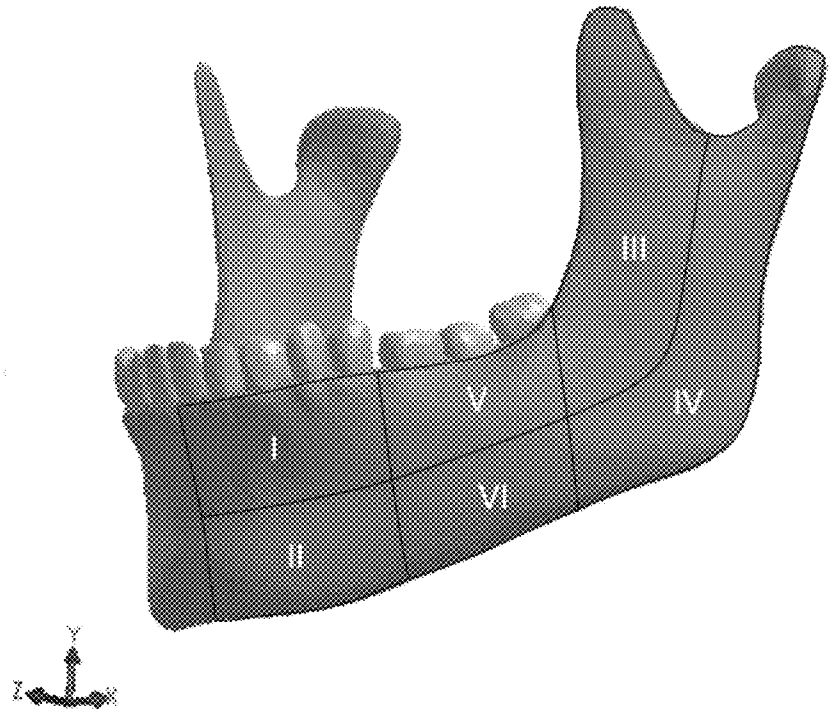
FIG. 10 illustrates six zones on the mandible.
Figure 11:
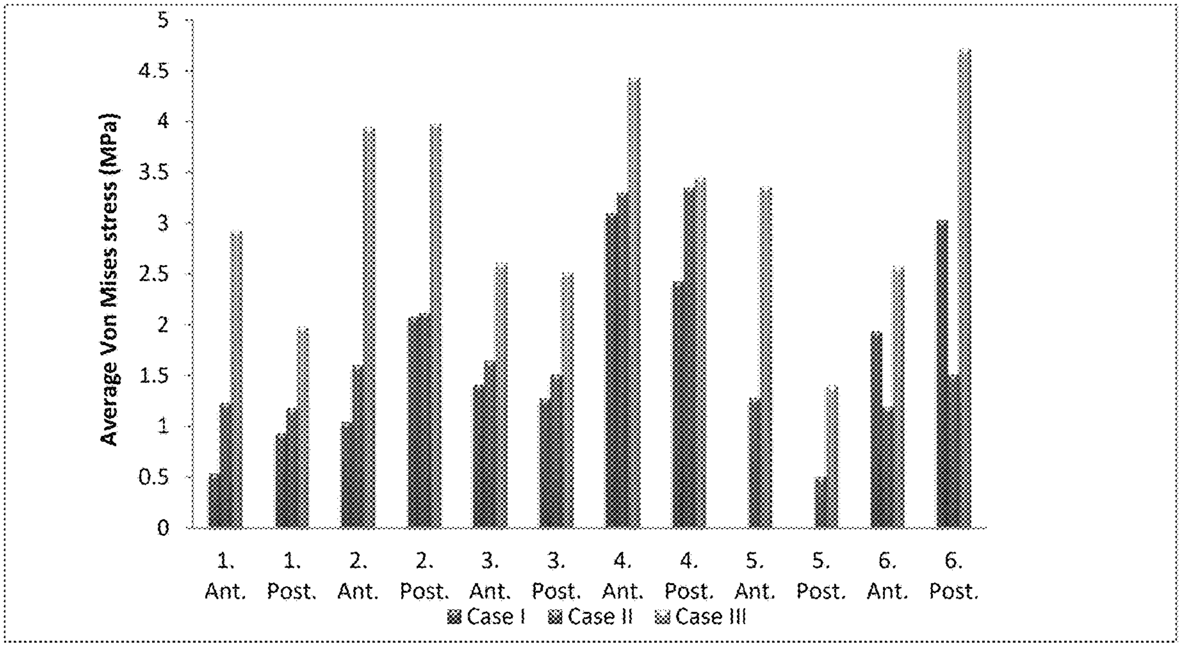
FIG. 11 illustrates average von Mises stress on the cortical bone portion of a mandible at six different zones both on the anterior side and posterior side for the following cases: Case 1) Reconstructed mandible with a single barrel fibular graft and Ti-6Al-4V fixation hardware, 2) Reconstructed mandible with a double barrel fibular graft and Ti-6Al-4V fixation hardware, and 3) Normal mandible.

In order to better understand the stress distribution of the reconstructed mandible we compared average von Mises stress on the anterior cortical and posterior bone cortex in zone VI (FIG. 10) of the mandible for the following cases: 1) Reconstructed mandible with a single barrel fibular barrel graft and Ti-6Al-4V fixation hardware, 2) Reconstructed mandible with a double fibular barrel graft and Ti-6Al-4V fixation hardware, and finally 3) normal mandible. With reference to FIG. 11, generally, we can see stress shielding occurring in both cases. Stress shielding is caused by the highly efficient uptake of the chewing load by the Ti-6Al-4V hardware. Although there is more stress on the graft in the single fibular barrel case, it is preferable to have a double fibular barrel as it repairs both zones 5 and 6 and causes less stress shielding of the surrounding host mandible than with the single fibular barrel graft. The missing bone in zone 5 results in a gap at the top of single barrel, and also disability of future dental implant and a loss of facial contour. Facial contour is also at risk when there is resorption of grafted or host bone that is stress shielded due to the unfilled gap.

3. Conclusion

Segmental mandibular defects commonly occur following treatment for benign tumor or malignant primary bone neoplasms, trauma, infections, or osteoradionecrosis. Mandibular reconstruction surgery is undertaken to repair the defect and restore chewing, speaking, swallowing, and breathing function as well as aesthetic form. Current methods for mandibular reconstruction almost uniformly use Ti-6Al-4V fixation hardware and vascularized fibular bone transplantation of either double or single barrel fibular grafts. One of the main challenges in using permanent Ti-6Al-4V fixation plates is the stress shielding and stress concentration caused by the high stiffness of this hardware. While these biocompatible and very stiff plates provide fixation during healing, it should be noted that the healed graft/host junction is thereafter significantly stress-shielded.

We have established a model for verifying maximal right or left molar or incisive bite force based on 3D CT data of the relevant structures and cross-sectional data of the three major chewing muscles. In our simulation study we observed that reconstruction using a double fibular barrel graft helped recreate a more normal stress-strain distribution in the reconstructed mandible than did a single fibular barrel graft. We observed that using a single fibular barrel graft removes stress from a large portion of the mandibular alveolar process and corpus regions in the remaining host mandible. This phenomenon is observed with a double barrel fibular graft and a Ti-6Al-4V fixation plate, but it is reduced.

Long term stress concentration at fixation plates and especially metallic screws may also put them at risk for fracture or loosening in the future. It is shown that a double barrel graft causes less stress concentration on both fixation plates and screws.

If fixation hardware is to be implanted permanently for the reconstruction of mandibular segmental defects, it may be useful to study how less stiff hardware might both provide sufficient immobilization during healing.

Example: Patient Specific Implant Design: Geometry and Material Properties for Reconstruction of the Mandible Tumor resection, trauma, and inflammation cause mandibular segmental defects (i.e., a complete segment is missing resulting in two separate parts), which may lead to airway obstruction, disfigurement, disturbance in speech and swallowing, and diminished masticatory ability. Reconstruction methods and techniques need to be applied to restore the mandible aesthetic and function, including repair of mandible continuity and muscles attachment. Despite all the progress in surgically treating this condition over the last 30-40 years, none of the current techniques meet all the needs to completely restore the shape and functionality of the lost bone over the long term (e.g., more than 10 years) (Abbas A., "*Reconstruction skeleton for the lower human jaw using CAD/CAM/CAE*," Journal of King Saud University-Engineering Sciences, 24:159-64 (2012)). At present, the standard of care for a segmental defect of the mandibular corpus is implantation of a Ti-6Al-4V bar adjacent to the gap. Allograft bone is attached to this immobilizing bar and allowed to heal in place. However, use of semi-rigid mesh panel as a substitutes for rigid plates has been suggested due to better cosmetic appearance, need for fewer screws, and shorter procedures (Lazaridis, N., et al., "*The use of titanium mesh sheet in the frontozygmatico-orbital region*," Case reports. Australian Dental Journal, 43:223-8 (1998)). In either case, this arrangement allows the muscles to begin working immediately following surgery. This is critical if the patient is to maintain the ability to chew and speak. The junction between the remnant host mandible and the newly engrafted bone is immobilized allowing them to heal. Vascularized autograft fibular segments are the standard of care surgical technique with reports of high success rate of up to 95% of bone incorporation rather than nonvascularized allograft bones (Lazaridis, N., et al., "*The use of titanium mesh sheet in the frontozygma tico-orbital region*," Case reports. Australian Dental Journal, 43:223-8 (1998); Cohen, A., et al., "*Mandibular reconstruction using stereolithographic* 3-*dimensional printing modeling technology*," Oral Surgery, Oral Medicine, Oral Pathology, Oral Radiology, and Endodontology, 108:661-6 (2009); Tsuchiya, S., et al., "*Clinical factors associated with postoperative complications and the functional outcome in mandibular reconstruction*," Microsurgery (2013); Hidalgo, D. A., et al., "*Free-flap mandibular reconstruction: a* 10-*year follow-up study*," Plastic and Reconstructive Surgery, 110:438-49 (2002)). Allografts are transplanted with intact blood supply, so the healing period would reduce significantly and complications such as resorption and infection are minimized (Goh, B. T., et al., "*Mandibular reconstruction in adults: a review*," International Journal of Oral and Maxillofacial Surgery, 37:597-605 (2008)). It should be noted that some patients cannot tolerate the complications and prolonged hospitalization associated with vascularized bone grafting. Therefore, the main surgery is postponed to a second operation by using a shaped acrylic spacer (Gregory, G., et al., "*Improving the mandibular reconstruction plate: technical innovation*," Journal of the Royal College of Surgeons of Edinburgh, 45:120-1 (2000). The fibula is the most common site for bone graft harvesting because it offers an adequate length of bone for mandibular defect and is not as frequently associated with post-operative severe morbidity (die-back of the remaining bone) and pain at the donor site. However, the lack of appropriate height and width of a fibular graft (which are necessary for future dental prosthesis and mandible continuity) may create a demand for additional bone grafting or distraction osteogenesis procedures (Wong, R. et al., "*Biomechanics of mandibular reconstruction: a review*," International Journal of Oral and Maxillofacial Surgery, 39:313-9 (2010)). The iliac crest is another common option for bone harvesting and can be applied only for cases with small defects (i.e., with defects smaller than 6 mm) due to lack of adequate length (Tie, Y., et al., "*Three-dimensional finite-element analysis investigating the biomechanical effects of human mandibular reconstruction with autogenous bone grafts*," Journal of Cranio-maxillofacial Surgery, 34:290-8 (2006); Hayden, R. E., et al., "*Reconstruction of the segmental mandibular defect: current state of the art*," Current Opinion in Otolaryngology & Head and Neck Surgery, 20:231-236 (2012); Chang, Y. M., et al., "*Dental implant outcome after primary implantation into double-barreled fibula osteoseptocutaneous free flap-reconstructed mandible*," Plastic and Reconstructive Surgery, 128 (6): 1220-8 (December 2011)).

There are unfortunately some clinical problems of concern regarding mandibular reconstruction failure. Stress shielding is a major concern (Kennady, M. C., et al., "*Histomorphometric evaluation of stress shielding in mandibular continuity defects treated with rigid fixation plates and bone grafts*," International Journal of Oral and Maxillofacial Surgery, 18:170-4 (1989)). If the immobilization hardware is left in the patient following the attachment of crowns to dental implants (i.e., titanium posts implanted in the grafted bone), it will be difficult to establish the previously transfer of load from muscles to mandible to teeth and from teeth to mandible (i.e., crown to post to mandible) during chewing without significant differences brought about by the immobilization hardware with both stress shielding and stress concentrating at new locations.

A mandible is generally subjected to two types of loading, muscle forces and bite forces. The masseter, temporalis, and pterygoid muscles are the three most important muscles providing position and force during incision and mastication. These muscles are active even when the mandible is at rest. The amount of muscle forces depend on many factors including the hardness of the food, occlusion state (rest or chewing), bite loading conditions (balanced or unbalanced loading, bilateral or unilateral loading, grinding, or clenching), and the location of the teeth which are involved relative to the muscles and the balancing side jaw joint (Ingawalé, S. M., et al., "*Biomechanics of the Temporomandibular Joint*," Chapter 7 of Human Musculoskeletal Biomechanics (2012); Kavanagh, E., et al., "*Use of finite element analysis in presurgical planning: treatment of mandibular fractures*," Irish Journal of Medical Science, 177:325-31 (2008)).

Stress shielding of the reconstructed mandible may result from the high modulus of plates, screws, and bone graft. This stiffness mismatch leads to an uneven load sharing (stress distribution) between the implanted device or bone and the mandible and may result in implanted bone weakening and implant device failure (Yarlagadda, P. K., et al., "*Recent advances and current developments in tissue scaffolding*," Bio-Medical Materials and Engineering, 15:159-77 (2005); Keller, E. E., et al., "*Endosseous implant and autogenous bone graft reconstruction of mandibular discontinuity: a 12-year longitudinal study of 31 patients*," The International Journal of Oral and Maxillofacial Implants, 13:767 (1998)).

The geometry of an implant significantly changes the distribution of stresses on the bones surrounding the implant. The area of bone-graft interface and the diameter of graft are the two design factors which affect stress distribution along the reconstructed mandible (Baggi, L., et al., "*The influence of implant diameter and length on stress distribution of osseointegrated implants related to crestal bone geometry: a three-dimensional finite element analysis*," The Journal of Prosthetic Dentistry, 100:422-31 (2008)).

One of the goals in the reconstruction procedures to keep the interface cross section areas of the bone graft and the host bone the same to produce a continuous profile of stress and mitigate stress concentration (Tie, Y., et al., "*Three-dimensional finite-element analysis investigating the biomechanical effects of human mandibular reconstruction with autogenous bone grafts*," Journal of Craniomaxillofacial Surgery, 34:290-8 (2006)). The areas of high and low stress concentrations can be studied by FEA. Based on the result of the simulation, high stress areas of the grafted bone and implant are thickened and the low stress areas are reduced in size to reduce the possibility for stress shielding (Li, P., et al., "*Optimal design of an individual endoprosthesis for the reconstruction of extensive mandibular defects with finite element analysis*," Journal of Cranio-Maxillofacial Surgery, 42 (1): 73-78 (2014)). Of course decisions such as these will affect the aesthetic outcome as well.

Infection is another issue of concern with the use of metallic implants. This risk is the primary motivation for removal of rigid plates, semi-rigid meshes, and screws after an adequate period of healing and prior to insertion of dental implants (Murthy, A. S., et al., "*Symptomatic plate removal in maxillofacial trauma: a review of 76 cases*," Annals of Plastic Surgery, 55:603-7 (2005)). The loss of cheek contour and interruption of vascular supply to the underlying bone graft area are the two common problems associated with fixation removal (Blackwell, K. E., et al., "*The bridging lateral mandibular reconstruction plate revisited*," Archives of Otolaryngology-Head & Neck Surgery, 125 (9): 988-93 (1999)). It is believed that removal of fixation plates is also beneficial for elimination the stress shielding effect. Bringing the reconstructed mandible under the normal loading pattern. This way, the mandible would be subjected to functional loads and subsequently would undergo the remodeling necessary for bone formation at the host-implant interface (Abu-Serriah, M., et al., "*Mechanical evaluation of mandibular defects reconstructed using osteogenic protein-1 (rhOP-1) in a sheep model: a critical analysis*," International Journal of Oral and Maxillofacial Surgery, 34:287-93 (2005); Warnke, P., et al., "*Growth and transplantation of a custom vascularized bone graft in a man*," The Lancet, 364:766-70 (2004); Abu-Serriah, M., et al., "*Contour and volume assessment of repairing mandibular osteoperiosteal continuity defects in sheep using recombinant human osteogenic protein 1*," Journal of Cranio-Maxillofacial Surgery 34:162-7 (2006)). It is expected that biocompatible metals will have very low risk of infection and therefore do not need to be removed (Abbas, A., "*Reconstruction skeleton for the lower human jaw using CAD/CAM/CAE*," Journal of King Saud University-Engineering Sciences, 24:159-64 (2012); Lazaridis, N., et al., "*The use of titanium mesh sheet in the frontozygmatico-*

*orbital region*," Case reports. Australian Dental Journal 43:223-8 (1998); Blackwell, K. E., et al., "*The bridging lateral mandibular reconstruction plate revisited*," Archives of Otolaryngology-Head & Neck Surgery, 125:988 (1999); Yerit, K. C., et al., "*Fixation of mandibular fractures with biodegradable plates and screws*," Oral Surgery, Oral Medicine, Oral Pathology, Oral Radiology, and Endodontology, 94:294-300 (2002)). For mandibular procedures, only 2 percent of titanium mesh (Dérand, P., et al., "*Imaging, Virtual Planning, Design, and Production of Patient-Specific Implants and Clinical Validation in Craniomaxillofacial Surgery*," Cranialmaxillofacial Trauma and Reconstruction, 5:137 (2012)) require mesh removal, while the plate removal is 17 percent for plates used for trauma and 7 percent for those used for orthognathic surgery (Lazaridis, N., et al., "*The use of titanium mesh sheet in the frontozygomatic orbital region*," Case reports. Australian Dental Journal 43:223-8 (1998)).

Another potential problem for mandibular reconstruction is muscle re-attachment. Incision and masticatory forces subject the mandible, and through the mandible the teeth, to contractile muscle forces during normal mastication and speech. It is possible that the masticatory muscles (i.e., temporalis, pterygoid, and masseter muscles), and thus the entheses (i.e., tendon insertions) will have to be detached from their original site and attached to grafted bone or metallic implants during a segmental defect repair surgery. It should be considered that segmental defect repair that includes the angle of mandible would cause additional problems, because all the masticatory muscles are attached to the angle. Failure for these muscles to re-attach to host bone, grafted bone, or an implant is rare but not unheard of; in these cases secondary re-attachment is often successful (Thomas, M. A., et al., "*Masseter muscle reattachment after mandibular angle surgery*," Aesthetic Surgery Journal, 29:473-6 (2009)). In many cases the muscles can be merely reapproximated, while in other cases they are sutured, with the sutures sometimes being attached to bone-anchored plates and screws (Choukas, N. C., et al., "*The reattachment of the masseter muscle to the mandible*," Oral Surgery, Oral Medicine, Oral Pathology, 25:889-95 (1968); Barone, C. M., et al., "*Temporalis muscle resuspension using titanium miniplates and screws: technical note*," Neurosurgery, 48:450-1 (2001)).

The mechanical properties of the mandible bone are systematically extracted, measured, compared, and catalogued throughout the mandible by this invention. It is well known that there is spatial variation in properties along and across musculoskeletal structures (Korioth, T. W., et al., "*Three-dimensional finite element stress analysis of the dentate human mandible*," American Journal of Physical Anthropology, 88 (1): 69-96 (1992); Tie, Y., et al., "*Three-dimensional finite-element analysis investigating the biomechanical effects of human mandibular reconstruction with autogenous bone grafts*," Journal of Craniomaxillofacial Surgery, 34 (5): 290-298 (2006); Wong, R. C., et al., "*The modular endoprosthesis for mandibular body replacement. Part 2: Finite element analysis of endoprosthesis reconstruction of the mandible*," Journal of Craniomaxillofacial Surgery, 40 (8): e487-e497 (2012)).

Figure 12:
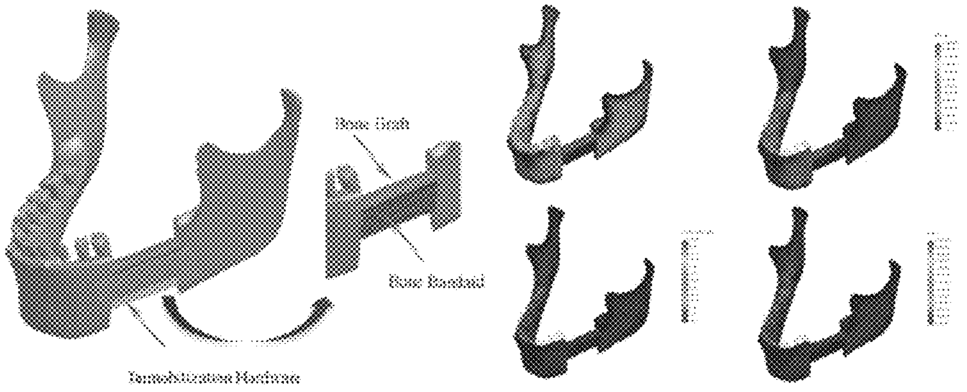
FIG. 12 illustrates a mandible segmental defect composite implant with "Bone Bandaid"—(Left) immobilization hardware (right) FEA of healing: (TL) The FEM mesh (TR) displacement contour (BL) stress contour (BR) strain contour of mandible with immobilization hardware removed and Bone Bandaid integrated into the bone graft. Immobilization hardware either resorbs or is removed after grafted bone heals in situ.

These properties have been studied at submillimeter resolution. The invention determines the patient-specific strain pattern. Using this pattern and Finite Element Analysis (FEA) the desired gradient of mechanical property requirements of the engrafted bone, immobilization hardware, a new element which is part of this invention, the "Bone Bandaid" (discussed in more detail in Section III below), and dental implants are designed. We also image the available bone and bring that bone's shape, virtually, into the graft site in order to provide guidance to the surgeon and to design another part of this invention, the "Bone Bandaid," as shown in FIG. 12. This FEA is also used to design, as shown in FIG. 12 the bone graft immobilization hardware, its fixation sites, and the dental implant posts that will be inserted during this surgery. Subsequently, after the immobilization hardware is removed or degrades, the new bone will be loaded through the portion of the bone bandage that is affixed to the bone surrounding the surgically created defect. Since the bone grafts will not initially be shaped like the mandible segment they replace, grafted bone will not immediately have strong bone in the all the areas previously loaded in the mandible.

If the Bone Bandaid is fabricated from a superelastic material, it will actively distribute load from the host bone to those areas after the grafted bone has healed to the host bone and the fracture immobilization hardware has resorbed or been removed (i.e., the area where the Bone Bandaid is placed is no longer shielded). As with a Band-Aid® that holds a skin wound together to avoid over-concentration of strain at the gap and align traction to other directions, the Bone Bandaid can stretch thus does not completely avoid strain across the bone-implant boundary. However, it attempts to redirect most strain along predicted normative directions. It is essential that the Bone Bandaid carry strain along useful trajectories from the host bone to the graft and/or implant in ways that preserve shape and especially bone mass around the titanium dental implant posts. The new loading pattern will drive bone graft remodeling so that it becomes strong in areas where the mandible had been strong, thereby preserving the grafted bone over the long term, including bone sufficient to support dental implants. Once the grafted bone is healed and the dental posts are well integrated, perhaps after 6 months, crowns will be added to the dental posts to allow chewing on that side of the mandible. However, during this entire period chewing will occur on the other side, the mandible will be under load, all the muscles working, and the patient will be able to speak. To identify the forces on the mandible, we use a 3D CT image of the patient and extract a CAD Finite Element Model (FEM) with accurate depiction of the shape and size of the mandible, teeth, and chewing muscles.

Biting is a complex dynamic process which involves synchronous movements of the mandible in a rhythmic fashion (Lovald, S. T., et al., "*Biomechanical optimization of bone plates used in rigid fixation of mandibular fractures*," Journal of Oral and Maxillofacial Surgery, 67 (5): 973-85 (2009)). In order to accurately model the mechanics of jaw movement, the FEM should be loaded using muscle forces instead of fixing the mandible in place (Lovald, S. T., et al., "*Biomechanical optimization of bone plates used in rigid fixation of mandibular fractures*," Journal of Oral and Maxillofacial Surgery, 67 (5): 973-85 (2009); Wong, R. C., et al., "*The modular endoprosthesis for mandibular body replacement. Part 2: finite element analysis of endoprosthesis reconstruction of the mandible*," Journal of Craniomaxillofacial Surgery, 40 (8): e487-97 (2012)). We then back-calculate the vectors, forces, and strain pattern undergone by the healthy mandible and teeth during biting. The muscle forces that are generated due to the chewing muscles have been obtained using the method described by van Essen et al. (van Essen, N. L., et al., "*Anatomically based modeling of the human skull and jaw*," Cells Tissues Organs, 180 (1): 44-53 (2005)) as shown in Table 3.

TABLE 3

Muscle forces and vectors of the masticatory muscles according to van Essen.

| Label | Side | Muscle | X | Y | Z |
|---|---|---|---|---|---|
| M1 | L | Deep masseter | −44.554 | −29.213 | 61.853 |
| M2 | R | Deep masseter | 44.554 | −29.213 | 61.853 |
| M3 | L | Superficial masseter | −39.413 | 79.778 | 168.314 |
| M4 | R | Superficial masseter | 39.413 | 79.778 | 168.314 |
| M5 | L | Medial pterygoid | 59.596 | 49.552 | 105.083 |
| M6 | R | Medial pterygoid | −59.596 | 49.552 | 105.083 |
| M7 | L | Anterior temporalis | −23.071 | 6.813 | 152.982 |
| M8 | R | Anterior temporalis | 23.071 | 6.813 | 152.982 |
| M9 | L | Posterior temporalis | −14.781 | −50.760 | 33.684 |
| M10 | R | Posterior temporalis | 14.781 | −50.760 | 33.684 |

Note:
positive and negative values denote direction according to x, y, and z-axis.

Exact muscle forces will be adjusted based on each muscle's cross-sectional area as seen in the patient's 3D CT after Korioth et al. (Korioth, T. W., et al., "*Three-dimensional finite element stress analysis of the dentate human mandible*," American Journal of Physical Anthropology, 88 (1): 69-96 (1992)).

In order to obtain the specific equivalent bite load, a simulation is carried out where the biting motion is constrained against upward movement and the muscle loads are gradually and proportionally increased as the reaction force matches the biting force required to chew. In this step, the masticatory muscles are given fixed boundary conditions and the loads applied for incision or mastication. This "back-calculation" of the mechanics of a person's chewing apparatus will be used to design the mandibular bone implant to have desired mechanical and functional behavior. The implant will conduct strain to the bone engrafted in a segmental defect (i.e., defects that form a complete gap) of the mandible that is to be created during the surgery as demonstrated in FIG. 12.

Section II: Porous Nitinol as a Substitute for Ti-6Al-4V Fixation Hardware

The alloplastic materials that are suitable for fabricating the patient-specific implant include, metals, polymers and ceramics. For example, the patient-specific implant or implant component can be a ceramic, e.g., hydroxyapatite (HA) or tricalcium phosphate (TCP) (Zhim, F., et al., "*Personalized implant for high tibial opening wedge: combination of solid freeform fabrication with combustion synthesis process*," Journal of Biomaterials Applications, 27 (3): 323-32 (September 2012)). However, the majority of pure metals are not useful because they rapidly corrode and/or are not biocompatible. Biocompatibility and other properties are important for the selection of appropriate materials for use with the patient-specific implants.

To address the issues with the stiffness mismatch of the fixation hardware noted above, the inventors next investigated the use of alternative materials for the fixation hardware to determine if less stiff hardware could be designed and utilized for reconstruction surgery. It is a goal to develop stiffness matched fixation devices by using less stiff, biocompatible materials. A leading candidate to replace Ti-6Al-4V is nitinol (nickel titanium or NiTi) or possibly a porous form of nitinol. In particular, we investigated the use of porous nitinol (NiTi) as a substitute for Ti-6Al-4V hardware. One issue to address is whether porous nitinol will have sufficient stiffness for fixation during a 6-9 month healing and remodeling period. It is a further goal to obtain a stiffness in the material as close to mandibular cortical bone as possible. However, because the fixation hardware cannot have the same geometry or location as the graft, and because the fixation hardware must prevent more than 300 μm of displacement for at least six weeks during the healing process, it most likely needs to be stiffer than the surrounding mandibular cortical bone. In alternative embodiments, small strain guiding, fixation hardware may be countersunk directly into the cortical bone.

In this study, we compare finite element models of the fixation hardware with a geometry currently in clinical use fabricated from either Ti-6Al-4V or stiffness-matched nitinol. Our results suggest that a stiffness-matched nitinol fixation device is more likely to recreate normal stress-strain trajectories following reconstructive surgery for a mandibular segmental defect than a Ti-6Al-4V fixation device with the same geometry. This outcome bodes well for restoration of the chewing, speaking, swallowing, and breathing functions performed by the mandible.

Current Ti-6Al-4V fixation hardware is used throughout the body and provides immobilization following trauma or reconstructive surgery so that the repositioned bone fragments can heal (Shayesteh Moghaddam, N., et al., "*Metallic Fixation of Mandibular Segmental Defects: Graft Immobilization and Orofacial Functional Maintenance*," (in revision); Shayesteh Moghaddam, N., et al., "*Enhancement of Bone Implants by Substituting Nitinol for Titanium* (*TI-6AL-4V*): *A Modeling Comparison,*" *ASME* 2014 *Conference on Smart Materials, Adaptive Structures and Intelligent Systems*, Newport, Rhode Island (2014)) when it is not sufficient, possible, or dramatically inconvenient to use external fixation (e.g., wiring the teeth shut, plaster casts). Healing can be monitored radiologically to determine when removal is safe. However, while it would reduce stress concentrations and stress shielding as well as the risk of infection, in most cases, Ti-6Al-4V fixation hardware is not removed following the healing period. However, following engraftment or many types of trauma repairs, deeply placed fixation hardware is needed (Boyd, T. G., et al., "*CASE REPORT Removal of Exposed Titanium Reconstruction Plate After Mandibular Reconstruction With a Free Fibula Osteocutaneous Flap With Large Surgical Pin Cutters: A Case Report and Literature Review*," Eplasty, 12 (2012)).

The design of most of these devices has evolved into a form that both immobilizes and carries the least risk if it is not removed. Rarely do these fixation devices permit normal stress-strain trajectories to recur once healing has occurred. In order to reduce the risk of implant failure, it may be possible to affect more of a compromise between the needs of healing fixation and subsequent musculoskeletal function. Sufficient strength is needed for complete immobilization that allows healthy and full union of remaining and grafted bone followed by stress distributed between the hardware and newly fused bone in a normal pattern as the patient attempts full function (e.g., full power chewing) (Andani, M. T., et al., "*Metals for bone implants. Part* 1. *Powder metallurgy and implant rendering*," Acta Biomaterialia, 10:4058-70 (2014); Shayesteh Moghaddam, N., et al., "*Metals for Mandibular Implants, Part* 2: *Safety, Design, and Efficacy*," (in revision)). There are two important factors which affect bone healing: I) compressive stress should be created at the interface between graft/host mandible to accelerate bone healing, and II) the magnitude of the gap distance between the graft and host mandible interfaces should not exceed 200-500 micron to let the interfaces fuse together and assure bone healing (Ganesh, V., et al., "*Biomechanics of bone-fracture fixation by stiffness-graded*

*plates in comparison with stainless-steel plates*," Biomedical Engineering Online, 4:46 (2005); Sun, Z., et al., "*Masticatory mechanics of a mandibular distraction osteogenesis site: interfragmentary micromovement*," Bone, 41 (2): 188-196 (2007)).

Solid NiTi is currently used for orthodontic braces and intravascular stent devices (Bidabadi, M. et al., "*Thermophoresis effect on volatile particle concentration in micro-organic dust flame*," Powder Technology, 217:69-76 (2012); Bravo, L., et al., "*NiTi superelastic orthodontic archwires with polyamide coating*," Journal of Materials Science: Materials in Medicine, 25 (2): 555-560 (2014); Deberg, L., et al., "*An SMA Passive Ankle Foot Orthosis: Design, Modeling, and Experimental Evaluation*," Smart Materials Research (2014); Andani, M. T., et al., "*Design, modeling and experimental evaluation of a minimally invasive cage for spinal fusion surgery utilizing superelastic Nitinol hinges*," Journal of Intelligent Material Systems and Structures, p. 1045389X14541499 (2014)). Solid NiTi reduces stiffness over Ti-6Al-4V by more than half (roughly 38.5 GPa versus 110 GPa, respectively).

Surface porosity has been added to monolithic (i.e., non-porous, solid) medical implants in order to improve anchorage to the bone (Kienapfel, H., et al., "*Implant fixation by bone ingrowth*," The Journal of Arthroplasty, 14 (3): 355-68 (1999); Urban, R. M., et al., "*The Bone-Implant Interface of Femoral Stems with Non-Circumferential Porous Coating. A Study of Specimens Retrieved at Autopsy**," The Journal of Bone & Joint Surgery, 78 (7): 1068-81 (1996)). These surface features result in minor, if not immeasurable, reduction of stiffness (ElSaghir H, Boehm H, Greiner-Perth R. Mini-open approach combined with percutaneous transarticular screw fixation for C1-C2 fusion. Neurosurg Rev. 2005; 28 (1): 59-63. Epub 2004 Dec. 15. doi: 10.1007/s10143-004-0358-1). In contrast, an implant with selectively distributed internal porosity can have significantly reduced stiffness (Wen C, Yamada Y, Shimojima K, Chino Y, Asahina T, Mabuchi M. Processing and mechanical properties of autogenous titanium implant materials. Journal of Materials Science: Materials in Medicine. 2002; 13 (4): 397-401; Wang X-h, Li J-s, Hu R, Kou H-c, Zhou L. Mechanical properties of porous titanium with different distributions of pore size. Transactions of Nonferrous Metals Society of China. 2013; 23 (8): 2317-22). Selective pore distribution is especially important in inert (i.e., non-resorbing) implants as the stiffness of porous materials can be altered and optimized by controlling pore size, distribution, and shape (Elahinia M, Hashemi M, Tabesh M, Bhaduri S. Manufacturing and processing of NiTi implants: A review. Progress in Materials Science. 2012; 57 (5): 911-46). Essentially, the stiffness of an implant can be adjusted by changes in its pore geometry (i.e., its internal and external surfaces) (Rahmanian, R., N. Shayesteh Moghaddama, C. Haberland, D. Dean, M. Miller, and M. Elahinia, *Load Bearing and Stiffness Tailored Nitinol Implants Produced by Additive Manufacturing in SPIE Smart Structures and Materials*. 2014, SPIE: San Diego, California). The use of additive manufacturing also allows for control of the internal porosity of an implant. The pores may be positioned at any depth within the patient-specific implant or implant's surface. The porosity volume and percentage may be controlled.

However, modifying the geometry of an implant cannot help with materials that are too structurally weak, i.e., unable to function under the normal anatomic stresses encountered by an anatomic area such as the bone area. The stiffness of a patient-specific implant can be reduced by increasing porosity to the point where only the implant only contains struts or strands. In other words, porosity can be viewed as a tool that goes from the smallest resolution of fabrication, i.e., microporosity, to the highest level of an implant or implant components geometry, or its topology. "Microporosity" can be defined as porous spaces that are too small to support the invasion and long term health of vascularized tissue. It is especially risky to have porous spaces in implants that are too small for vascularized tissue which brings the host's immune system with it, but nevertheless, are large enough and connected to spaces from which bacteria, viruses, interstitial fluid or serum, and inflammatory, carcinogenic, or other deleterious cytokines and enter. At the same time, topological structures, or "macroporosity," such as struts, plates, or other shapes that provide larger spaces for communication with surrounding tissue can pass through or around or which can support muscular attachments or pockets of fat may be helpful. Some very effective algorithms such as the Schwarz primitive or diamond of the Schoen Gyroid have been used to design pores. Instead of making these shapes hollow, we make the space outside the pores a space, and use the pore space as the solid element of our construct. The mathematical equations reflecting calculations for both the Schwarz primitive and Schoen Gyroid are shown below.

Calculations for the Schwarz Minimal Surface

The equation of the surface can be written to have the following form:

$$f(x, y, z) = \cos(2\pi x) + \cos(2\pi y) + \cos(2\pi z)$$

Figure 13:
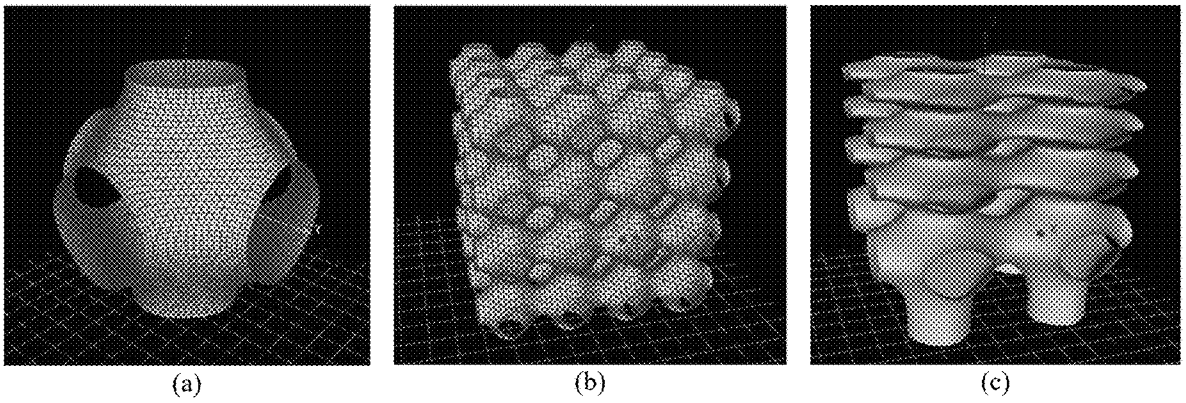
FIG. 13 illustrates a Minimal Schwarz Primitive (P) minimal surface (a) the unit cell of the surface (b) a cubic scaffold made by repeating the unit cell periodically in three directions (c) this surface can be designed to have different porosity along each direction (affine transformation), a scaffold which has varying porosity along z-direction.

With reference to FIG. 13, Minimal Schwarz Primitive (P) minimal surface (a) the unit cell of the surface (b) a cubic scaffold made by repeating the unit cell periodically in three directions (c) this surface can be designed to have different porosity along each direction (affine transformation), a scaffold which has varying porosity along z-direction shown.

The Schoen Gyroid minimal surface is determined as follows:

$$f(x, y, z) = \cos(2\pi x) * \sin(2\pi y) + \cos(2\pi y) * \sin(2\pi z) + \cos(2\pi z) * \sin(2\pi x)$$

Figure 14:
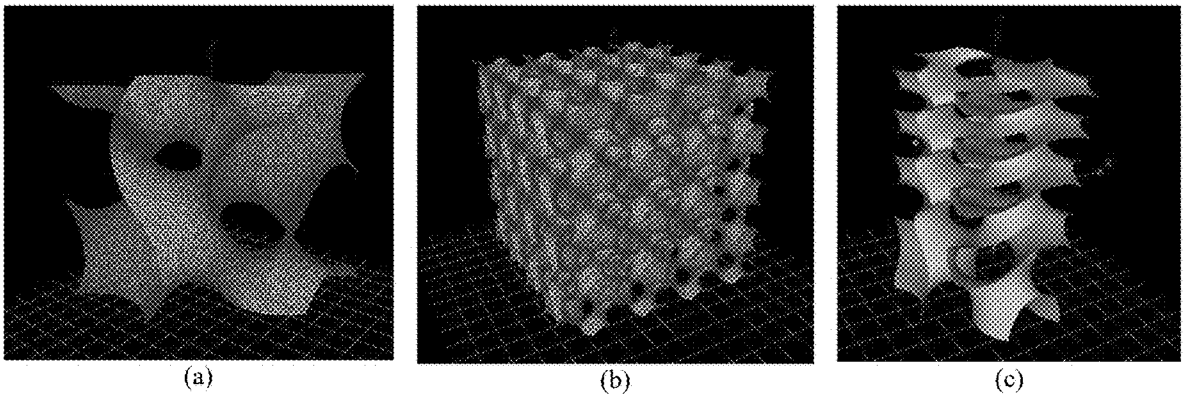
FIG. 14 illustrates a Minimal Schoen Gyroid (G) minimal surface (a) the unit cell of the surface (b) a cubic scaffold made by repeating the unit cell periodically in three directions (c) this surface can be designed to have different porosity along each direction (affine transformation), a scaffold which has varying porosity along z-direction.

With reference to FIG. 14, Minimal Schoen Gyroid (G) minimal surface (a) the unit cell of the surface (b) a cubic scaffold made by repeating the unit cell periodically in three directions (c) this surface can be designed to have different porosity along each direction (affine transformation), a scaffold which has varying porosity along z-direction shown.

The Schwarz Diamond minimal surface is determined as follows:

$$f(x, y, z) = \sin(2\pi x)\sin(2\pi y)\sin(2\pi z) + \sin(2\pi x\cos(2\pi y)\cos(2\pi z) + \cos)2\pi x)\sin(2\pi y)\cos(2\pi z) + \cos(2\pi x)\cos(2\pi y)\sin(2\pi x)$$

Figure 15:
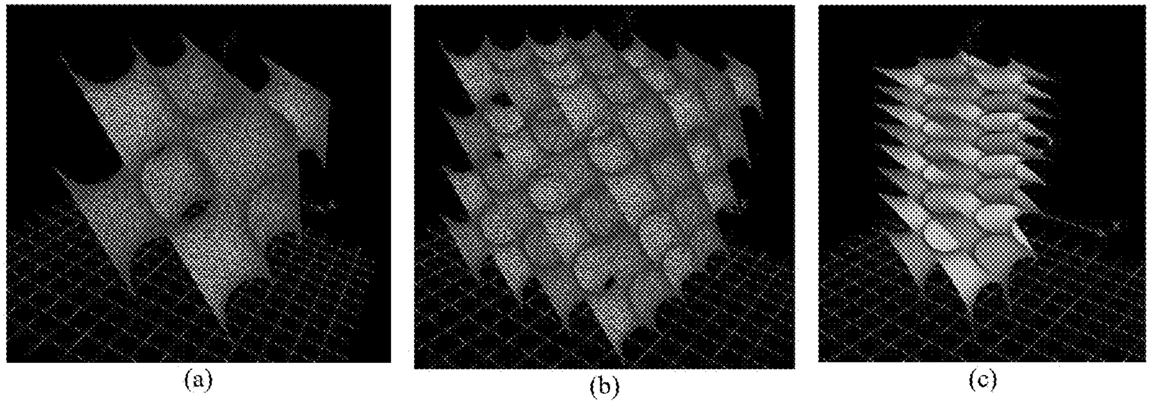
FIG. 15 illustrates a Minimal Schwarz Diamond (G) minimal surface (a) the unit cell of the surface (b) a cubic scaffold made by repeating the unit cell periodically in three directions (c) this surface can be designed to have different porosity along each direction, a scaffold which has varying porosity along z-direction.

With reference to FIG. 15, Minimal Schwarz Diamond (D) minimal surface (a) the unit cell of the surface (b) a cubic scaffold made by repeating the unit cell periodically in three directions (c) this surface can be designed to have different porosity along each direction, a scaffold which has varying porosity along z-direction shown.

In order to modulate the stiffness, it may be necessary to reduce the geometry of the object or patient-specific implant (i.e., skeletonize the object) to the key stress-strain trajectories. If we need to reduce stiffness further than by creating these struts, we will make the struts porous. Furthermore, it may be useful to have a gradient to that porosity to further tailor the stress strain trajectories and/or the areas where we want to achieve increased or decreased flexibility (i.e., taking advantage of the superelasticity properties of nitinol) (Sutradhar, A, Paulino, G. H., Miller, M. J., and Nguyen, T. H. Topological optimization for designing patient-specific large craniofacial segmental bone replacements PNAS, 107.30:13222-13227, doi: 10.1073/pnas. 1001208107 (2010)).

However, we use them to design these topological structures to control mechanical properties, especially to reduce stiffness. These porous architectures were not producible in materials such as NiTi or ceramics prior to the advent of Additive Manufacture (3D printing) (Rahmanian R, Shayesteh Moghaddam N, Haberland C, Dean D, Miller M, Elahinia M. Load Bearing and Stiffness Tailored NiTi Implants Produced by Additive Manufacturing: A Simulation Study. SPIE Smart Structures/NDE. Podium Presentation at SPIE Smart Structures/NDE, San Diego, CA. 2014; Jaemin Shin, Sungki Kim, Darae Jeong, Hyun Geun Lee, Dongsun Lee, Joong Yeon Lim, and Junseok Kim. Finite Element Analysis of Schwarz P Surface Pore Geometries for Tissue-Engineered Scaffolds. Mathematical Problems in Engineering: Volume 2012 (2012)).

Figure 16:
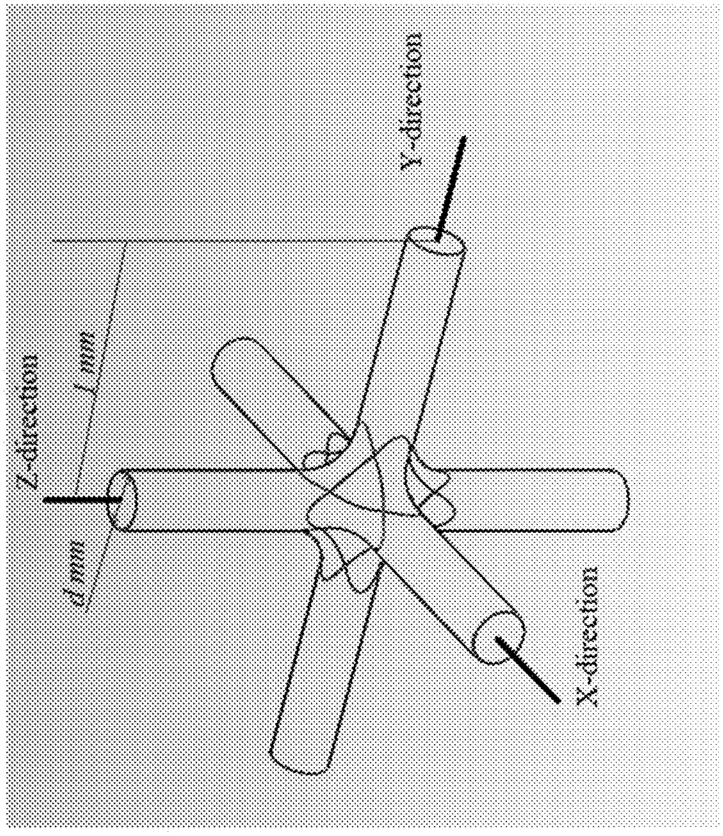
FIG. 16 illustrates a unit cell of the structure, having strands of d millimeters, and the result of its compressive deformation in a finite element study showing low stress concentration.
Figure 16:
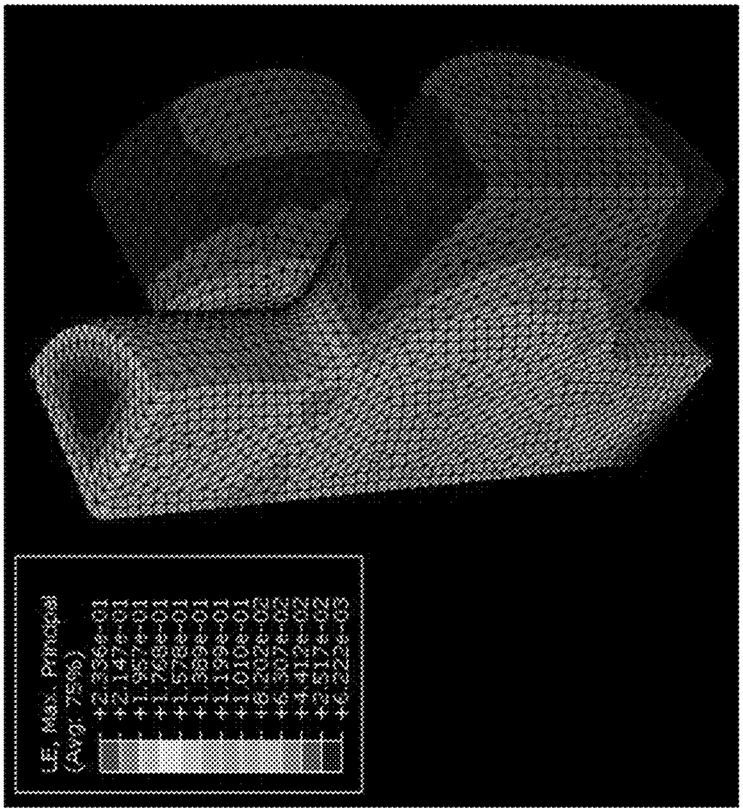

FIG. 16 shows a unit cell designed for AM that is repeated to form a porous implant. It should be noted that the example in FIG. 16 is a simple solution. It can be tuned by changing the length between intersections or the diameter of the strands. The Schwarz primitive and diamond and Schoen Gyroid algorithms allow for tuning the implant's Young's modulus.

Figure 17:
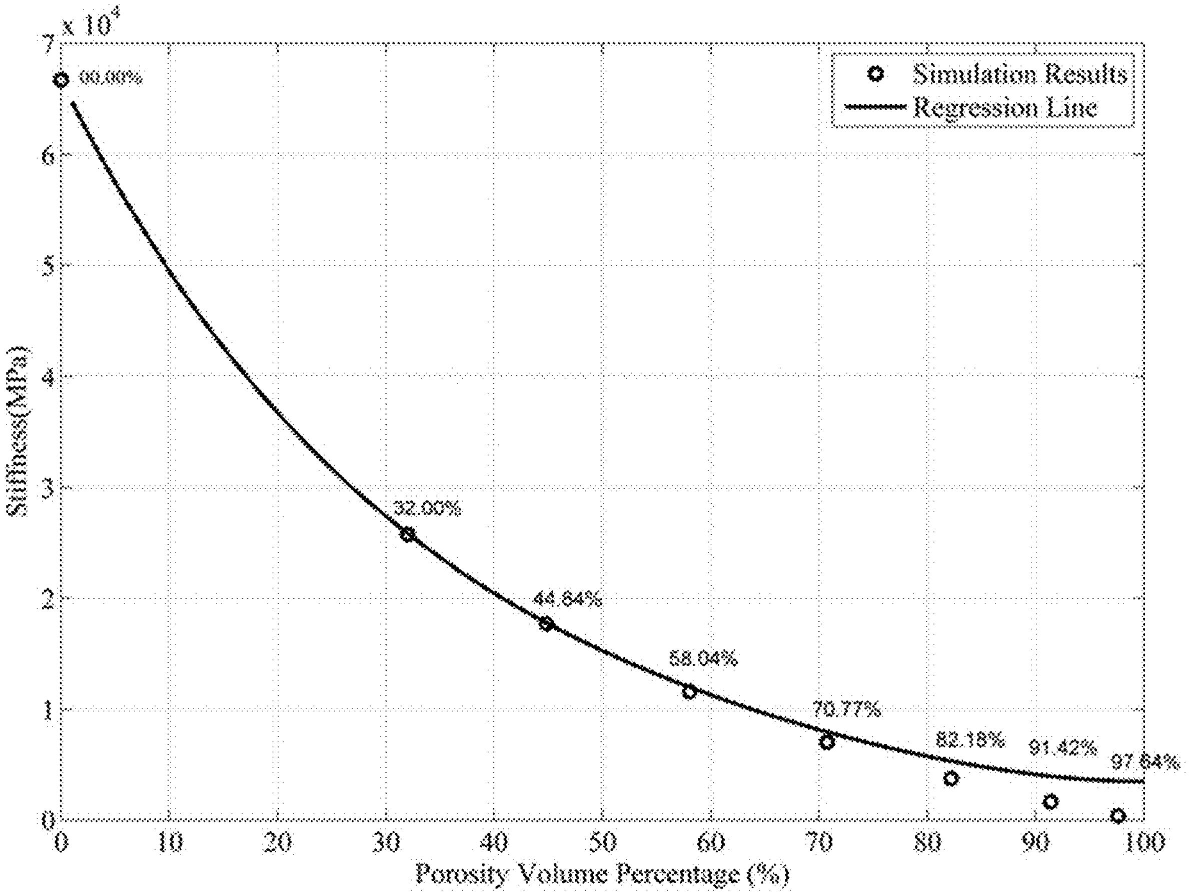
FIG. 17 is a graphical representation of stiffness of a nitinol structure reducing as the porosity volume percentage increases.

Based on a series of simulations, this unit cell exhibits minimal stress concentration. By repeating this unit cell in the desired regions of a patient-specific implant along the three directions, X, Y, and Z, an implant having desired mechanical properties can be achieved. It is worth noting that the geometry of the unit cell can changed to provide graded material properties in the patient-specific implant. In addition, by adjusting the porosity, it is possible to significantly modify the stress-strain behavior. In the elastic region, this variation in porosity leads to modifying the Young's modulus along the implant. The reduction in modulus as shown in FIG. 17 takes place as a result of adding porosity. If the material of choice has hysteretic behavior, such as NiTi, the porosity also leads to functional changes such as elimination of hysteresis.

The specific relationship of porosity to stiffness is shown below in Table 4.

TABLE 4

| Strand thickness (mm) | Porosity (volume percentage) | Stiffness (GPa) |
|---|---|---|
| 0.1 | 97.64 | 0.391 |
| 0.2 | 91.42 | 1.645 |
| 0.3 | 82.28 | 3.808 |
| 0.4 | 70.77 | 7.057 |
| 0.5 | 58.04 | 11.600 |
| 0.6 | 44.84 | 17.723 |
| 0.7 | 32.00 | 25.747 |
| Dense | 00.00 | 66.707 |

Thus, given (i) the stiffness in the x, y, and z-directions, using information such as shown in table 4 and the strand diameter in each direction and (ii) the ideal pore size, according to the needs of an osseointegrated implant as well as other bio-related properties, e.g., the unit cell size, the ideal porosity can be determined (Rahmanian, R., et al., "*Load Bearing and Stiffness Tailored Nitinol Implants Produced by Additive Manufacturing in SPIE Smart Structures and Materials*," SPIE: San Diego, California (Mar. 12, 2014)).

Just as porosity can be used at a microscopic level to reduce the stiffness of a bulk material it can be used to control its local elasticity. Moreover, gradients (affine or nonisotropic) applications of the Schwarz primitive or diamond or Schoen Gyroid algorithms, or other algorithms that can introduce regular distribution of porosity, can facilitate this channeling or local control of stiffness and elasticity. Going in the other direction, where it is best to reduce bulk stiffness by changing the overall geometry via topological optimization (i.e., reducing the size of the implant down to its key stress-strain trajectories). Those reduced elements can also have porosity imposed to further reduce stiffness.

Fabrication parameters can be controlled to modulate the material properties of the implant formed by varying the active process parameters such as laser power, scanning speed, scan track spacing etc. (Haberland, C., M. Elahinia, J. Walker, H. Meier, and J. Frenzel. Additive *Manufacturing Of Complex NiTi Shape Memory Devices And Pseudoelastic Components. in ASME Conference on Smart Materials, Adaptive Structures and Intelligent Systems,* 2013. Snowbird, Utah.: ASME; Haberland, C., J. Walker, M. Elahinia, and H. Meier. *Visions, Concepts And Strategies For Smart Nitinol Actuators And Complex Nitinol Structures Produced By Additive Manufacturing. In ASME* 2013 *Conference on Smart Materials, Adaptive Structures and Intelligent Systems.* 2013. Snowbird, Utah).

Figure 18:
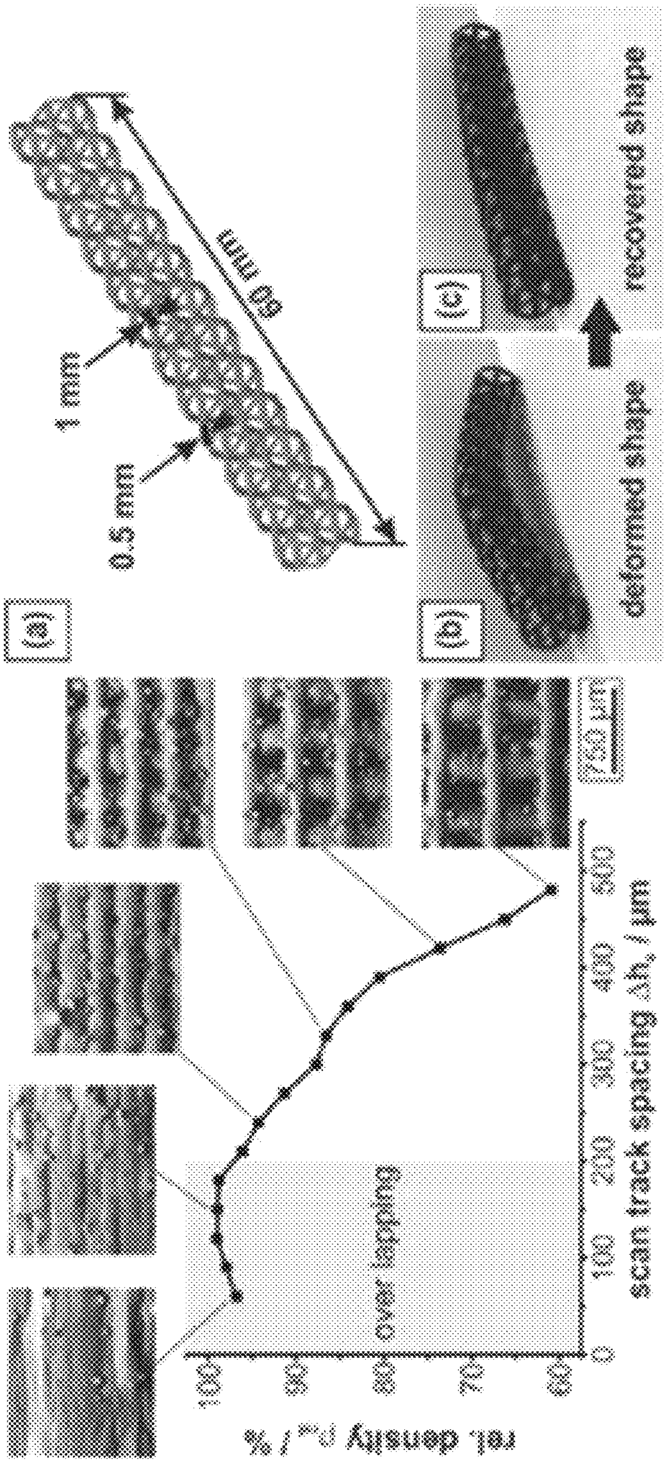
FIG. 18 illustrates engineered NiTi Parts with Defined Porosity: Manipulation of scan track developing fully dense materials or engineering porosity; cleated using SLM machine (Left) Complex NiTi structure with porous struts produced by AM: CAD model (a), structure exhibiting shape memory effect (b & c) (note, the size and shape of the strut" can be considered topological features).

Using this methodology, fabricating stiffness-tailored implants with porosity is possible in two main ways: (i) by creating the proper CAD file as shown in FIG. 18, or, (ii) by adjusting additional process parameters such as scan track spacing or offsets between central and boundary scan tracks (Sutradhar, A, Paulino, G. H., Miller, M. J., and Nguyen, T. H. Topological optimization for designing patient-specific large craniofacial segmental bone replacements *PNAS* 107.30:13222-13227, doi: 10.1073/pnas.1001208107 (2010)). Adjustment of the spacing is of primary importance for developing fully dense materials with ideal surface characteristics. Process parameters strongly affect density, chemical purity, surface morphology, mechanical properties, and phase transformation temperatures (Haberland, C., M. Elahinia, J. Walker, H. Meier, and J. Frenzel. *Additive Manufacturing Of Complex NiTi Shape Memory Devices And Pseudoelastic Components*. in *ASME Conference on Smart Materials, Adaptive Structures and Intelligent Systems.* 2013. Snowbird, Utah.: ASME; Haberland, C., J. Walker, M. Elahinia, and H. Meier. *Visions, Concepts And Strategies For Smart Nitinol Actuators And Complex Nitinol Structures Produced By Additive Manufacturing*. In *ASME* 2013 *Conference on Smart Materials, Adaptive Structures and Intelligent Systems.* 2013. Snowbird, Utah; Meier, H., C. Haberland, and J. Frenzel, *Structural and Functional Properties of NiTi Shape Memory Alloy Produced by Selective Laser Melting*. Innovative Developments in Design and Manufacturing: Advanced Research in Virtual and Rapid Prototyping, 2011: p. 291-296). Furthermore, mechanical properties of AM-NiTi are quite similar to conventional processed NiTi. Examples of fully dense SLM parts with optimal surface characteristics as well as parts with engineered porosity are shown in FIG. 18.

Figure 19:
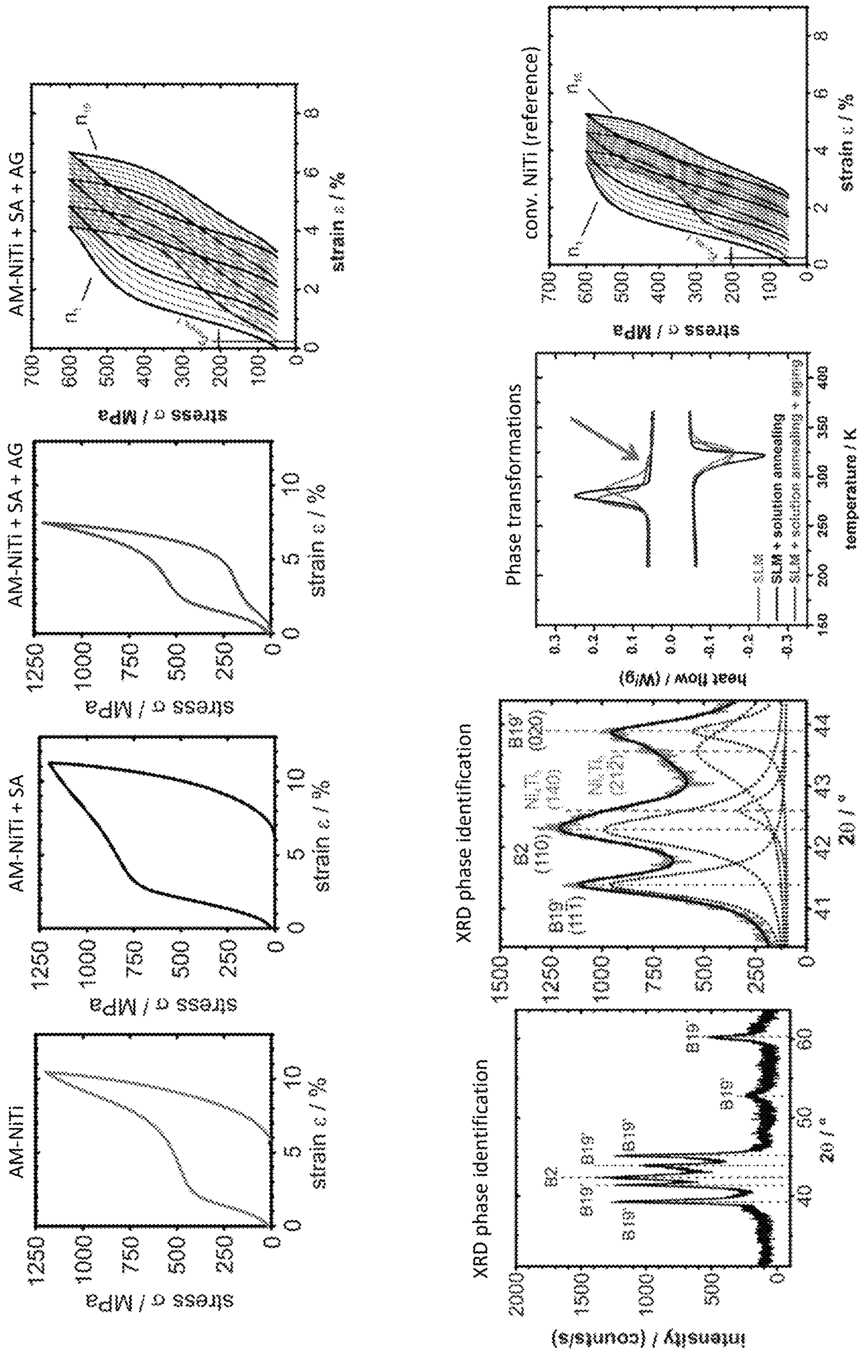
FIG. 19 illustrates superelasticity of AM manufactured NiTi Samples—Superelasticity of NiTi parts fabricated via AM and further heat-treated with solution annealing (SA) and aging (AG); AM fabricated parts show superelasticity similar to conventional NiTi.

It is also important to note that while increased scan track spacing typically corresponds to decreased density, very small scan track spacing can also result is decreased part density. FIG. 19 shows superelasticity of the AM manufactured NiTi samples and the effect of heat treatment on inducing this behavior. It is also important to note that while increased scan track spacing typically corresponds to decreased density, very small scan track spacing can also result is decreased part density. It is clearly visible that AM manufactured NiTi can show distinct superelasticity after heat treatments. The cyclic deformation behavior and the recoverable strains in AM manufactured NiTi can very well keep up with those in conventional manufactured NiTi.

In addition to stiffness matching and the ability to be 3D printed, nitinol presents a third property, superelasticity, which makes it useful for fixation devices and other bone implants such as joint replacement hardware. Nitinol is distinguished from conventional metallic materials by having tunable: shape memory, superelasticity, and stiffness properties. Shape memory has been used to encapsulate structures at low temperature and deploy them through catheters inside the body (e.g., stents). Shape memory properties are due to a martensitic phase transformation, a solid state crystallographic phase transformation between a high temperature phase (β—phase, austenite) and a low-temperature phase (α—phase, martensite). The transformation is diffusionless and therefore local concentration of the chemical composition is not affected; only the crystal structure changes. This change in crystal structure is driven by a shear process, which can be described by a coordinated, cooperative movement of the atoms in the crystal lattice. This transformation causes superelasticity, which is an important phenomenon for implants and is driven by an applied force.

Nitinol's superelasticity allows medical devices to restore their shape after relatively large deformations, provide shock absorption, and maintain the device's functional stability over the long term. NiTi also has good corrosion resistance and its biocompatible properties make this alloy an attractive candidate for various medical applications. NiTi is already in use for surgical tools, cardiovascular stents, and orthodontic wires (Duerig T, Pelton A, Stöckel D. An overview of nitinol medical applications. Materials Science and Engineering: A., 273:149-60 (1999); Machado L, Savi M. Medical applications of shape memory alloys. Brazilian Journal of Medical and Biological Research. 36 (6): 683-91 (2003); Morgan N. Medical shape memory alloy applications—the market and its products. Materials Science and Engineering: A. 378 (1): 16-23 (2004); Tarnită D, Tarnită D, Bîzdoacă N, Mîndrilă I, Vasilescu M. Properties and medical applications of shape memory alloys. Rom J Morphol Embryol., 50:15-21 (2009)). The relatively low stiffness of this alloy would be very useful for bone implants and for many applications in regenerative medicine. Nitinol's stiffness is tunable by introducing porosity at the microscopic level, through strut geometry design at the macroscopic level, or by design-integrating properties at both scale spaces (Andani M T, et al., "*Metals for Bone Implants, Part 1: Powder Metallurgy and Implant Rendering*," Acta Biomaterialia, 10:4058-70 (2014)).

The stiffness of the cortical (outer shell) region of the mandible is in the range of 17.6-31.2 GPa (Andani, M. T., et al., "*Metals for bone implants. Part 1. Powder metallurgy and implant rendering*," Acta Biomaterialia, 10:4058-70 (2014)). If useful, the stiffness of nitinol can be reduced to or below the level of cortical bone found anywhere in the skeleton through the introduction of porosity during alloying or topologically (i.e., the geometry of the device) during implant design (Shayesteh Moghaddam, N., et al., "*Metals for Mandibular Implants, Part 2: Safety, Design, and Efficacy*," (in revision)).

The methods and systems of the invention also allow for the design and fabrication of patient-specific surgical guides. Such patient specific surgical guides fit over an area of anatomy such as the bone and provide for guiding features such as bone drilling and/or cutting elements, in an pre-defined trajectory or direction into the bone (Tardieu, P. B., International Journal of Periodontics Restorative Dent. 27 (2): 141-149 (2007); Kunz, M. Proceedings of the 7th Annual Meeting of CAOS-International: 159-161 (2007); Lombardi, Jr., A. V., et al., BFA Orthopedics, 31:927 (2008)).

Patient-specific surgical guides in accordance with the present invention comprise one or more structures and/or guiding elements that are produced to fit uniquely to a portion of the patient's anatomy and guide the surgeon in locating a pre-planned segment for a graft and the insertion of that graft and/or a patient-specific implant at the defect site. Patient-specific implant fixation and/or graft immobilization hardware might also be planned and fabricated as tools in bringing about a desired functional outcome. The patient-specific implant may be designed to insure that the geometric and material properties of the anatomic area to be resected. For example, for a section of bone, the patient-specific surgical guide is be designed and fabricated to match the anatomy of the bone that is to be exposed and provide for unambiguous, guided drilling, cutting at the defect site or other manipulation such that the patient-specific implant properly seats in the resected area. The patient-specific surgical guides may be designed by identifying the shape and location of the defective portion of the patient anatomy in the outcome design software and then, using a template image produce a surgical guide that fits the patient specific implant as well as the defect site that will be accessed during surgery. U.S. Patent Application Publication No. 20120289965.

The patient-specific implant of the present invention may be combined with off-the-shelf implants and may integrate autologous, or allogeneic tissue or an alloplastic implant or implant components into the defect site.

The patient-specific implant can be coated with a matrix which has a nontoxic, biocompatible, bioerodible or biodegradable synthetic material. Or in the case of Ti-6Al-4V or NiTi, the surface is naturally oxidized producing an osseointegrating coating. The coating may further comprise one or more pharmaceutical substances (e.g., antibiotics) or drug (e.g., cytokines) compositions for delivering to the tissues adjacent to the site of implantation, and one or more ligands, such as a peptide, small and/or large molecules, and/or antibodies or combinations of any of the foregoing for capturing and immobilizing cells on the patient-specific implant. The matrix can be a controlled-release matrix having one or more polymers and/or oligomers from various types and sources, including, natural or synthetic polymers, which are biocompatible, biodegradable, bioabsorbable and are useful for controlled-released of a molecule such as a pharmaceutical compound. The polymeric materials include naturally occurring polymeric materials such as proteins including, collagen, fibrin, tropoelastin, elastin, cross-linked tropoelastin and extracellular matrix component, fibrin, fibronectin, laminin, derivatives or other biologic agents or mixtures. The matrix may comprise a synthetic material such as polyesters including, polylactic acid, polyglycolic acid or copolymers and or combinations thereof, a polyanhydride, polycaprolactone, polyhydroxybutyrate valerate, and other biodegradable polymer, or mixtures or copolymers thereof. In this embodiment, the matrix may comprise poly(lactide-coglycolide) as the matrix polymer for coating the medical device. For example, the poly(lactide-co-glycolide) composition may comprise at least one polymer of poly-DL-co-glycolide, poly(D,L-lactide-coglycolide) or copolymer or mixtures thereof, and it may be mixed together with the pharmaceutical substances to be delivered to the tissues. The coating composition may be applied to the surface of the patient-specific implant using standard techniques such as spraying, dipping, and/or chemical vaporization. Alternatively, the poly(lactide-coglycolide) (PGLA) solution can be applied as a single layer separating a layer or layers of the pharmaceutical substance(s).

Other alloys may be used with the methods and systems of the present invention. In certain embodiments, these alloys may be bioabsorbable. While several resorbable metals and alloys, such as iron have been studied, one of the best studied of these metals is Magnesium (Mg) (Liu, B., et al., "*Effects of alloying elements* (*Mn, Co, Al, W, Sn, B, C and S*) *on biodegradability and in vitro biocompatibility of pure iron*," Acta Biomaterialia, 7 (3): 1407-1420 (2011); Liu, L., et al., "*Corrosion behavior of Zr-based bulk metallic glasses in different artificial body fluids*," Journal of Alloys and Compounds, 425 (1): 268-273 (2006); Liu, L., et al., "*Bioactivation of Ni-free Zr-based bulk metallic glass by surface modification*," Intermetallics, 18 (10): 1978-1982 (2010); Li, H., et al., "*In vitro investigation of novel Ni free Zr-based bulk metallic glasses as potential biomaterials*," Materials Letters, 75:74-76 (2012)). This metal can be configured to form a strong implant that can be tuned to resorb via slow corrosion, not galvanism, following the expected bone wound healing process, a period that likely to be, at minimum, 3-6 months. The healing process can be tracked non-invasively via x-ray. If it is proceeding as expected, surgery to remove the resorbable fixation device will become unnecessary which reduces risk, discomfort, and cost for the patient. If the bone wound is not healing at the expected pace, a surgical intervention to place non-resorbing fixation hardware can be done.

There are many Mg alloys that have been shown to have controlled corrosion (degradation) rates in vivo (i.e., in the body), especially bone fixation. These alloy substances have often included rare earth elements (Hort, N., et al., "*Magnesium alloys as implant materials-Principles of property design for Mg-RE alloys*," Acta Biomaterialia, 6 (5): 1714-1725 (2010)). Other promising Mg alloys have included Sr (Mg—Sr degradation has been shown to result in hydroxyapatite formation—which could assist integration with host bone) (Bornapour, M., et al., "*Biocompatibility and biodegradability of Mg—Sr alloys: the formation of Sr-substituted hydroxyapatite*," Acta Biomaterialia (2012); Gu, X., et al., "*In vitro and in vivo studies on a Mg—Sr binary alloy system developed as a new kind of biodegradable metal*," Acta Biomaterialia, 8 (6): 2360-2374 (2012)). Mg—Zn—Zr alloys have been shown to have high strength and have been considered for load-bearing applications. (Velikokhatnyi, O. I., et al., "*First principles studies on alloying and simplified thermodynamic aqueous chemical stability of calcium-, zinc-, aluminum-, yttrium-and iron-doped magnesium alloys*," Acta Biomaterialia, 6 (5): 1698-1704 (2010)). Advantageous degradation and strength properties can be safely (non-toxic) obtained by inclusion of Zn, e.g., Mg—Sr—Zn and Mg—Nd—Zn—Zr, possibly smoothing the modulus gradient in a composite implant (Rosalbino, F., et al., "*Bio-corrosion characterization of Mg—Zn—X* (*X=Ca, Mn, Si*) *alloys for biomedical applications*," Journal of Materials Science: Materials in Medicine, 21 (4): 1091-1098 (2010); Zhang, X., et al., "*Effects of extrusion and heat treatment on the mechanical properties and biocorrosion behaviors of a Mg-Nd—Zn-Zr alloy*," Journal of the Mechanical Behavior of Biomedical Materials, 7:77-86 (2012); Zhang, X., et al., "*Biocorrosion properties of as-extruded Mg—Nd—Zn—Zr alloy compared with commercial AZ*31 *and WE*43 *alloys*," Materials Letters, 66 (1): 209-211 (2012); Zong, Y., et al., "*Comparison of biodegradable behaviors of AZ*31 *and Mg—Nd—Zn—Zr alloys in Hank's physiological solution*," Materials Science and Engineering: B, 177 (5): 395-401 (2012); Guan, R., et al., "*Development and Evaluation of a Magnesium-Zinc-Strontium Alloy for Biomedical Applications-Alloy Processing, Microstructure, Mechanical Properties, and Biodegradation*," Materials Science and Engineering: C, (2013)). Inclusion of Zn, i.e., Mg—Zn, strengthens the alloy, but quickens its degradation in combination with Sr while slowing degradation dramatically in Mg—Zn versus pure Mg (Brar, H. S., et al., "*Investigation of the mechanical and degradation properties of Mg-Sr and Mg—Zn—Sr alloys for use as potential biodegradable implant materials*," Journal of the Mechanical Behavior of Biomedical Materials, 7:87-95 (2012); Vojtech, D., et al., "*Mechanical and corrosion properties of newly developed biodegradable Znbased alloys for bone fixation*," Acta Biomaterialia, 7 (9): 3515-3522 (2011)). The in vitro degradation of Mg—Zn—Al has also been studied (Song, Y., et al., "*Biodegradable behaviors of AZ*31 *magnesium alloy in simulated body fluid*," Materials Science and Engineering: C, 29 (3): 1039-1045 (2009)). Mg—Zn—Ca alloys have been investigated for bone fracture fixation (Wang, H., et al., "In vivo degradation behavior of Ca-deficient hydroxyapatite coated Mg—Zn—Ca alloy for bone implant application," Colloids and Surfaces B: Biointerfaces, 88 (1): 254-259 (2011)). Hydroxyapatite has also been studied as a component in Mg alloys (Witte, F., et al., "*Biodegradable magnesium-hydroxyapatite metal matrix composites*," Biomaterials, 28 (13): 2163-2174 (2007)). Rare earth-containing alloys, such as Mg—Sc—Y, have also shown promise for use in bone fixation as they actively form a "self-passivating" layer of oxide on the surface (i.e., a more stable oxide than MgO), slowing the degradation rate enough to allow strong osteoblast (bone progenitor cell) attachment and proliferation (Johnson, I. and H. Liu, A Study on Factors Affecting the Degradation of Magnesium and a Magnesium-Yttrium Alloy for Biomedical Applications. PLOS ONE, 2013. 8 (6): p. e65603; Brar, H. S., J. P. Ball, I. S. Berglund, J. B. Allen, and M. V. Manuel, A study of biodegradable Mg-3Sc-3Y alloy and the effect of self-passivation on in-vitro degradation. Acta Biomaterialia, 2012). The co-implanting of Cr and O in Mg has been studied (Xu, R., G. Wu, X. Yang, T. Hu, Q. Lu, and P. K. Chu, Controllable degradation of biomedical magnesium by chromium and oxygen dual ion implantation. Materials Letters, 2011. 65 (14): p. 2171-2173). Bulk metallic glass alloys, such as Ca—Mg—Zn show good degradation and material properties, however the narrow range in which their high temperature formation occurs may make it difficult to use them for additive manufacturing technologies (Cao, J., N. Kirkland, K. Laws, N. Birbilis, and M. Ferry, Ca—Mg—Zn bulk metallic glasses as bioresorbable metals. Acta Biomaterialia, 2012. 8 (6): p. 2375-2383; Guo, S., Z. Liu, K. Chan, W. Chen, H. Zhang, J. Wang, and P. Yu, A plastic Ni-free Zr-based bulk metallic glass with high specific strength and good corrosion properties in simulated body fluid. Materials Letters, 2012. 84: p. 81-84; Huang, L., D. Qiao, B. A. Green, P. K. Liaw, J. Wang, S. Pang, and T. Zhang, Bio-corrosion study on zirconium-based bulk-metallic glasses. Intermetallics, 2009. 17 (4): p. 195-199; Huang, L., Z. Cao, H. Meyer, P. Liaw, E. Garlea, J. Dunlap, T. Zhang, and W. He, Responses of bone-forming cells on pre-immersed Zr-based bulk metallic glasses: effects of composition and roughness. Acta Biomaterialia, 7 (1): p. 395-405 (2011); Wang, J., S. Huang, Y. Wei, S. Guo, and P. Fusheng, Enhanced mechanical properties and corrosion resistance of a Mg—Zn—Ca bulk metallic glass composite by Fe particle addition. Materials Letters, 2012). Magnesium and its commonly available alloys such as AZ31 have been studied as craniofacial bone screws (Henderson, S. E., et al., "*Magnesium alloys as a biomaterial for degradable craniofacial screws*," Acta Biomaterialia (2013)). Iron-based alloys such as the Fe30Mn6Si shape memory alloy have also been investigated as potential degradable biomaterials for implants (Liu, B., et al., "*In vitro investigation of Fe30Mn6Si shape memory alloy as potential biodegradable metallic material*," Materials Letters, 65 (3): 540-543 (2011)), Iron-based alloys may have useful mechanical properties and will not produce hydrogen while degrading as has been seen in vivo with the galvanic deterioration of pure Mg. In recent rabbit model studies, an Mg—Ca—Zn alloy has shown good resorption properties when used as a bone implant (Cho, S. Y., et al., "*Biocompatibility and strength retention of biodegradable Mg—Ca—Zn alloy bone implants*." Journal Biomed Mater Res B Appl Biomater, 101 (2): 201-12 (2013)). Of the studied alloys Mg—Sr and Mg—Ca, and either of these with Zn, appear to have the most desirable properties as a biodegradable bone fixation device. MAO coatings of these implants have been shown to result in controlled degradation that would be favorable to the time frames, and strain transduction, needed for bone fixation devices. Fixation degradation and concomitant bone formation could be tracked non-invasively by x-ray, with an eye toward intervention if the process is not going as planned.

In this study, we explore the use of reduced-stiffness, porous nitinol fixation hardware as a substitute for Ti-6Al-4V in traditional bone fixation device geometries. Not only do we expect that stress concentration will be reduced in nitinol fixation plates and screws, more of the stress will be transferred to the graft once the patient is ready to chew forcefully and the grafted bone contains dental implants. We expect that allowing the grafted bone to undergo more force will facilitate its remodeling and strengthening (as opposed to resorbing). That process is expected to positively feedback into the restoration of more chewing power, all of which is expected to provide a healthier, long-term reconstruction that is, hopefully, more resistant to failure. In this experiment we determined that the compressive stress at the interface between grafted bone and the remaining host mandible is increased when porous nitinol hardware is used. We also determined that if the distance of the gap between the surfaces of the remaining host mandible and the grafted bone is limited to 500 micron or less. We explore the possibility of matching the stiffness of nitinol fixation hardware to the needs of a particular patient by adjusting the level and morphology of porosity.

1. Mandibular Segmental Defect Finite Element Model

Figure 20:
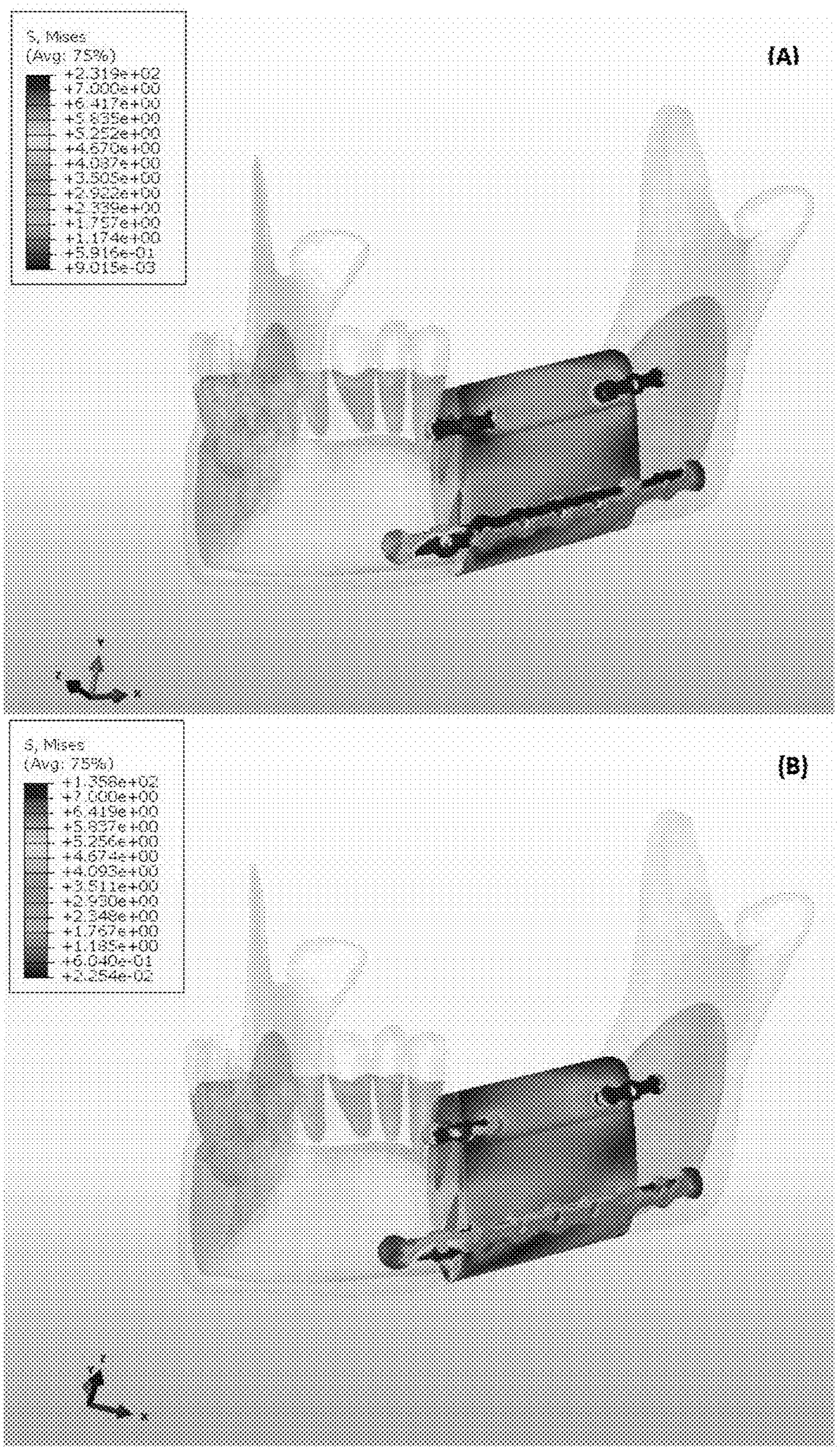
FIG. 20 illustrates stress distribution (von Mises): The cortical host bone has been made largely translucent. A) reconstructed mandible using Ti-6Al-4V fixation hardware and screws, and B) reconstructed mandible using stiffness-matched, porous nitinol fixation hardware and screws. The reduced stress seen by the superomesial and inferior fixation devices is consistent with re-establishing a normal superodistal to inferomesial stress-strain trajectory following reconstruction (Units: MPa).

A healthy adult mandible finite element model was created from a commercially obtained high resolution surface image data set (Journal of Craniofacial Surgery, draft manuscript) which includes highly accurate occlusal surfaces. It is noted that the Finite Element Analysis (FEA) from this data set was originally constructed in the project described above in Section I, and that it is used in this Section II to compare what happens with fixation hardware of different materials but not different geometries. CT data was used as a guide to create external and internal surfaces for cortical bone and cancellous bone layers. The periodontal ligament and dentin layers (within the teeth) are also simulated. Finally, the temporomandibular joint surface on the head of the mandible was simulated. A 40 mm segment of the left half of the mandible bearing $M_1$-3 was then virtually resected. A double fibular barrel graft and metallic fixation plates and screws have all been simulated in SolidWorks (Dassault Systèmes, Waltham, MA). The double fibular barrel graft is constituted from cutting an initially single piece of harvested fibular. The two pieces which are placed together in order to provide a total length of 40 mm and a buccolingual width of 14 mm. A single fixation plate is used to attach and immobilize the simulated lower fibular barrel graft at the base of the defect. That fixation plate is virtually bent so that it contacts the host and graft bone, immobilizing the graft. That fixation plate (FIG. 20) has nine threaded holes, a buccolingual thickness of 1.5 mm, a mesiodistal length of 78 mm, and a superoinferior width of 4 mm (Lovald, S. T., et al., "*Biomechanical optimization of bone plates used in rigid fixation of mandibular fractures*," Journal of Oral and Maxillofacial Surgery, 67 (5): 973-985 (2009)). One screw is inserted on each side of the mandible/graft junction both at the mesial and distal fibular graft/host mandible junctions. Bicortical screws with a diameter of 1.4 mm were simulated to fasten this inferior fixation plate. The upper fibular barrel is immobilized with two mini-plates which were created and graphically bent to be in contact (no gap) with both the graft and the host mandible immediately (i.e., as little gap as possible) superior to the lower fibular barrel graft. Each mini-plate has dimensions of 18 mm×2.8 mm×1 mm with three threaded holes (Lovald, S. T., et al., "*Biomechanical optimization of bone plates used in rigid fixation of mandibular fractures*," Journal of Oral and Maxillofacial Surgery, 67 (5): 973-985 (2009)). Unicortical screws with a diameter of 1.4 mm are simulated for the purpose of fastening these two mini-plates (Lovald, S. T., et al., "*Biomechanical optimization of bone plates used in rigid fixation of mandibular fractures*," Journal of Oral and Maxillofacial Surgery, 67 (5): 973-985 (2009)). All the components were assembled and imported to ABAQUS (Dassault Systèmes, Waltham, MA) for FEA during maximal mastication at the right $M_1$. The intersection between the teeth, periodontal ligament, and mandible are completely fixed. A 4-node linear tetrahedral mesh is used. The number of nodes is 323,630 and the number of elements is 1,536,782 for the whole reconstructed mandible and double fibular barrel grafts, fixation hardware, and fixation screws.

Material Properties and Boundary Conditions:

All material property data of our model components are from studies by Andani et al., Shetty et al., and Nagasao et al. as shown in Table 5 (Andani, M. T., et al., *Metals for bone implants. Part 1. Powder metallurgy and implant rendering*. Acta Biomaterialia, 10:4058-70 (2014); Shetty, P., et al., *A finite element analysis for a comparative evaluation of stress with two commonly used esthetic posts*. European Journal of Dentistry, 2013. 7 (4): p. 419; Nagasao, T., J. Miyamoto, and H. Kawana, *Biomechanical evaluation of implant placement in the reconstructed mandible*. The International journal of oral & maxillofacial implants, 2008. 24 (6): p. 999-1005).

TABLE 5

Material properties of the Finite Element Model components.

| Components | | Stiffness (MPa) | Poisson's ratio |
| --- | --- | --- | --- |
| Porous Nitinol | | 24,400 | 0.30 |
| Ti—6Al—4V | | 112,000 | 0.30 |
| Mandible | Cortical | 24,400 | 0.30 |
| | Cancellous | 3,000 | 0.30 |
| Fibular graft | Cortical | 26,800 | 0.30 |
| | Cancellous | 1,650 | 0.30 |
| Teeth | | 18,600 | 0.31 |
| Periodontal ligament | | 69 | 0.45 |

We simulated boundary conditions of maximum occlusion at the right $M_1$. The effect of the articular disc is ignored in this study and 24 nodes on the outer cortical surface of each mandibular condyle have been constrained to prevent movement in all directions. Seven nodes of bite contact on the buccal cusps of the right $M_1$ are restrained from movement in all directions away from centric occlusion, simulating the highest bite force during chewing. The total reaction force of seven bite nodes were confirmed to be 483 N which shows an 8% discrepancy with Korioth et al. (Korioth, T. W., et al., "*Three-dimensional finite element stress analysis of the dentate human mandible*," American Journal of Physical Anthropology, 88 (1): 69-96 (1992)). This discrepancy may be due to mandibular shape, inclusion of the periodontal ligament, and minor differences in the muscle attachment sites. Table 6 presents all muscle forces and directions pertaining to a bite force of 526 N at the right first molar maximum bite point (Korioth, T. W., et al., "*Three-dimensional finite element stress analysis of the dentate human mandible*," American Journal of Physical Anthropology, 88 (1): 69-96 (1992)).

TABLE 6

Muscle forces direction and magnitude. The X vector direction (right-left) is normal to the sagittal plane with the positive direction pointing toward the left side of the mandible. The Y vector direction (superoinferior) is normal to the occlusal plane with the positive direction pointing superiorly. The Z vector direction (anteroposterior) is orthogonal to the remaining two orthogonal axes. (Units: N = Newton, WS = working side BS = balancing side, and mm$^2$ = millimeter squared)

| Muscle group | | Muscle forces(N) WS | Muscle forces(N) BS | Muscle direction (WS/BS) | Area of attachment (mm$^2$) |
| --- | --- | --- | --- | --- | --- |
| Masseter | Superficial | 137.09 | 114.24 | ±0.207i + 0.995j + 0.419k | 10.31 ± 1.41 |
| | Deep | 58.75 | 48.96 | | |
| Pterygoid | Medial | 146.83 | 104.88 | ±0.486i + 0.791j + 0.372k | 6.00 ± 1.24 |
| Temporalis | Anterior | 115.34 | 91.64 | ±0.149i + 0.988j + 0.044k | 13.25 ± 3.3 |
| | Middle | 64.00 | 64.05 | | |
| | Posterior | 44.60 | 29.48 | | |

The muscle forces were obtained from Korioth et al. and the area of muscle attachment were obtained from Van Eijden et al. (Van Eijden, T., J. Korfage, and P. Brugman, *Architecture of the human jaw-closing and jaw-opening muscles*. The anatomical record, 1997. 248 (3): p. 464-474). The area of muscle attachment that they provide is from reported anatomical data (*Gray's Anatomy* (*Barnes & Noble Collectible Editions*)). Since it is known that chewing power decreases after mandibular reconstruction, all values in our simulations are 60% of the average value of healthy adults (Lovald, S. T., et al., "*Biomechanical optimization of bone plates used in rigid fixation of mandibular fractures*," Journal of Oral and Maxillofacial Surgery, 67 (5): 973-985 (2009)). All the muscles were restored to their normal location after the simulated surgical reconstruction.

2. Results

Porous Nitinol Fixation Hardware Versus Ti-6Al-4V Fixation Hardware

In order to facilitate bone healing, three factors may be important for fixation hardware. First, it is known that very stiff fixation hardware such as previously used stainless steel or cobalt-chromium devices caused problems following healing, including stress concentration within these metallic devices and stress shielding of grafted bone (Andani, M. T., et al., "*Metals for bone implants. Part* 1. *Powder metallurgy and implant rendering*," Acta Biomaterialia, 10:4058-70 (2014)). Second, strategic location of increased compressive stress, without an increase in displacement, at the interface between grafted bone and the remaining host mandible would accelerate both bone healing and subsequent bone remodeling (Ganesh, V., K. Ramakrishna, and D. N. Ghista, *Biomechanics of bone-fracture fixation by stiffness-graded plates in comparison with stainless-steel plates*. Biomedical Engineering Online, 4:46 (2005)). Third, in order to have the graft/host interface heal, the displacement between them must not exceed 200-300 micron during chewing (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46). This, in addition to the need for bone to remodel, is a good reason to delay placing dental implant posts in grafted bone until the graft/host junction has healed and is sufficiently rigid. Indeed, prior to our current studies we are aware of no attempt to use geometry and stiffness to design fixation hardware that would recreate the normal stress-strain trajectories associated with normal chewing.

Stress Concentration and Stress Shielding (Von Mises Stress Distribution)

One clinical complication associated with highly stiff Ti-6Al-4V fixation hardware is the loosening of screws and breaking of plates due to stress concentration (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46). In FIG. 20A we see the von Mises distribution in the mandible reconstructed with Ti-6Al-4V hardware and a double barrel fibular graft. In FIG. 20B we see the same reconstruction using nitinol fixation hardware. It can be seen that the von Mises stress has been reduced in the nitinol fixation devices and increased in the grafted bone. The maximum stress (FIG. 21) is seen to be reduced for nitinol compared to Ti-6Al-4V by factors of 2.8, 1.7, 2.2, and 1.4 for inferior fixation plate, superior distal fixation plate, superior mesial fixation plate and screws, respectively.

The porous nitinol hardware presents the highest stress concentration at the superior distal fixation plate. It is 135.8 MPa. We note that the nitinol hardware should be able to tolerate this amount of stress during peak chewing, and thereby maintain sufficient immobilization during the healing period. Studies have shown that in the austenite phase, solid nitinol has a yield strength of 200-800 MPa (Laschi, C., et al., "*Soft robotics: new perspectives for robot bodyware and control*," Bionics and Biomimetics, 2:3 (2014)). Although adding porosity reduces yield strength, we our model suggests that in this individual the design shown is in the safe region (Andani, M. T., et al., "*Metals for bone implants. Part* 1. *Powder metallurgy and implant rendering*," Acta Biomaterialia, 10:4058-70 (2014)). There are many benefits to stiffness-matching fixation devices to the individual.

Figure 21:
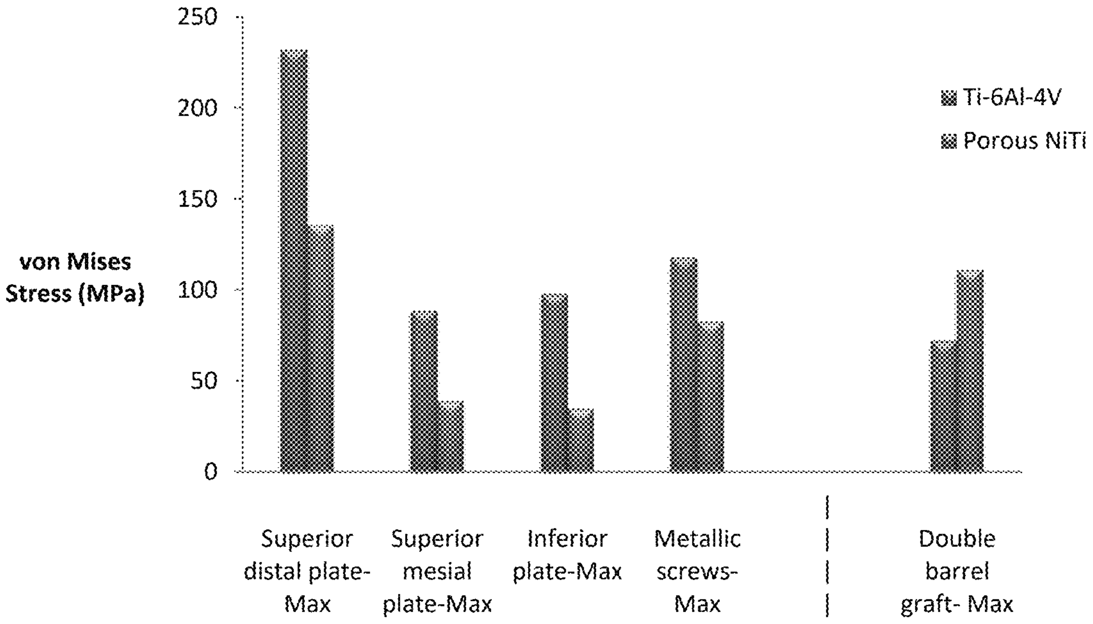
FIG. 21 illustrates a comparison of maximum von Mises stress among the superior distal plate, superior mesial plate, inferior plate, screws, and double barrel fibular graft between Ti-6Al-4V and porous nitinol fixation devices. Less stress concentration is seen in the porous nitinol fixation devices. More stress is delivered to the grafted bone when nitinol fixation devices are used (Units: MPa).

The high stress concentration in Ti-6Al-4V fixation plates and screws prevents loading of the grafted bone, thereby stress shielding that bone and the surrounding bone. Not having enough stress in the graft region can prevent remodeling of the grafted bone's cortical region, which will prevent full re-establishment of a normal stress-strain trajectory. Stress shielding is also likely to lead to long-term resorption, and/or dental implant failure (note: the addition of dental implants to the graft are not modeled here) (Puttlitz, C. M., V. K. Goel, and R. F. McLain, *Chapter* 137. *Biomechanics of Spinal Instrumentation.* 2001). It can be seen graphically in FIG. 20 that the reduced stress on metallic devices, with help of using porous nitinol, is transferred to the graft in the desired superodistal to inferomesial direction, between the coronoid process and the mental tubercles. FIG. 21 shows that the maximum von Mises stress on the graft is increased by the factor of 1.5 through the use of nitinol hardware. Channeling as much stress as possible to the graft is likely to increase remodeling activity of the grafted bone, reduce the risk of graft resorption and dental implant failure, and all of these are likely to improve the restoration of chewing power and overall long term oral health.

Compressive Stress at the Graft/Host Mandible Interface

Figure 22:
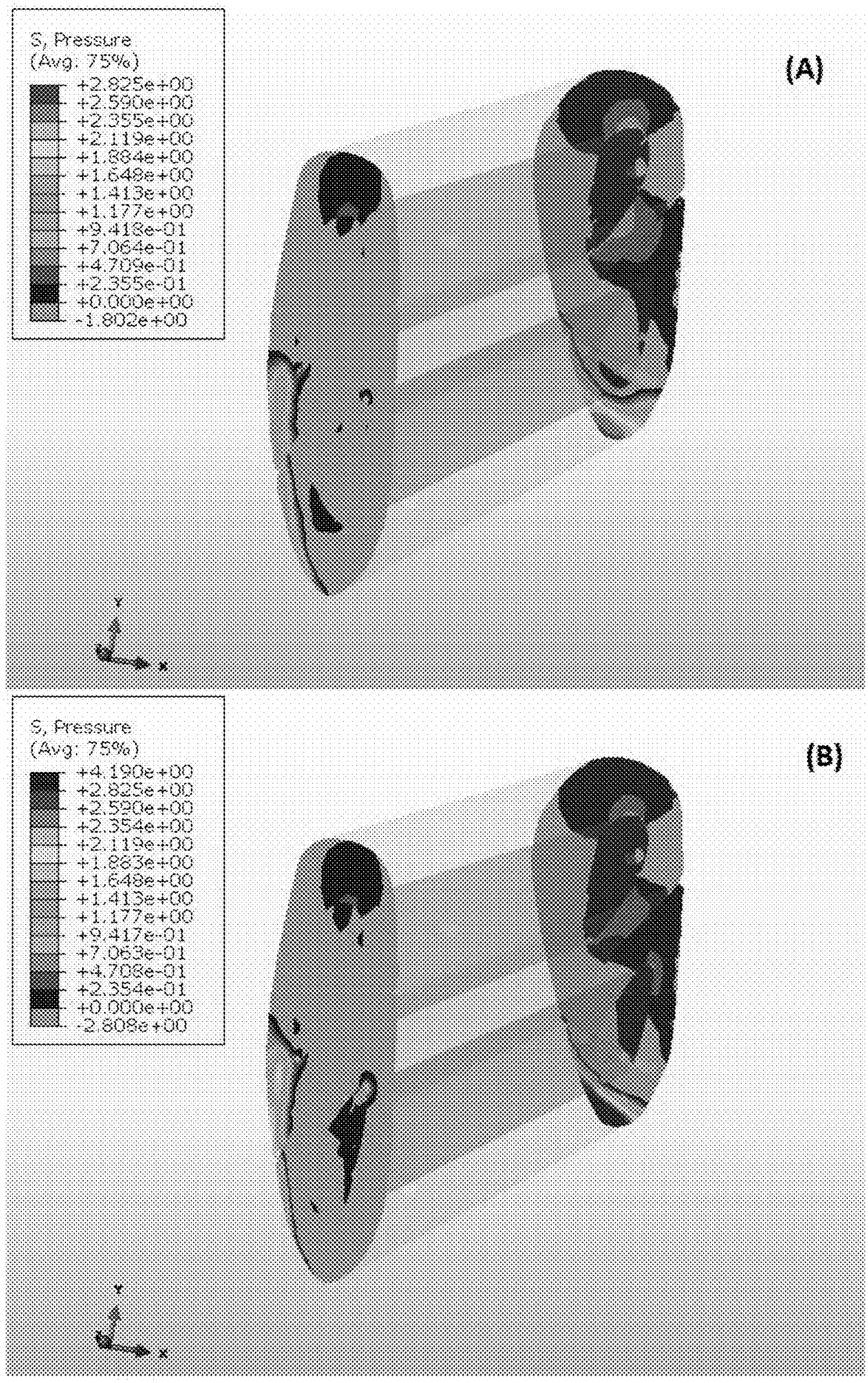
FIG. 22 illustrates compression stress at the interface between grafted bone/host mandible for a) mandible reconstruction using Ti-6Al-4V fixation devices, and b) mandible reconstruction using porous nitinol fixation devices. Area under tension is shown in gray. Compression values are shown as positive. Improved compression along the inferior edge of the lower fibular barrel graft may prevent resorption in this region which is not infrequently observed. (Units: MPa)

The purpose of fixation hardware is to hold the graft in position during healing, without allowing tensile stress at the interface between graft and host mandible. It would be helpful if compressive stress was located at this junction immediately after reconstructive surgery as it would accelerate grafted bone healing (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46). Compression and tension are defined to be hydrostatic pressure which is the third invariant of the element stresses. FIG. 22 demonstrates how the area under compression and the magnitude of compressive stress at the graft/host interface are increased when porous nitinol is substituted for Ti-6Al-4V fixation hardware of the same geometry. FIG. 22 shows the maximum value of compression and also the percentage area under compression, on both right and left interfaces of the graft, for the case of using porous nitinol versus Ti-6Al-4V. The percentage area under compression increased from 20.61% to 22.45% for the mesial graft/host interface, and from 54.63% to 55.2% for distal graft/host interface. In mesial graft/host interface a new area of compression at the anteroinferior region of the lower fibular graft. It is also seen that the magnitude of compression in the posteroinferior region of the graft/host interface is increased by a factor of 1.28 and by a factor of 1.49 at the inferoposterior region of lower fibular graft. The superodistal to anteroinferior direction of this increased pressure is consistent with the normal stress-strain trajectory that runs from the coronoid process to the mental tubercle. Re-establishment of these forces should facilitate both healing and remodeling.

The magnitude of tensile stress is also increased with nitinol versus Ti-6Al-4V fixation devices. While it is may seem that an increase of tensile stress at the graft/host interface might prevent healing, tension at this interface does not play important role in bone healing, regardless of the magnitude (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46). In general, tensile stress can play a role in stimulating bone remodeling and therefore bone strengthening (Ramakrishna, K., et al., *Design of fracture fixation plate for necessary and sufficient bone stress shielding*. JSME International Journal Series C, 2004. 47 (4): p. 1086-1094). However, as discussed in the next section, healing of a segmental defect can be disrupted by small displacements.

Allowed Gap for Bone Healing

Figure 23:
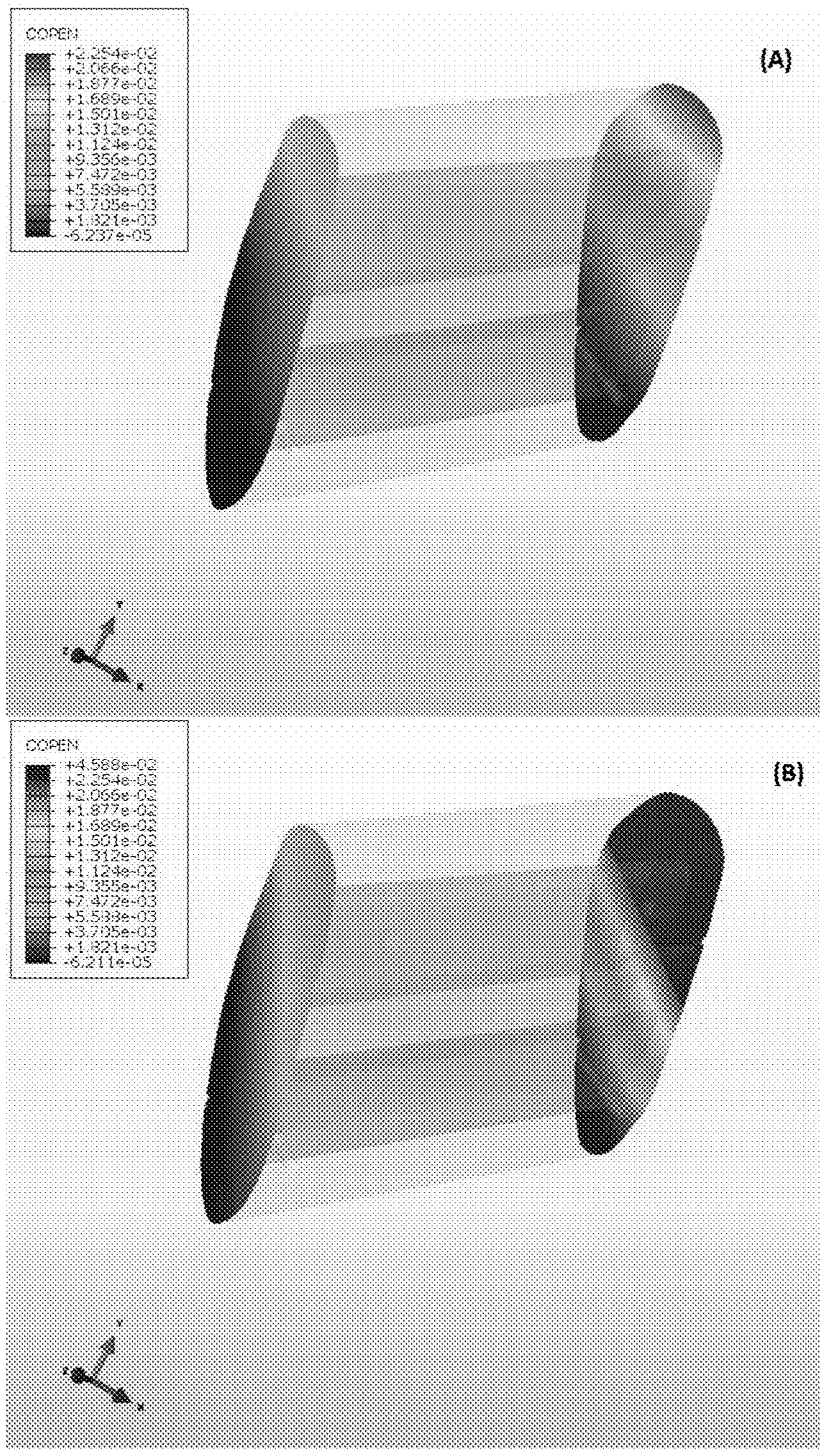
FIG. 23 illustrates a deformation map for the graft/mandible junction for a) reconstructed mandible reconstruction by using Ti-6Al-4V fixation devices, and b) and reconstructed mandible reconstruction by using porous nitinol hardware fixation devices. The gap between the graft/host interface during maximum chewing force generation at the right molar. The maximum chewing force is reduced 60% in both cases. This level of force reduction is commonly observed following segmental defect repair. The deformation seen at this gap is less than 200-300 μm in both cases. The increased level of superodistal to inferomesial deformation in (b) is consistent with re-establishment of normal stress-strain trajectories (Units: mm).

Another purpose of using hardware fixation is to immobilize the graft/host bone interface such that the gap distance not exceed 300 microns during the most strenuous chewing. If that cannot be achieved, bone healing will not occur (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46). Although it is shown in FIG. 23 that the gap is increased after putting porous nitinol, the maximum value remains below 200-300 m, therefore bone healing is still assured.

Stiffness-Matched Porous Nitinol Fixation Devices

The designed porosity of 3D printed nitinol fixation devices can be tuned to result in a device with the required level of stiffness. In our study, unit cells of porous nitinol were 3D printed of 3 perpendicular bars, a geometry that is relevant to mandibular fixation hardware. The porosity was adjusted by changing the diameter of each bar (Rahmanian, R., et al., Load bearing and stiffness tailored NiTi implants produced by additive manufacturing: a simulation study, in *The International Society for Optical Engineering.* 2014: San Diego, California; Rahmanian, R., et al., *Modeling and Validation of Additively Manufactured Porous Nitinol Implants, in ASME Conference on Smart Materials, Adaptive Structures and Intelligent Systems* (*SMASIS*). 2014: Newport, RI; Ben Zineb, T. Modeling and Simulation of Medical Devices Undergoing Complex Thermo-Mechanical Loadings. in *The International Conference on Shape Memory and Superelastic Technologies* (*SMST*). 2013. ASM).

Figure 24:
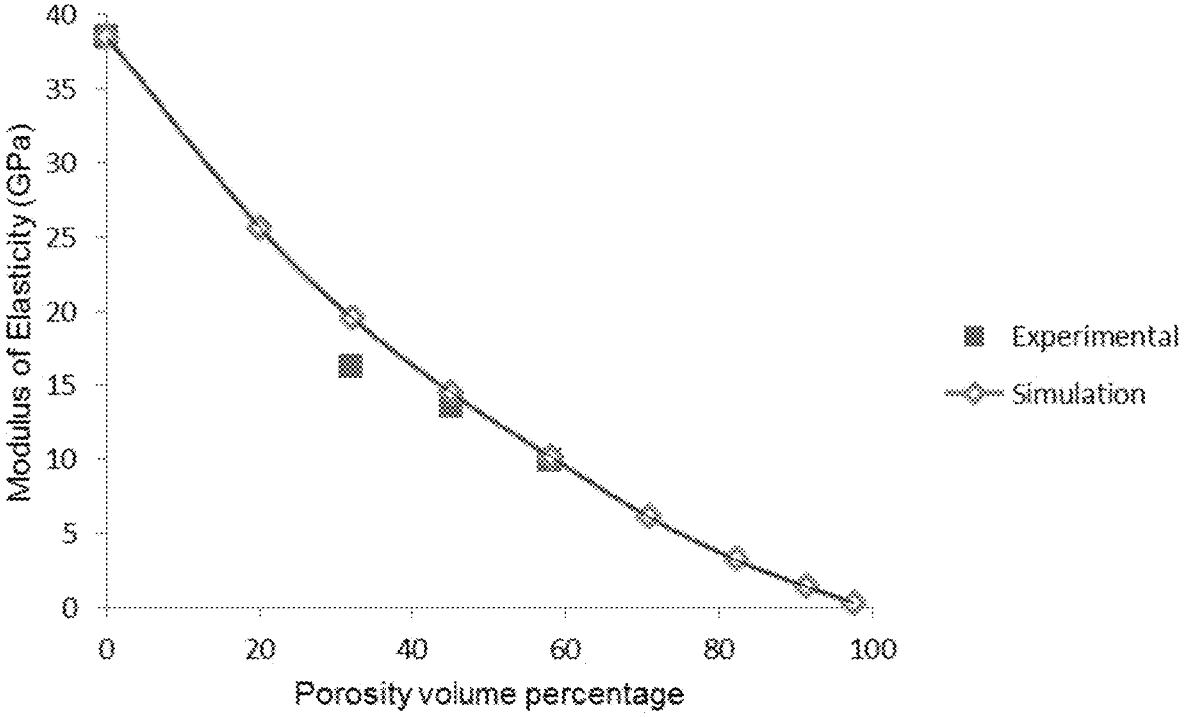
FIG. 24 illustrates an effect of increasing porosity on nitinol stiffness. Simulation and experimental data showing modulus versus porosity of nitinol fixation hardware with fixed geometry. The simulation was verified by using additive manufacturing to render and mechanically test three levels of porosity (Units: GPa).

In FIG. 24, the simulation data shows the effect of adding engineered porosity on stiffness. In order to validate this simulation (i.e., adding porosity to reduce stiffness), we SLM-fabricated three of each type of porous nitinol parts having porosity of 32%, 48.84%, 58.04% as well as three solid nitinol parts with the same dimensions. (Andani, M. T, et al., An Investigation of Effective Process Parameters on Phase Transformation Temperature of Nitinol Manufactured by Selective Laser Melting, in *ASME Conference on Smart Materials, Adaptive Structures and Intelligent Systems* (*SMASIS*). 2014: Newport, RI; Walker, J., et al., Additive Manufacturing of Nitinol Shape Memory Alloys to Overcome Challenges in Conventional Nitinol Fabrication, in *Proceedings of the International Mechanical Engineering Congress Exposition IMECE*2014. 2014: Montreal, Quebec, Canada). Since the experiment results, which are shown in red triangles, confirmed simulation results, we can simply predict the required porosity to be assigned to solid nitinol to reach the desired level of stiffness. Therefore, we found that by adding a porosity of 21.6% we can achieve a stiffness similar to that of cortical bone (24.4 GPa). Achieving a stiffness as close to mandibular cortical bone is a goal following healing but may not be during healing. That is because these fixation devices do not have the same geometry or location as the graft. It is also because the fixation devices must prevent more than 300 μm of displacement for at least six weeks during the healing process. Therefore, it is expected that the fixation devices need to be stiffer than the surrounding mandibular cortical bone.

3. Conclusion

The goal of "stiffness-matching" is to meet at least the following needs: (1) fixation during healing, (2) maximal reduction of fixation to that level based on the individual's anatomy and functional needs at the reconstructed site, (3) restoring the normal stress-strain trajectory.

As noted, Ti-6Al-4V is the current standard of care for fixation hardware material. These devices are often attached to a double fibular barrel graft. The high stiffness of fixation hardware both prevents load from traveling through the reconstructed mandible in the same trajectory as in the normal mandible and concentrates strain at specific locations in the fixation plates and screws. As mentioned, we are not aware of other workers who have attempted to match the stiffness and/or geometry of these fixation devices to initially immobilize reconstructed bone during post-operative healing and then subsequently restore the normal stress-strain trajectories of that bone during normal use.

As long as it is possible to maintain sufficient immobilization during the post-operative healing period, we suggest that it would be useful to attempt to have compressive stress at the interface between graft/host mandible to accelerate healing, while ensuring that on the graft/host gap distances not exceed 200-300 micron. In this way, we can expect that both bone healing and subsequent bone and chewing muscle strengthening will be optimized by the same device. The increased load on the graft would drive remodeling of the cortical bone, especially by fusing the region between the two fibular barrel grafts. That would result in a single outer cortical shell with optimal location of thickening (i.e., struts) that is better capable of carrying the normal stress-strain trajectory, especially after dental implants are placed in the grafted bone (not modeled here). This situation would also facilitate a maximum increase in power during chewing as the reconstructed bone strengthened. Finally, the overall long term stability of the reconstruction, rather than its failure or resorption, would be enhanced.

We suggest that the use of stiffness-matched porous nitinol as a substitute for Ti-6Al-4V can further reduce stiffness over both Ti-6Al-4V or bulk (dense) nitinol fixation devices. Based on our simulation studies, the level of porosity can be predicted for a particular stiffness. While we have only studied standard fixation locations and geometries here, it will likely be useful to look at new geometries range of stiffness-matching to what is needed for the stable, healthy surgical reconstruction of bony anatomy.

Section III: Two-Stage Mechanism—the Bone Bandaid

In order to support both the immobilization needed during healing and the distribution of strain through the engrafted bone once it has healed, we propose a novel approach to mandibular reconstruction treatment that has wide implications for musculoskeletal reconstruction throughout the body. During the 3-6 month healing period complete immobilization is needed, bringing mandibular micro-motion down to the level of 200-300 m, or less, during active chewing (Sun, Z., et al., "*Mandibular mechanics after osteotomy and distraction appliance placement I: Postoperative mobility of the osteotomy site*," Journal of Oral and Maxillofacial Surgery, 64 (4): 610-619 (2006); Sun, Z., et al., "*Masticatory mechanics of a mandibular distraction osteogenesis site: interfragmentary micromovement*," Bone, 41 (2): 188-196 (2007)). Current internal fixation systems accomplish this well compared to systems for wiring the teeth shut that were in use more than 30 years ago. However, once the engrafted bone is healed the stiff fixation hardware continues to alter the normal stress-strain trajectory of the bone during chewing (Rafferty K L, Sun Z, Egbert M A, Baird E E, Herring S W. Mandibular mechanics following osteotomy and appliance placement II: Bone strain on the body and condylar neck. J Oral Maxillofac Surg. 2006 April; 64 (4): 620-7). Current fixation hardware concentrates stress in the plates and especially at fixation screws. Problems requiring surgical interventions such as screws loosening or plate fractures occur and the abnormal stress-strain trajectory may take its toll on the surrounding bone. Over the long term, stiffly immobilized and stress-shielded bone grafts tend to resorb. Equally important is the permanent loss of chewing power owing to the revised stress-strain relationships. Power is seen to decline, on average 59% in the incisor region and 76% in the molar region (Maurer, P., H. Pistner, and J. Schubert. "Computergestützte Kaukraftanalyse bei Patienten mit Unterkieferkontinuitätsresektionen." Mund-, Kiefer-und Gesichtschirurgie 10, no. 1 (2006): 37-41; Wong, Raymond C W, Henk Tideman, Matthias A W Merkx, John Jansen, and Suk Ming Goh. "The modular endoprosthesis for mandibular body replacement. Part 2: Finite element analysis of endoprosthesis reconstruction of the mandible." Journal of Cranio-Maxillofacial Surgery 40, no. 8 (2012): e487-e497). Similar levels of power loss, of 40-50%, have been observed when standard Surgical Grade 5 titanium fixation hardware is not removed following fixation of traumatic mandibular fractures (Tate, Gregory S., Edward Ellis III, and Gaylord Throckmorton. "Bite forces in patients treated for mandibular angle fractures: implications for fixation recommendations." Journal of oral and maxillofacial surgery 52, no. 7 (1994): 734-736; Gerlach, K. L., and A. Schwarz. "Bite forces in patients after treatment of mandibular angle fractures with miniplate osteosynthesis according to Champy." International journal of oral and maxillofacial surgery 31, no. 4 (2002): 345-348).

Figure 25:
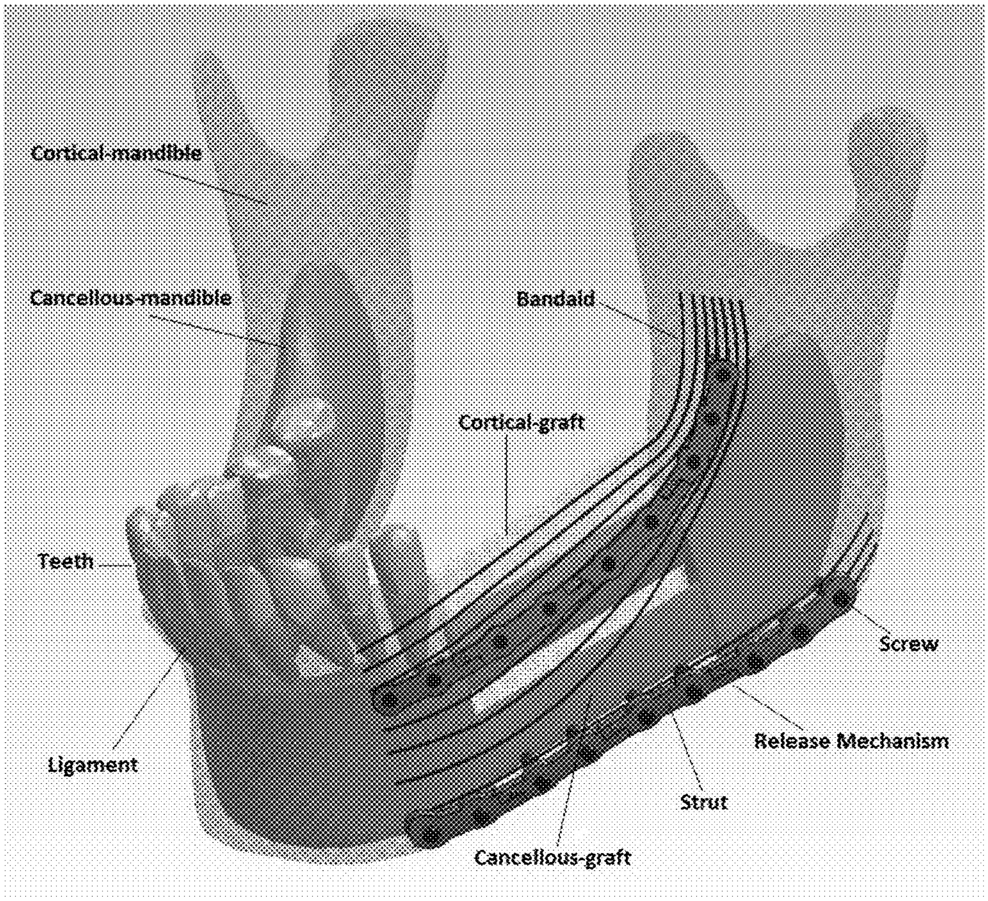
FIG. 25 illustrates components of the mandibular reconstruction using hardware and Bone Bandaid.

The competing needs of immobilizing and re-establishing normal stress-strain trajectories in grafted bone can be solved with a two-stage mechanism. As illustrated in FIG. 25, the two-stage mechanism includes use of (1) a releasable mechanism comprised of Ti-6Al-4V, which assures bone healing and is released once the reconstructed bony tissue and any of its ligamentous attachments have completely healed, and (2) a stiffness-matched nitinol wire-frame apparatus (referred to as the Bone Bandaid herein) which has the capability to recreate the normal stress/strain trajectories across (i.e., through) the engrafted bone after the healing period.

Figure 26:
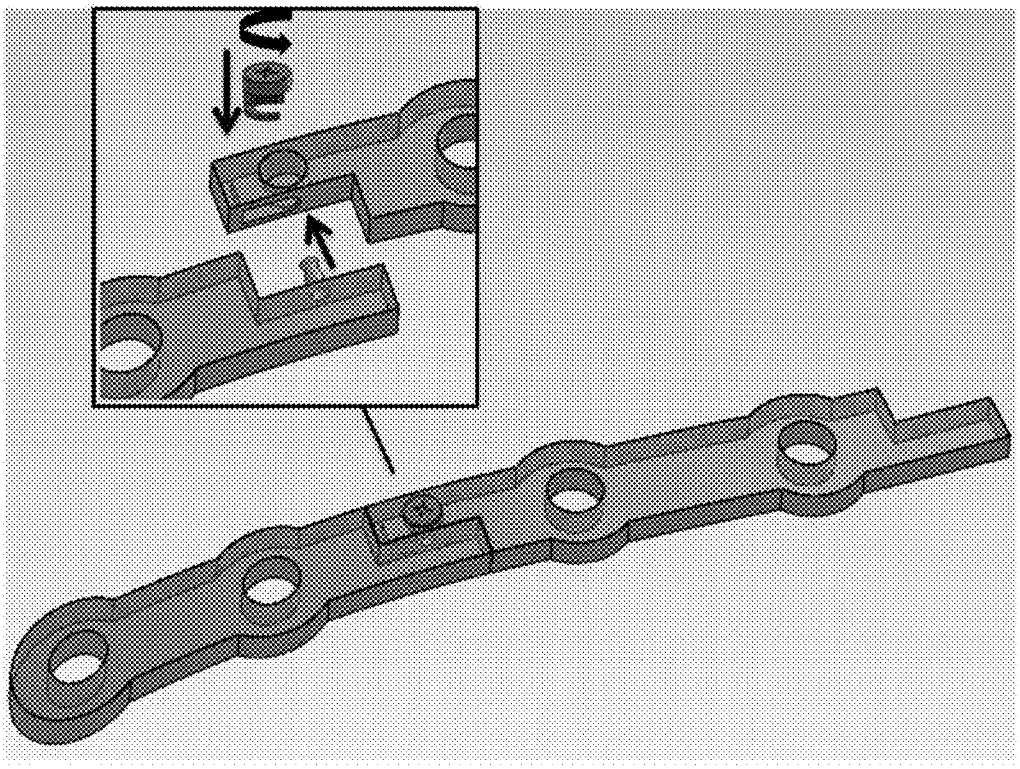
FIG. 26 illustrates a release mechanism for the fixation hardware associated with the Bone Bandaid illustrated in FIG. 25.

The releasable mechanism (or fixation hardware) is positioned external to the stiffness-matched nitinol wire-frame apparatus. These two entirely separate components work in sequence. The high stiff fixation hardware is needed to bring mandibular micro-motion down to the level of 200-400 μm during active chewing (Sun, Z., et al., "*Mandibular mechanics after osteotomy and distraction appliance placement I: Postoperative mobility of the osteotomy site*," Journal of Oral and Maxillofacial Surgery, 64 (4): 610-619 (2006); Sun, Z., et al., "*Masticatory mechanics of a mandibular distraction osteogenesis site: interfragmentary micromovement*," Bone, 41 (2): 188-196 (2007)). The nitinol frame has little effect until the Ti-6AL-4V component is "released". The release procedure would occur following radiological verification that the surgical osteotomies had been healed. The healing period often takes 6-9 months. The release procedure would occur under local anesthetic (FIG. 26). Alternatively, the release mechanism can be made from a resorbable material, such as a polymer, ceramic, or Mg-alloy, thereby completely mitigating the need for surgical procedure to bring about the release. If the highly stiff fixation hardware would not be released, it continues to alter the normal stress strain trajectory seen during chewing which is associated with concentrated stress in the plates and especially at fixation screws, and stress-shielded engrafted bone which tends to resorb. (Rafferty, K. L., et al., *Mandibular mechanics following osteotomy* and *appliance placement II: Bone* strain *on the body* and *condylar neck*. Journal of oral and maxillofacial surgery, 2006. 64 (4): p. 620-627). The power loss, of 40-50%, also can be seen among patients who have the hardware remaining in their body (Tate, G. S., E. Ellis III, and G. Throckmorton, *Bite forces in patients treated for mandibular angle fractures: implications for fixation recommendations*. Journal of oral and maxillofacial surgery, 1994. 52 (7): p. 734-736). With the fixation plates no longer functional, the barb-anchored, nitinol webbing of the Bone Bandaid acts as a superstructure, akin to skin, to the underlying grafted cortical bone. The Bone Bandaid is expected to facilitate the transduction of strain and thereby create a normal stress-strain trajectory, allow restoration of power and driving cortical bone remodeling and strengthening, provide long term strength, and a good bone bed for dental implants (Shayesteh Moghaddam, N., et al., "*Metals for Mandibular Implants, Part 2: Safety, Design, and Efficacy*," (in revision)). Normative strain patterns would allow restoration of chewing power and drive cortical bone strengthening and remodeling that would result in good bone stock for dental implants. The Bone Bandaid can also serve as a failsafe in cases of modest trauma, preventing disintegration and disruption of the surgically reconstructed site.

This two-stage mechanism is promising due to at least the following reasons: reduced stress concentration on screws/hardware; increased stress on the graft which helps prevent resorption, and makes the graft stronger, hopefully strong enough to support a dental implant (Hohlweg-Majert, B., et al., "*Significance of osteoporosis in craniomaxillofacial surgery: A review of the literature*," Osteoporosis International, 17 (2): 167-179 (2006)); increased compressive stress (magnitude and area under compression) at the interface between the graft/mandible; the gap distance at interfaces in the safe range (under 200-400 micron) for bone healing (Sun, Z., et al., "*Mandibular mechanics after osteotomy and distraction appliance placement I: Postoperative mobility of the osteotomy site*," Journal of Oral and Maxillofacial Surgery, 64 (4): 610-619 (2006); Sun, Z., et al., "*Masticatory mechanics of a mandibular distraction osteogenesis site: interfragmentary micromovement*," Bone, 41 (2): 188-196 (2007)).

The resulting patient-specific stress/strain pattern determined via Finite Element Analysis (FEA) confirms a better immobilization for the engrafted bone to be healed, and a stress/strain distribution under normal chewing through the bone after healing period. Our comparison in the first stage is based on the results obtained by utilizing currently used Ti-6Al-4V fixation hardware(s) under 60% of normal chewing, and in the second stage it is based on the results obtained by using healthy mandible under normal chewing.

1. Mandibular Segmental Defect Finite Element Model

The healthy adult mandible CAD file was created from a commercially obtained high resolution surface image data set. External and internal surfaces of cortical and cancellous bone was created using CT data. Periodontal ligament and teeth were simulated as well. A resection of 40 mm was created on the left half of the mandible bearing $M_{1-3}$. All the hardware, screws, wires, and double barrel graft were simulated virtually in SolidWorks (Dassault Systèmes, Waltham, MA) (see Figure. 25). The double barrel graft is made out of two single allografts with a total length of 40 mm and width of 14 mm to fill the resected site. The wire frame apparatus includes 11 wires with diameter of 0.6 which are bent graphically to lay on the graft and surrounding mandible bone. The wires are hooked with barbs designed to hold onto the graft and surrounding host bone. The fixation device has nine threaded holes and has the dimensions of 77 mm×6.4 mm×2 mm. The fixation hardware is bent virtually to be placed on the bone as it happens in real surgery. Bicortical screws with a diameter of 2.5 mm are considered to secure the upper and lower fixation hardware to the surrounding mandible and graft. The upper and lower fixation hardware each include four plates which are connected together with releasable CAM screws such that to release the fixation once healing is completed (see FIG. 26). The release mechanism has two components, cam lock and cam nut. The end of one plate is equipped with the cam lock, and the end of another plate includes a recess for the cam lock to be placed inside and a hole which is located for the cam nut to be fitted inside by twisting is a counterclockwise direction until it is locked. Two plates can be disengaged at the desired time by twisting the cam nut clockwise, so the cam lock can slide in the sleeve on the other plate freely and the two plates would release apart without any revision surgery. The cam screw has a diameter of 0.5 mm. All the components were assembled and imported to ABAQUS (Dassault Systèmes, Waltham, MA) for Finite Element Analysis during the right $M_1$ chewing. A 4-node linear tetrahedral mesh in ABAQUS is used. The number of nodes is 367,425 and the number of elements is 1,680,602 for the whole reconstructed mandible and double fibular barrel grafts, fixation hardware, fixation screws, and wires.

The material properties of our components were taken from studies by Andani et al., Shetty et al., and Nagasao et al which is shown in table 7 (Andani, M. T., et al., "*Metals for bone implants. Part* 1. *Powder metallurgy and implant rendering*," Acta Biomaterialia, 10:4058-70 (2014); Shetty, P., et al., "*A finite element analysis for a comparative evaluation of stress with two commonly used esthetic posts*,"

European Journal of Dentistry, 7 (4): 419 (2013); Nagasao, T., et al., "*Biomechanical evaluation of implant placement in the reconstructed mandible*," The International Journal of Oral and Maxillofacial Implants, 24 (6): 999-1005 (2008)).

TABLE 7

Material properties of the Finite Element Model components.

| Model components | Stiffness (MPa)/Poisson's ratio |
|---|---|
| Dense NiTi | 48,000/0.30 |
| Ti—6Al—4V | 112,000/0.30 |
| Cortical mandible | 24,400/0.30 |
| Cancellous mandible | 3,000/0.30 |
| Cortical graft | 26800/0.30 |
| Cancellous graft | 1,650/0.30 |
| Teeth | 18,600/0.31 |
| Periodontal ligament | 69/0.45 |

The breakthrough element of this model is the baseline data provided by the Korioth et al. group which allows us to predict the force created by the masticatory muscles based on the maximum cross-sectional area of masseter, temporalis, and medial pterygoid. Muscle directions are provided by the Van Eijden et al. (Van Eijden, T., et al., "*Architecture of the human jaw-closing and jaw-opening muscles*," The Anatomical Record, 248 (3): 464-474 (1997)) and the areas of attachment are taken from anatomy data (*Gray's Anatomy* (*Barnes & Noble Collectible Editions*)). In order to obtain the specific equivalent bite load, a simulation is carried out where the biting motion is constrained in seven nodes on the buccal cusps of the lower right first molar against moving in all directions and the muscle loads are gradually and proportionally increased as the reaction force matches the bite force required to chew. Twenty-four nodes on each tempromandibular joints were restrained from moving in all directions (the effect of articular disc is ignored) (Korioth, T. W., et al., "*Three-dimensional finite element stress analysis of the dentate human mandible*," American Journal of Physical Anthropology, 88 (1): 69-96 (1992); Lovald, S. T., et al., "*Biomechanical optimization of bone plates used in rigid fixation of mandibular fractures*," Journal of Oral and Maxillofacial Surgery, 67 (5): 973-985 (2009)).

It should be noted that the intersection between teeth/periodontal ligament, periodontal ligament/cortical mandible, cortical mandible/cancellous mandible are completely tied together.

2. Results

We are aware of no attempt to design mandibular fixation hardware that can restore normal chewing stress-strain trajectories and chewing power, while keep an eye on immobilization to assure bone healing. Stage I (locked state) which assures bone healing to be completed was compared with the most recent standard of care for reconstruction, the use of Ti-6Al-4V hardware(s) and fibula double barrel graft. Stage II (released state) which is responsible for creating normal stress/strain distribution was compared with the normal chewing for healthy mandible.

The Locked State

There are three factors which are important for the reconstructed mandible during the healing period. First, low stress concentration on the hardware (Andani, M. T., et al., "*Metals for bone implants. Part* 1. *Powder metallurgy and implant rendering*," Acta Biomaterialia, 10:4058-70 (2014)). Second, maximum gap distance in the interface between engrafted bone/and host mandible less than 200-400 micron (Sun, Z., et al., "*Mandibular mechanics after osteotomy and distraction appliance placement I: Postoperative mobility of the osteotomy site*," Journal of Oral and Maxillofacial Surgery, 64 (4): 610-619 (2006); Sun, Z., et al., "*Masticatory mechanics of a mandibular distraction osteogenesis site: interfragmentary micromovement*," Bone, 41 (2): 188-196 (2007)). Third, more compressive stress in the interface between graft and mandible (Ganesh, V., K. Ramakrishna, and D. N. Ghista, *Biomechanics of bone-fracture fixation by stiffness-graded plates in comparison with stainless-steel plates*. Biomed Eng Online, 2005. 4: p. 46).

Stress Concentration

The maximum von Mises stress on the Ti-6Al-4V hardware was reduced in stiffness-matched nitinol hardware with the same shape for the suggested structure compare to using standard of care hardware as follow: For upper hardware(s), from 232.4 MPa to 110 MPA; for lower hardware 112 MPa to 57 MPa. The maximum von Mises stress on the nitinol wires are 72 MPa, which is less than yield strength of nitinol.

Minimized Gap for Bone Healing

Figure 27:
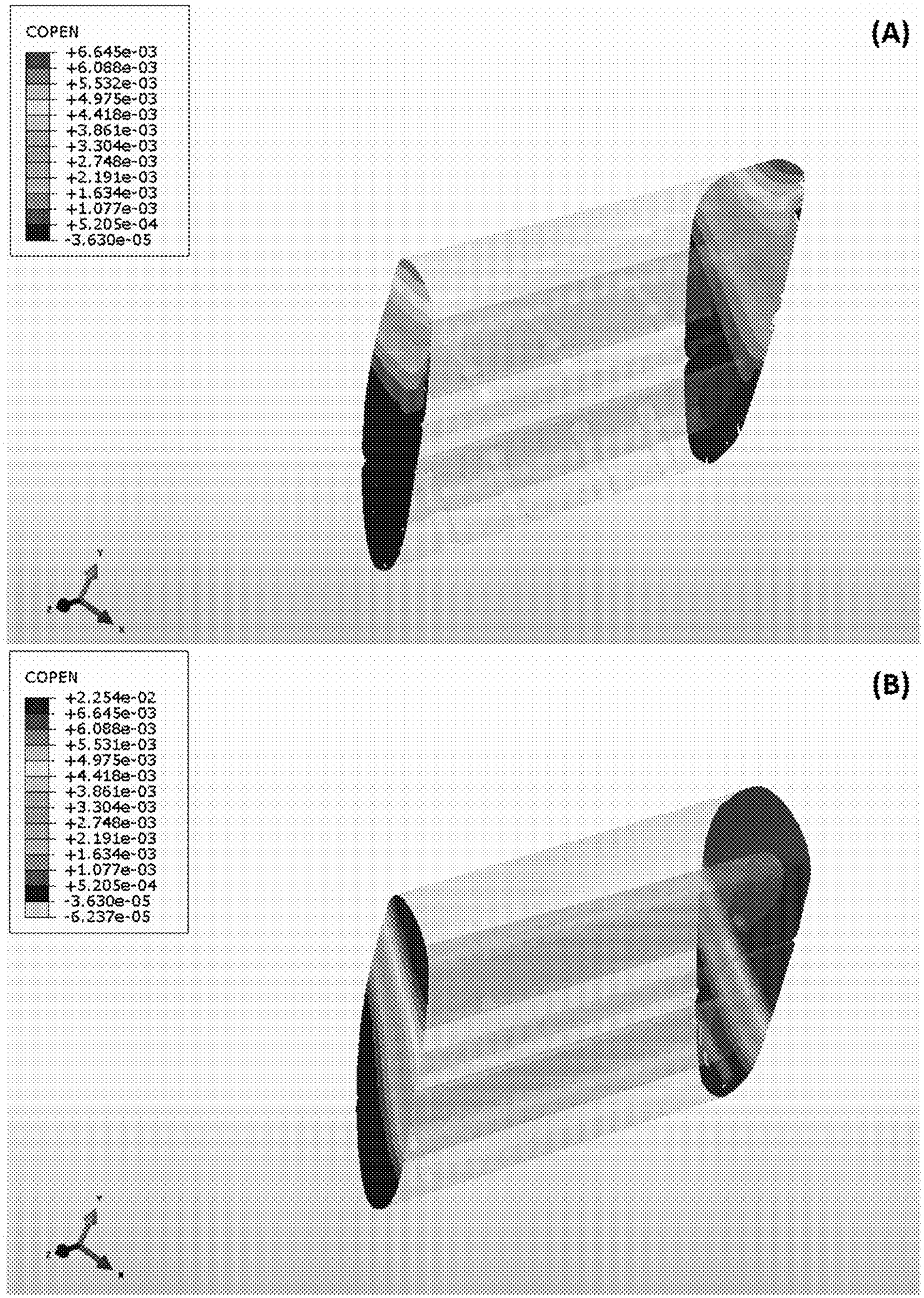
FIG. 27 illustrates the gap between the interfaces of bone graft/host mandible after deformation due to normal loading for a) reconstructed mandible by releasable Ti-6Al-4V hardware(s) and Bone Bandaid in the first stage, and b) reconstructed mandible by current Ti-6Al-4V hardware (Units: mm).

FIG. 27 shows graphically that the gap distance between the grafted bone and host mandible is reduced compare to the case of using Ti-6Al-4V hardware(s) and a double fibular barrel graft. The maximum gap distance for the new case of using standard hardware and the Bone Bandaid is 6.7 micron, while for currently used hardware the maximum distance is 22.5 microns. In both cases the gap distance is in a safe region, since it is less than 200-300 microns.

Compressive Stress at the Graft/Host Mandible Interface

Figure 28:
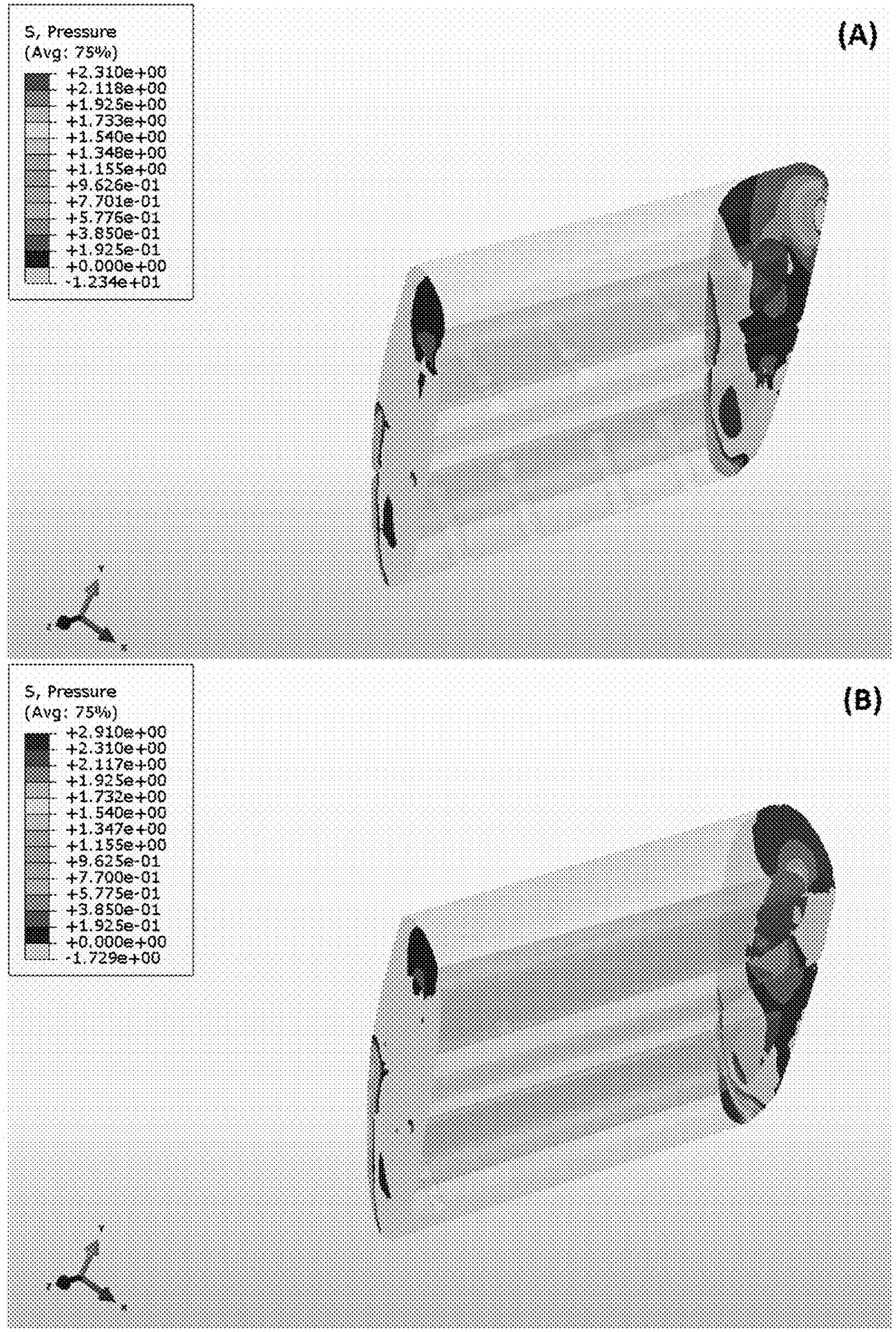
FIG. 28 illustrates compression stress at the interface between graft/host mandible for a) reconstructed mandible by releasable Ti-6Al-4V hardware(s) and Bone Bandaid in the first stage, and b) reconstructed mandible by current Ti-6Al-4V hardwares. Compression values are shown as positive (Units: MPa).

FIG. 28 graphically demonstrates that the compressive stress magnitude is reduced for the suggested structure in some regions, especially in inferior part of right interface, compare to current standard of care. However more areas are seen to be under compression in the new case which may be due to existence of the wire-frame apparatus; this effect can be seen especially for the upper graft.

The Released State

Figure 29:
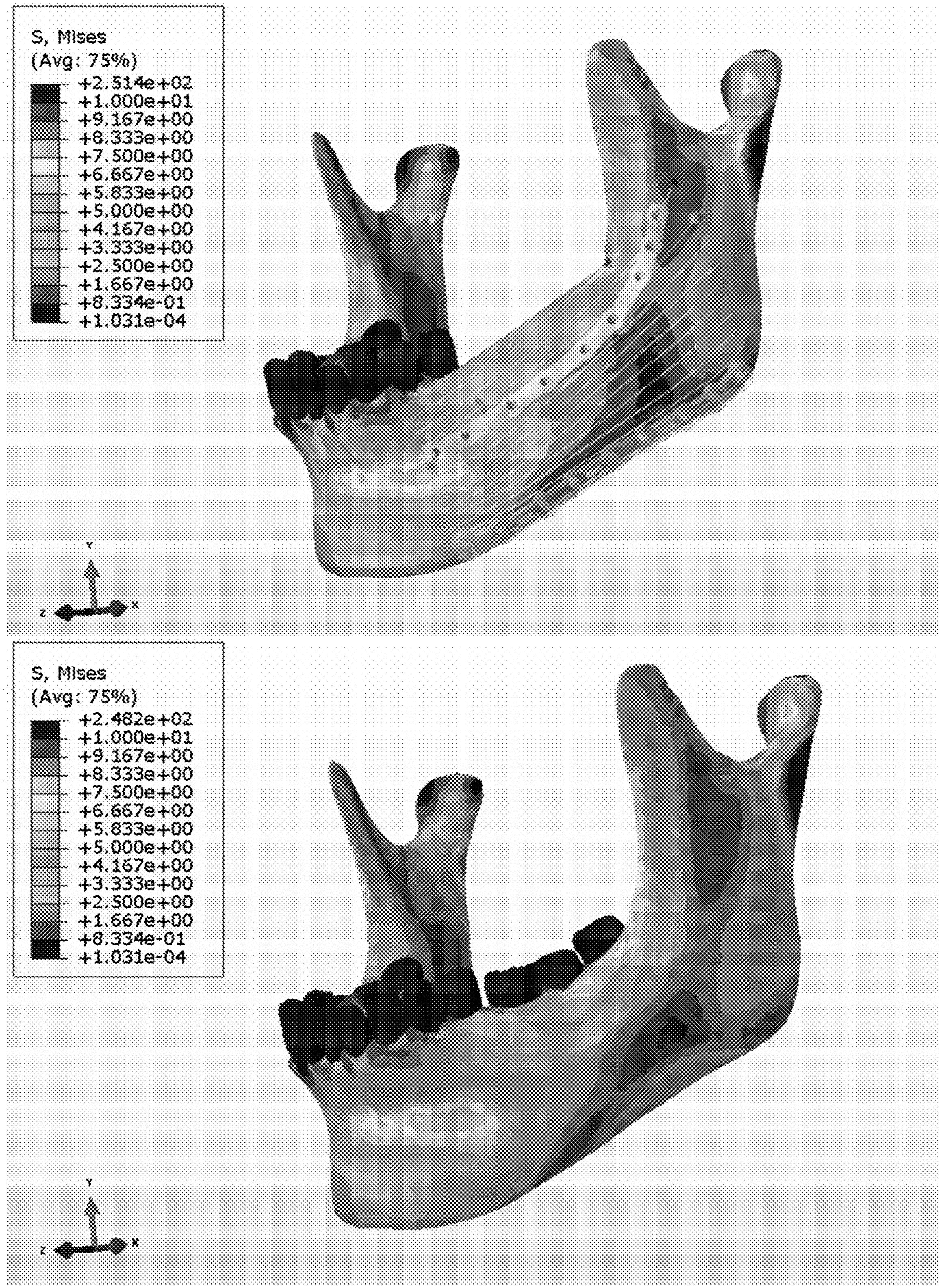
FIG. 29 illustrates stress distribution (von Mises stress) for a) reconstructed mandible by releasable Ti-6Al-4V hardware and Bone Bandaid in the second stage, and b) normal mandible. Compression values are shown as positive (Units: MPa).

The purpose of this stage is not to have the Ti-6Al-4V hardwares functional, so the wire-frame apparatus, Bone Bandaid, play the crucial role which would be recreating stress distribution among graft and mandible. Although in current standard of care the power loss of 40% can be observed among patients after the post-surgical healing period, this new structure promise normal loading. FIG. 29 depicts the stress distribution under normal loading for the stage II of suggested structure, versus normal mandible. It shows that the distribution is the same as in a normal mandible which should cause the bone to remodel in a normal way. As a result, the grafted bone would become stronger and more likely to be a strong support for a dental implant.

3. Conclusion

The current standard of care for mandibular reconstruction is the use of Ti-6Al-4V fixation hardware and a fibular double barrel graft. The major problem with the standard of care fixation hardware is its very high stiffness compared to cortical bone. The permanently implanted hardware tends to change the normal stress-strain trajectories by relocating most if not all of the stress caused by the masticatory muscles to the plate and its fixation screws due to its high stiffness compare to cortical bone. Shayesteh et al., as described in Section II above, has demonstrated that stiffness-matched fixation hardware will facilitate grafted bone remodeling resulting in more stable bone that better supports the incorporation of dental posts when compared to the case using standard of care hardware. However, no work is done to recreate normal stress distribution along the mandible to restore normal chewing and make it a strong support for dental implant.

We suggest the use of two stages mechanism to de-link bone healing from bone restoration and regeneration of oral power. The components of the mechanism are releasable Ti-6Al-4V hardware(s) and a wire-frame nitinol apparatus, the Bone Bandaid. During the healing period, the high stiff fixation hardware will provide initial fixation of grafted bone. The breakthrough element is the ability to unlock bone fixation in an outpatient procedure once the bone has healed. The unlocking of the immobilization hardware allows the Bone Bandaid to take over in redirecting the stress-strain trajectory to the normal path. The redirected stress-strain trajectory will facilitate bone remodeling of the graft, improve post-operative power in chewing, and the stability of dental implants placed in grafted bone.

Our comparison in Shayesteh et al., as described herein in Section III, uses the current standard of care fixation hardware under 60% of the normal chewing, and is based on healthy mandible under normal chewing. Our Finite Element Analysis for stage I shows that maximum stress concentration on the upper hardware is reduced by a factor of 2.11, and for the lower hardware(s) it is reduced by the factor of 1.96. The maximum stress on the nitinol wires are also confirmed to be in the safe region. The gap distance between the grafted bone/and host mandible is reduced significantly, by the way both case are in safe region. Although the magnitude of compressive stress is reduced in some points of interfaces, the area under compression is increased especially on the right interface. Our results for stage II demonstrate that stress trajectories along the grafted bone and mandible is the same as normal mandible. The results also confirm that the normal chewing has been restored for the reconstructed mandible.

Section IV: 3D Printing of Fixation Hardware Using Nitinol

The implants and surgical guides of the present invention may be fabricated using 3D printing (also referred to as additive manufacturing or AM), e.g., laser sintering 3D printing and/or continuous Digital Light Processing (cDLP) light-based 3D printing (also referred to as projection stereolithography, projection printing, or microstereolithography) (Dean D, Mott E, Luo X, Busso M, Wang M O, Vorwald C, Siblani A, Fisher J P: Multiple Initiators and Dyes for continuous Digital Light Processing (cDLP) Additive Manufacture of Resorbable Bone Tissue Engineering Scaffolds. Virtual and Physical Prototyping, DOI: 10.1080/17452759.2013.873337, 2014). Additive manufacturing of implants having precisely defined mechanical and geometrical features requires comparatively high levels of printing accuracy. This is especially true where the implant has a complex internal pore structure. (Stereolithography as described by Paul Jacobs in: Rapid Prototyping & Manufacturing: Fundamentals of StereoLithography by Paul F. Jacobs (Jan. 15, 1992), and Stereolithography & Other RP&M Technologies: From Rapid Prototyping to Rapid Tooling by Paul F. Jacobs (Jan. 1, 1996). cDLP 3D printing is one form of photo-initiated additive manufacturing that is used to render useful and accurate medical parts and implants. PCT/US2013/072623.

Non-additive (traditional) fabrication techniques such as Computer Numerical Control (CNC) or hot extrusion molding may also be used to manufacture implants with biodegradable/bioabsorbable metals, metal alloys as well as other biocompatible materials. Any method of fabricating accurate implants, implant components and surgical guides that are not immunogenic or toxic and that have the proper resorption profile may be used with the methods and systems of the present invention.

Figure 30:
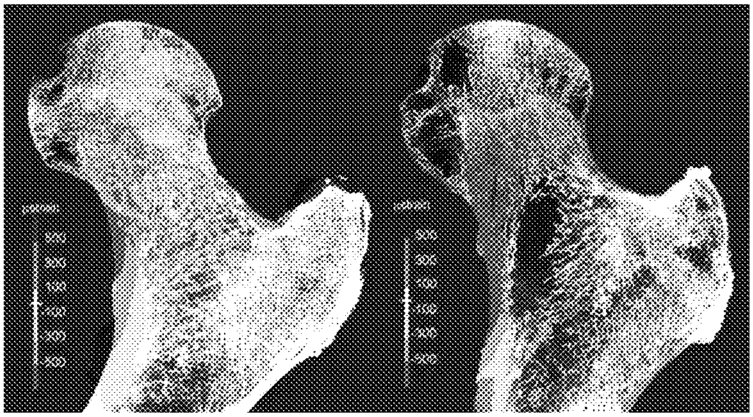
FIG. 30 illustrates an example of an FEA analysis of a portion of a bone such as the head of the femur.

The anatomic structure may be analyzed using 3D Computerized Tomography (CT) scan imaging. Other 3D imaging techniques that may be used include ultrasound and Magnetic Resonance Imaging (MRI). Using the 3D CT scan data, a patient-specific implant that recreates the normal anatomic stress-strain trajectories is developed and then fabricated. CT data is used to develop a finite element analysis (FEA) of an anatomic region which may contain bone. (Morgan et al. Use of finite element analysis to assess bone strength. BoneKEy-Osteovision 2:8 (2005)). The FEA analysis is integrated with all available data from that anatomic region, including, muscle and joint contact loads to produce a 3D FEA model of the area (for example, see, Cheal et al. Journal of Orthopaedic Research 10 (3): 405 (1992)). FIG. 30 illustrates an example of an FEA analysis of a portion of a bone such as the head of the femur.

An FEA analysis is used to develop a model of an implant that closely matches the stress-stain profile of the normal anatomy.

Figure 31:
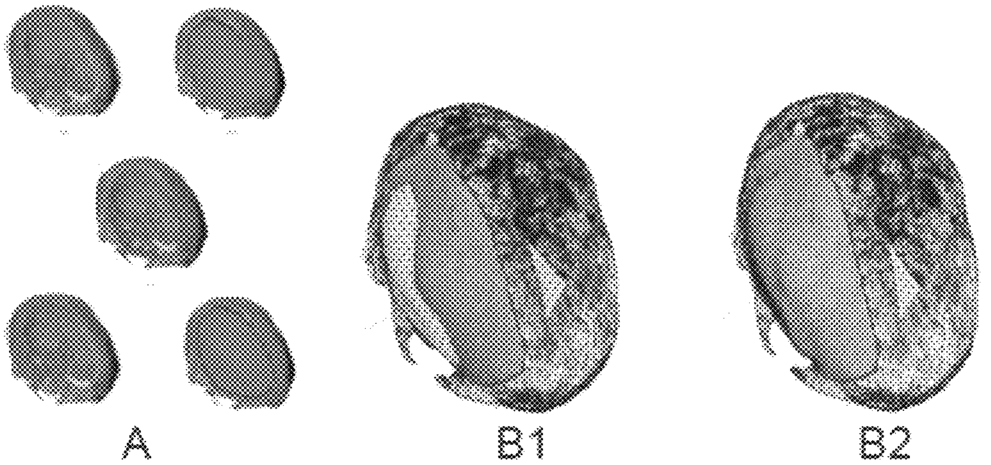
FIG. 31 illustrates: A. Template (blue) matched to edge (red crest line) of defect via a 2 pass warp; B. Correction of implant intersection with surrounding tissues: B1 has intersections; B2 intersections corrected.

Various systems and methods of designing patent-specific implants exist, such as implant Computer Aided Design (CAD). However, traditional CAD approaches start the design process with ideal shapes (e.g., cylinders, cubes, etc.) that are not useful for the design of implants that will be ready to fit, i.e., seat or match, a patient's specific defect prior to opening of the surgical site. The methods and systems of the present invention allow for the design of a patient-specific implant for any segment of the anatomic structure. A key aspect of such a design is creating implants that have the correct 3D geometry for a particular anatomic area where the implant is seated. For example, with reference to FIG. 31, patient-specific cranial implants can be designed by identifying the shape of the defect and then, using a template image produce an implant shape that not only fits the bone margin (for surgical attachment), but also, properly "seats" in the defect so as to not intersect or apply a load to inappropriate tissues surrounding the defect site. U.S. Patent Application Publication Number 20140003695 describes the design of patient specific cranial implants as well as patient-specific implants for any area of the body.

Figure 32:
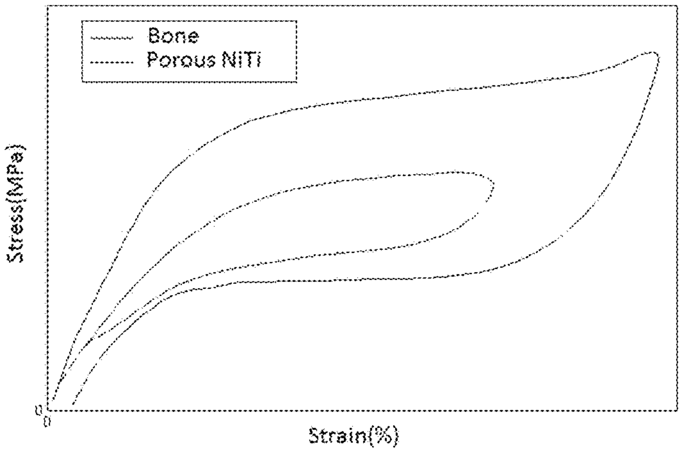
FIG. 32 graphically illustrates that porous nitinol can be more or less stiff than bone.
Figure 33:
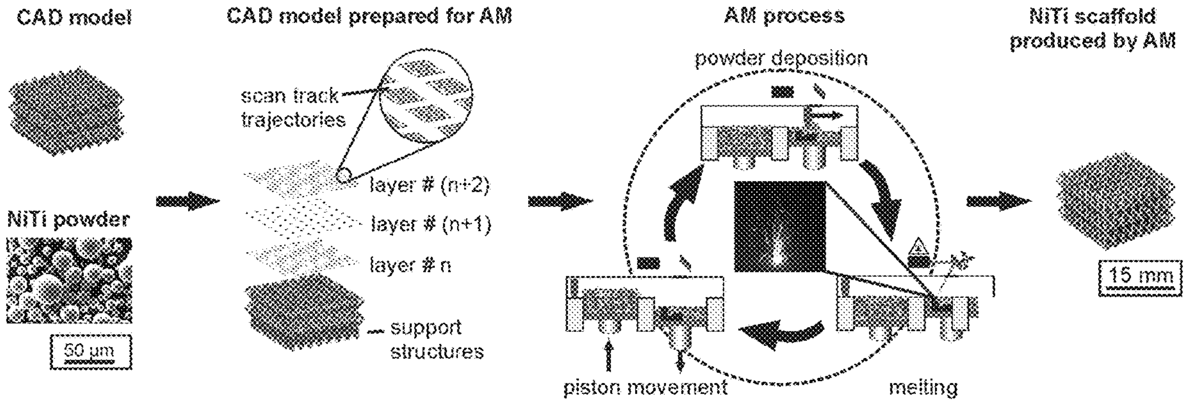
FIG. 33 illustrates a powder bed for AM of nitinol and Mg-alloy devices.
Figure 34:
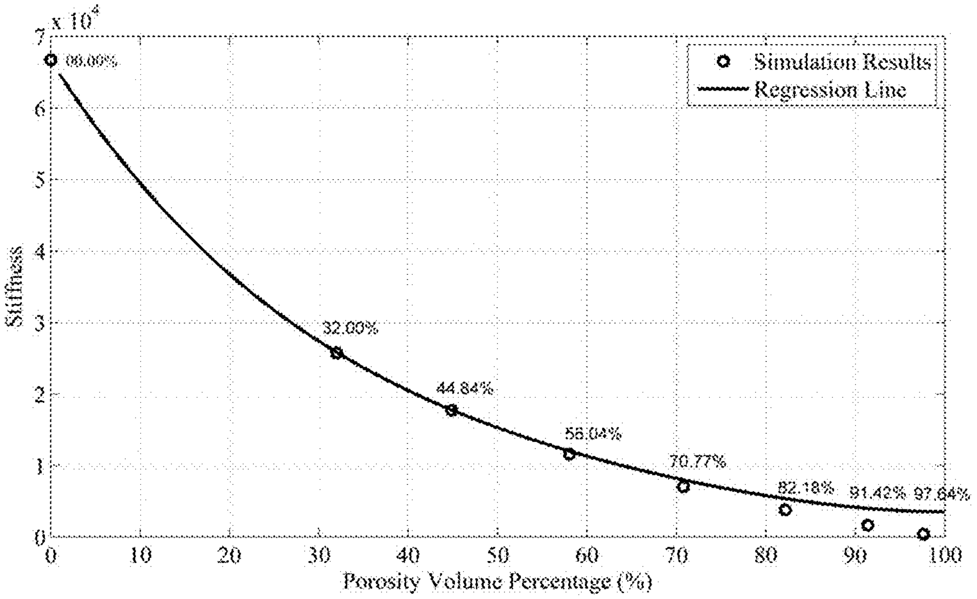
FIG. 34 graphically illustrates nitinol stiffness reduction as a function of porosity.

As discussed above, we have demonstrated that porous nitinol, with stiffness ranging from above to below that of cortical bone (FIG. 32), can be rendered by Additive Manufacturing (AM), also known as 3D printing (FIG. 33). Therefore, we are able to match stiffness to the exact need of any location in the mandible (as shown in FIG. 34) or any other bone. The local stiffness requirements in different portions of the mandible can be determined from a patient's CT-scan (Table 8).

TABLE 1

| Stiffness (Young's Modulus) | |
|---|---|
| Mandibular Cortical Bone Region | Stiffness (GPa) |
| Symphysis | 18.9-22.3 |
| Parasymphysis | 17.6-23.5 |
| Angle | 21.3-25.7 |
| Ramus | 20.8-28.7 |

TABLE 1-continued

| Stiffness (Young's Modulus) | |
|---|---|
| Condyle | 21.9-26.4 |
| Coronoid | 25.6-31.2 |
| **Bone Biomaterial Properties** | **Stiffness (GPa)** |
| Bulk Polymethylmethacrylate (PMMA) | 1.8-3.1 |
| Bulk Polyetheretherketone (PEEK) | 3.6 |
| Bulk Polyetherketoneketone (PEKK) | 4.4 |
| Bulk Cobalt-Chromium (Co—Cr) | 240 |
| Bulk Stainless Steel (Fe—C—Cr) | 205 |
| Bulk Surgical Grade 5 Ti (Ti—6Al—4V) | 112 |
| Bulk Nitinol (NiTi) | 48 |
| Bulk Mg—Ca—Zn | 240 |
| Bulk Mg—Zn | 25.5-169.5 |
| Bulk Mg—Ca | 14-51 |
| Porous Nitinol (NiTi) | 10-48 |

Accordingly, there is a need for a paradigm shift in material design methodologies for less stiff, yet fail-safe bone implants and fixation devices. Equally important, there are a number of opportunities such as the possibility of creating patient-specific metallic implants and fixation devices with a range of pre-engineered material properties through the additive manufacturing of superelastic and resorbable alloys. The design of stiffness-matched, 3D printed fixation devices would also benefit from Computer Aided Design software that matches the patient's shape and functional needs to available materials, including natural or tissue engineered bone grafts, to produce sustainable, long-lasting, and normal stress-strain trajectories.

Our group, has successfully established methodologies for designing proper material behavior and fabricating Ti-6Al-4V and NiTi elements using a Phenix [3D Systems] SLM 3D printer. We have found that AM technologies can result in superior part performance. The structural and the functional properties can be degraded significantly by the processing method. We, however, have found that AM is able to produce high quality NiTi.

Additionally, stress induced martensite, work hardening, spring back effects, burr formation, and adhesion can make precise machining quite difficult and can account for significant tool wear (Wu, S., et al., "A study on the machinability of a Ti49.6 Ni50.4 shape memory alloy," Materials Letters, 40 (1): 27-32 (1999)). Due to the limitations of many currently used NiTi processing strategies, current applications mostly use simple geometries (e.g., bar, rod, wire, sheet, tube). While conventional sintering, hot isostatic pressing, and metal injection molding have been used to fabricate dense and porous NiTi implants, the most promising technology for creating cost-effective patient-specific implants with high accuracy and predefined properties is AM (Shishkovsky I. Shape memory effect in porous volume NiTi articles fabricated by selective laser sintering. Technical physics letters. 2005; 31 (3): 186-8; Malukhin K, Ehmann K. Material characterization of NiTi based memory alloys fabricated by the laser direct metal deposition process. Journal of manufacturing science and engineering. 2006; 128 (3): 691-6; Chalker P, Clare A, Davies S, Sutcliffe C J, Tsopanos S, editors. Selective laser melting of high aspect ratio 3D nickel-titanium structures for MEMS applications. MRS Proceedings; 2005: Cambridge Univ Press; Shishkovsky I, Morozov Y, Smurov I. Nanofractal surface structure under laser sintering of titanium and nitinol for bone tissue engineering. Applied Surface Science. 2007; 254 (4): 1145-9; Yang Y, Huang Y, Wu W, editors. One-step shaping of NiTi biomaterial by selective laser melting. Photonics Asia 2007; 2007: International Society for Optics and Photonics; Krishna B V, Bose S, Bandyopadhyay A. Laser processing of net-shape NiTi shape memory alloy. Metallurgical and Materials Transactions A. 2007; 38 (5): 1096-103; Meier H, Haberland C, Frenzel J, Zarnetta R. Selective Laser Melting of NiTi shape memory components. Innovative Developments in Design and Manufacturing: Advanced Research in Virtual and Rapid Prototyping. 2009:233-8).

Generally, the AM processes create physical parts directly from CAD data by adding material in successive layers. For the AM of metals, these layers are usually created from powders that are melted by a laser, as shown in FIG. 33. In processes such as Selective Laser Melting (SLM), the powder material is deposited in 20-100 μm layers by a blade, knife, or a roller. As shown in FIG. 33, a 3D-CAD model of the part is sliced into horizontal layers in a printer setup program in which the original CAD file is visualized. Each layer contains specific information about the part geometry and the scan trajectories for the laser. In an iterative process, a powder layer of a pre-set thickness is deposited; then, the laser beam locally melts the powder according to the geometry information for the layer. After solidification, solid structures remain which are surrounded by loose powder. New powder for the next layer is then deposited on top of the previous layer by the roller. This procedure is repeated until the desired 3D part is produced. In NiTi 3D printing, the process is usually done in a chamber filled with argon to minimize oxidation. Haberland et al. (from our group) (Meier H, Haberland C, Frenzel J, Zarnetta R. Selective Laser Melting of NiTi shape memory components. Innovative Developments in Design and Manufacturing: Advanced Research in Virtual and Rapid Prototyping. 2009:233-8; Meier H, Haberland C, Frenzel J. Structural and Functional Properties of NiTi Shape Memory Alloys Produced by Selective Laser Melting. Innovative Developments in Design and Manufacturing: Advanced Research in Virtual and Rapid Prototyping. 2011:291-6; Haberland C. Additive Verarbeitung von NiTi-Formgedächtniswerkstoffen mittels Selective-Laser-Melting: Shaker; 2012; Haberland C, Elahinia M, Walker J, Meier H, Frenzel J, editors. Additive Manufacturing Of Complex NiTi Shape Memory Devices And Pseudoelastic Components. ASME Conference on Smart Materials, Adaptive Structures and Intelligent Systems; 2013 Sep. 16-18; Snowbird, Utah.: ASME; 2013; Haberland C, Walker J, Elahinia M, Meier H, editors. Visions, Concepts And Strategies For Smart Nitinol Actuators And Complex Nitinol Structures Produced By Additive Manufacturing. ASME 2013 Conference on Smart Materials, Adaptive Structures and Intelligent Systems; 2013 Sep. 16-18, 2013 Snowbird, Utah: ASME; 2013) showed that by using pre-alloyed powders, additively manufactured parts are homogeneous and show high strength and functional properties analogous to conventionally processed NiTi (Meier H, Haberland C, Frenzel J. Structural and Functional Properties of NiTi Shape Memory Alloys Produced by Selective Laser Melting. Innovative Developments in Design and Manufacturing: Advanced Research in Virtual and Rapid Prototyping. 2011:291-6; Haberland C. Additive Verarbeitung von NiTi-Formgedächtniswerkstoffen mittels Selective-Laser-Melting: Shaker; 2012; Elahinia M, Andani M T, Haberland C. Shape Memory and Superelastic Alloys. High Temperature Materials and Mechanisms. 2014:355; Haberland C, Elahinia M, Walker J, Meier H, Frenzel J. Additive Manufacturing Of Complex NiTi Shape Memory Devices And Pseudoelastic Components 2013). AM-fabricated NiTi parts show sufficiently low impurity concentrations to satisfy medical device requirements (ASTM F2063-

05) (Meier H, Haberland C, Frenzel J, Zarnetta R. Selective Laser Melting of NiTi shape memory components. Innovative Developments in Design and Manufacturing: Advanced Research in Virtual and Rapid Prototyping. 2009:233-8).

Additive manufacturing of NiTi has two distinct advantages over conventional methods. First, it circumvents the difficulties associated with machining NiTi and, secondly, it provides a freedom-of-design that conventional processing cannot match. We analyze the effect of process parameters on the structural and functional outcome of NiTi parts produced by selective laser melting. Excellent shape memory behavior is demonstrated in additively manufactured NiTi parts and the ability to produce complex structures with accurate features is demonstrated.

1. Introduction

Often used in the biomedical industry, the use of nickel-titanium (NiTi) shape memory alloys (SMAs) is also growing in the automotive, aerospace fields, and elsewhere. However, these industries currently lack mainstream fabrication methods to produce complex NiTi components, which is severely limiting the potential use of this material. Weinert and Petzoldt (2006) demonstrate the difficultly involved in machining NiTi alloys. While they present optimal parameters for machining, they find that the high ductility and work hardening of NiTi makes processing extremely challenging and can lead to poor workpiece quality. Furthermore, the unique elastic behavior of NiTi causes poor chip breaking, burr formation, and high tool wear. Additionally, the phase transformation temperatures which drive NiTi's shape memory and pseudoelastic behaviors are extremely sensitive to the relative nickel-titanium concentrations. Frenzel et al. (2010) showed that a 0.1% change in nickel content can affect the phase transformation temperatures by approximately 10° K.

Additive manufacturing is a near-net-shaping technology which allows for the direct fabrication of complex metallic components. AM has the capacity to circumvent traditional machining, relieving the manufacturing process from these constraints. AM also enables production of 3D geometries that are not possible using traditional techniques. Complex features such as engineered porosity, hollow parts, curved holes, and filigree structures are fully realizable. Finally, direct CAD fabrication reduces the timescale of the concept-to-prototype transition. Selective Laser Melting (SLM) utilizes a laser beam to manufacture a solid part through the melting and solidification of powdered particles. The part is produced additively by manufacturing one cross-sectional layer at a time from a digitally sliced CAD model.

Few groups have previously demonstrated success in manufacturing NiTi structures by SLM. Meier et al. (2009) studied how process parameters affect the structural properties of shape memory NiTi components manufactured with an AM system of type Realizer SLM 100 (MTT Technologies GmbH, now SLM Solutions GmbH, Lübeck, Germany), equipped with a 100 W ytterbium fiber laser. Later, the same group extended their work to analyze the mechanical and shape memory properties of SLM-NiTi components (Meier et al., 2011), and then to fabrication and validation of pseudoelastic SLM-NiTi components (Haberland et al., 2012). Finally, they reported a comprehensive study of process parameters on density, impurity pickup, phase transformation, shape memory and pseudoelastic behavior (Haberland et al., 2014). Bormann et al. (2012) also used a Realizer SLM 100 to examine the effect of process parameters on phase transformation temperatures and Clare et al. (2008) manufactured SLM-NiTi cantilever beams using a system of the same type, with which they demonstrated two-way shape memory capabilities.

In this work, an SLM system equipped with a 300 W ytterbium fiber laser was used. This represents a 200% increase in laser power over those used in previously published studies, allowing for a significantly expanded parametric study. The effects of SLM process parameters on part density, impurity pickup, transformation characteristics, and shape memory behavior are presented. SLM processing provides an attractive method that may be economic and effective due to reduced process steps. However, SLM processing itself is comparatively slow. An effective way for increasing the effectiveness of the SLM process is increasing the scanning speed. This, however, requires the application of higher laser power to ensure proper material properties. We have shown that SLM processing with significantly increased laser powers and scanning velocities results in comparable material properties, and hence, we demonstrated a significant contribution to a more effective and a more economic SLM process for NiTi.

2. Experimental Methods

Materials

Figure 35:
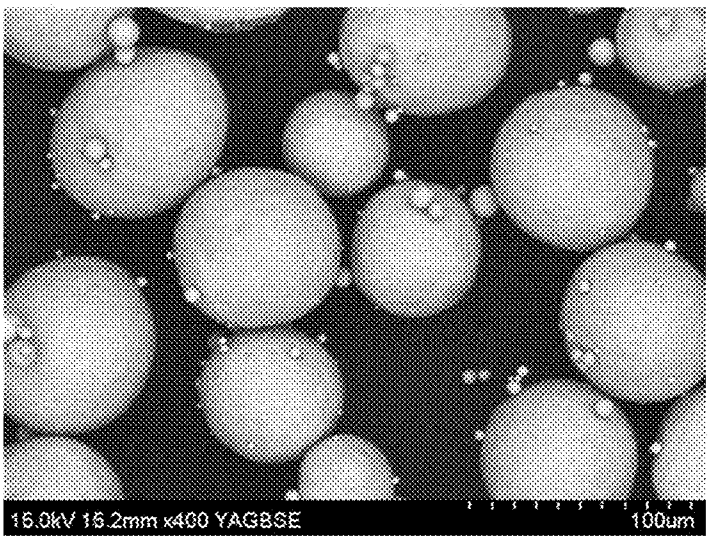
FIG. 35 illustrates a SEM micrograph of the nitinol powder (particle fraction 25-75 μm).

For this study, NiTi ingots (Ni-50.09%) were purchased from Nitinol Devices & Components, Inc. (Fremont, Ca). The ingots were sent directly to TLS Technik GmbH (Bitterfield, Germany) for subsequent atomization by Electrode Induction-melting Gas Atomization (EIGA). Due to the high temperatures required to atomize the ingot material, there is a high risk for impurity pickup during processing. Significant impurity pickup can dramatically affect the material properties and biocompatibility, both of which are extremely important to control. EIGA is a crucible-free method which allows for creation of very pure and spherically shaped powders, free of impurities (associated with crucible based systems), and with extremely low oxygen contents. The resulting powder was sieved to a 25-75 μm particle fraction (FIG. 35). In general, powder particles should be small to allow for deposition of thin layers. Thinner layers increase the resolution of the part by decreasing the inter-layer edge artifact effect, as well as increasing the amount of re-melting that occurs in previous layers (i.e., inter-layer fusing or "stitching"). Re-melting is necessary to induce epitaxial solidification and maximize the density of the resultant part (Das, 2003). However, smaller particles exhibit lower flowability due to higher Van der Waals forces which can negatively affect layer formation. Furthermore, smaller particles are more likely to have higher impurity contents due to a higher surface-to-volume ratio. Haberland (2012b) showed that the 25-75 μm particle fraction is the best compromise of these factors.

Processing

A Phenix-PXM selective laser melting system (Phenix Systems [3D Systems], Rock Hill, SC) was used for processing in this study. Prior to fabrication, a 3D model is drawn in CAD software and then imported into Phenix Systems specialist software where it is sliced into the requisite layers and process parameters are specified. During the powder deposition process, powder is fed upwards by a feed piston. A scraper collects the exposed powder from the top of the feed piston and a tungsten roller deposits the powder on the building platform, resulting in a uniform and slightly compacted powder layer.

The Phenix-PXM is equipped with a 300 W ytterbium fiber laser (cw, $M^2$<1.2, TEM00). The beam is directly focused by a system of galvanometric mirrors and has a fixed focal length. The building platform can be moved upward or downward for working out of the focal plane. When working in the focal plane, as was done in this study, the beam diameter is approximately 80 μm. During processing, the powder particles, heat up and become fully molten upon absorption of laser radiation. The molten particles then bind to each other and re-solidify to produce a fully dense layer. The fabrication piston is then dropped to accommodate deposition of the next layer. The entire process is carried out under an inert atmosphere of argon to minimize oxidation. Layer thickness was fixed at 30 μm throughout this study. Each layer is scanned by the laser using an alternating x-y scan strategy with 90° layer rotation.

Characterization

Microscopy was performed with a Hitachi S-4800 scanning electron microscope (SEM) and a Meiji ML7000 optical light microscope. The ML7000 metallurgical microscope was outfitted with a camera and micrographs were taken using the software ScopePhoto (company, city, state). For micrographs of internal cross-sections, specimens were sectioned with a precision saw (IsoMet 1000, Buehler, city, state) before being mounted and mechanically polished. To analyze the impurity contents, chemical analysis (carbon, oxygen, and nitrogen) was subcontracted to Fort Wayne Metals (Fort Wayne, IN). Impurity contents were measured by interstitial gas analysis per ASTM E1941, ASTM E1447, and ASTM E1409. Phase transformation was evaluated by differential scanning calorimetry (DSC) according to ASTM F2004-05 (Perkin-Elmer, Norwalk, CT). The heating and cooling rates were set to 10° K/min.

To study the mechanical and functional properties of SLM of NiTi, cylindrical rods were manufactured in the vertical direction (diameter=4.5 mm, height=10 mm). For mechanical and functional testing, 1.5 mm was removed from the top and bottom of each cylinder with an IsoMet 1000 precision saw, resulting in a 7.0 mm sample height. Compression testing was performed on an Instron 5569 series tension-compression test system with an Instron extensometer and Bluehill software. Samples were tested in cyclic compression to two different stresses: 300 MPa and 900 MPa. These stress values were chosen because they correspond to important points along the stress-strain curve: the end of the detwinning plateau and near the end of the second elastic region, respectively. Between each cycle, the samples were heated to a temperature 30° C. above their austenite finish temperature and then cooled to 30° C. below their martensite finish temperature to guarantee a fully martensitic state. Testing was conducted well below the austenite start temperature to ensure no thermally-induced transformation would occur during testing. A total of 15 cycles were conducted to each stress level.

3. Results and Discussion

Single Track Analysis

Figure 36:
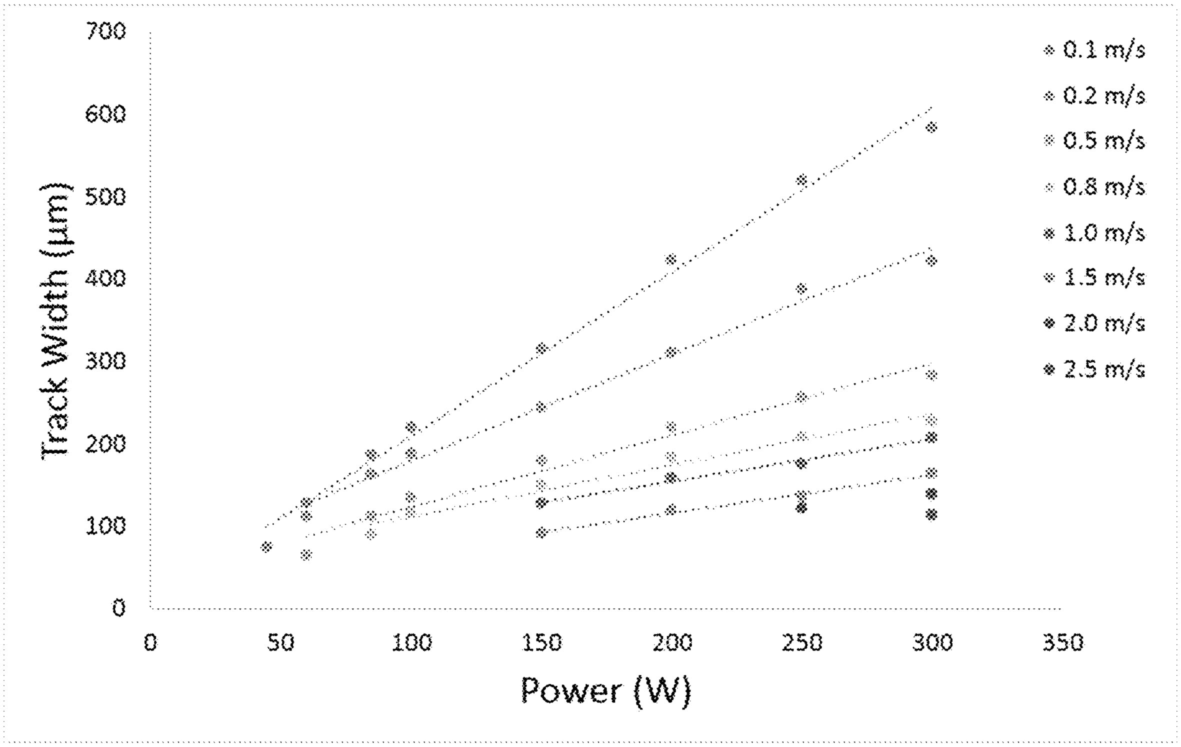
FIG. 36 illustrates single track width as a function of laser power for different scan velocities.

The most basic structure which can be manufactured by SLM is a single layer of an individual laser scan. In this study, single tracks were manufactured with laser power ranging from 45 W to 300 W and scan velocity ranging from 0.1 m/s to 3.0 m/s. In general, higher laser power and lower scan velocities lead to increased energy input, which increases the size of the melt and, as a result, the width of the individual track. FIG. 36 displays the track width as a function of laser power by scan velocity. Note that track width could not be measured for any set of parameters involving a scan velocity higher than 2.5 m/s because the energy was too low to fully melt the powder particles and form a continuous track.

Figure 37:
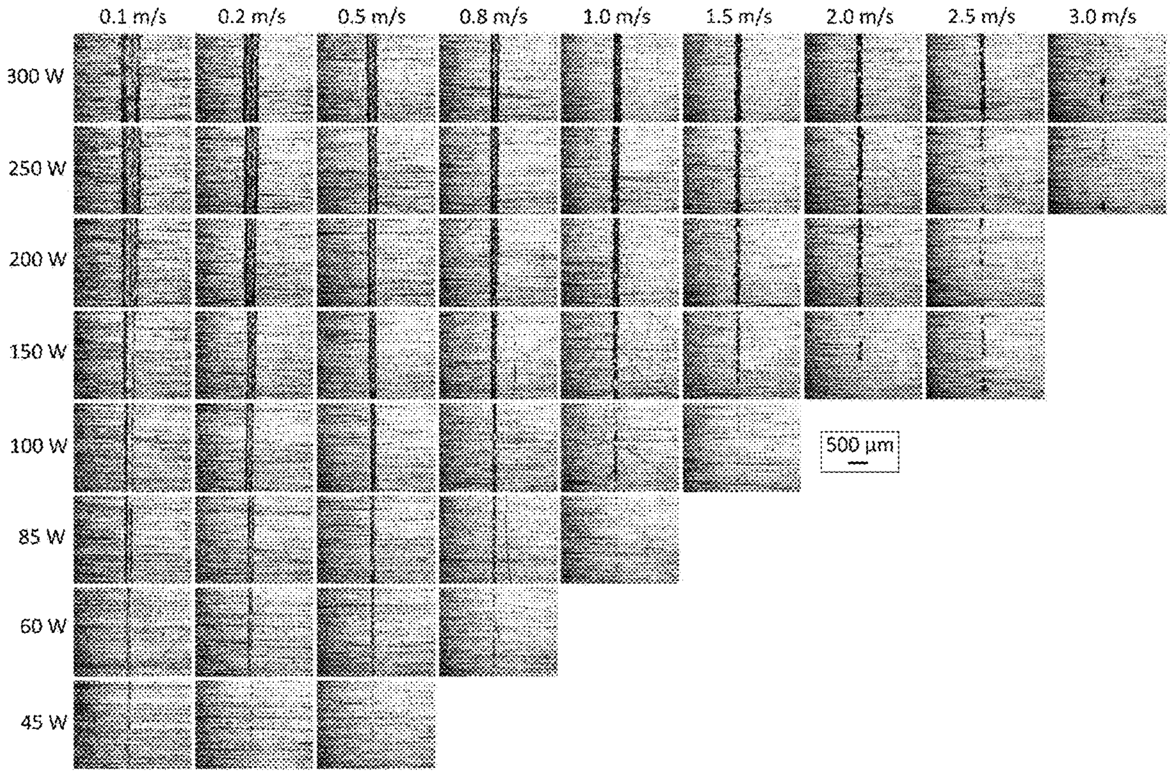
FIG. 37 illustrates micrographs of laser-based and powder-bed-based AM single tracks.

As expected, low scan velocities and high laser powers lead to wider single tracks. The widest track measured was nearly 600 μm (300 W, 0.1 m/s), while the smallest track measured was 66 μm (60 W, 0.5 m/s). Micrographs of selected single tracks are shown in FIG. 37. Interestingly, the relationship between power and track width at constant laser velocity is nearly linear, with the general trend presenting an increasing slope as velocity decreases.

Single tracks with extremely high energy (300 W, 0.1 m/s), exhibit a well-known phenomenon called the “key-hole” effect (Fujinaga et al. 2000). If the input energy is high enough, the powder material can be evaporated, creating a void, or keyhole, which results in higher absorption of laser radiation. Due to the Gaussian beam profile, the maximum energy is focused in the center of the beam and, therefore, the keyhole effect is concentrated along the centerline of each track. In FIG. 37, the keyhole effect can be seen as a trough which runs along the centerline of the single tracks produced with scan velocity of 0.1 m/s and laser powers of 200 W and 300 W.

The effect of too little energy input is also observed in FIG. 37. The single track produced with a scan velocity of 1.0 m/s and laser power of 100 W does not exhibit a continuous line. Here, the energy is too low to maintain a continuous melt in the powder bed. As a result, only small, globular structures are intermittently formed and adhered to the base plate. Gusarov et al. (2007) modeled radiation and heat transfer during SLM and attribute the balling effect to Plateau-Rayleigh capillary instability of the melt. Due to the interrupted natured of the melt, it would be impossible to manufacture a fully dense part with these parameters. It is clear that a compromise must be made to achieve an energy input which fully melts and consolidates the powder without inducing the keyhole effect.

Effect of Process Parameters on Density

Figure 38:
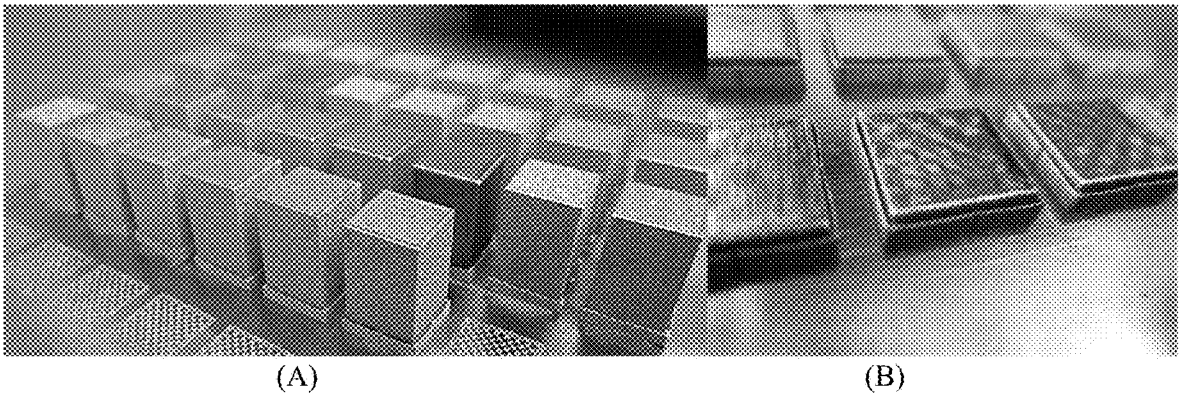
FIG. 38 illustrates a) cuboid nitinol blocks produced by laser-based and powder-bed-based AM with various laser powers and scan velocities, and (b) increased melt pool dynamics caused by high energy input reduce overall part density.
Figure 39:
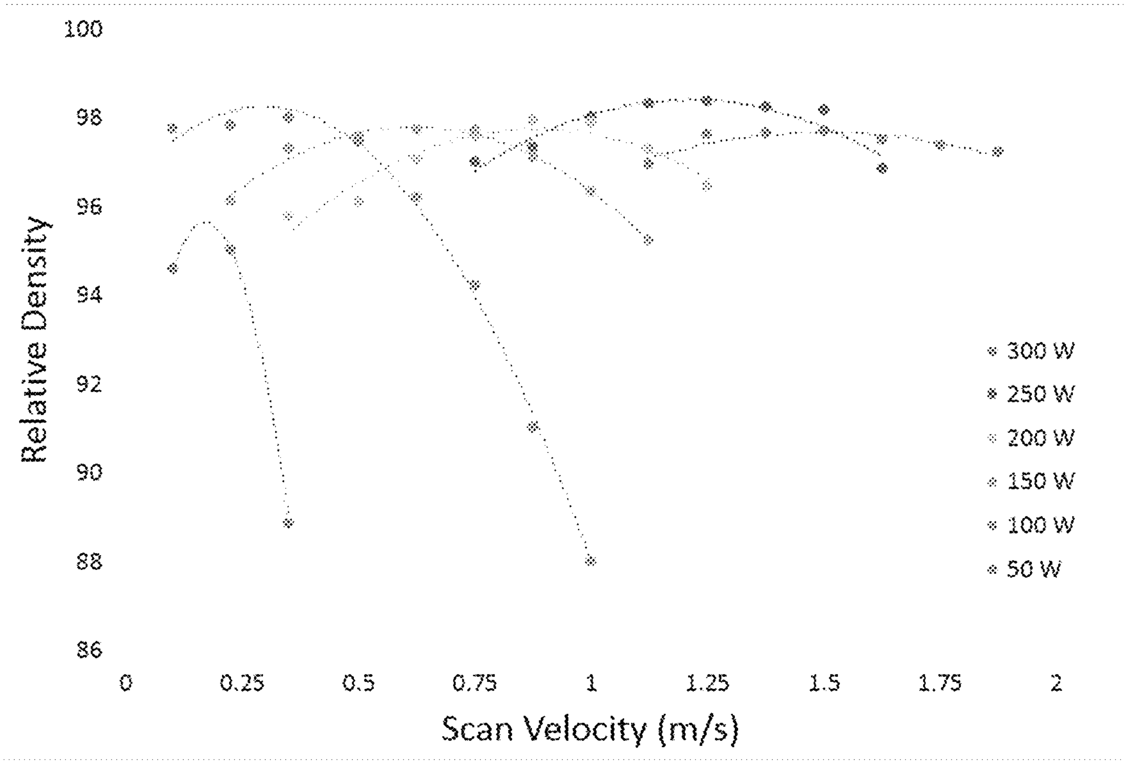
FIG. 39 illustrates relative density of laser-based and powder-bed-based AM NiTi parts as a function of scan velocity for different laser powers
Figure 40:
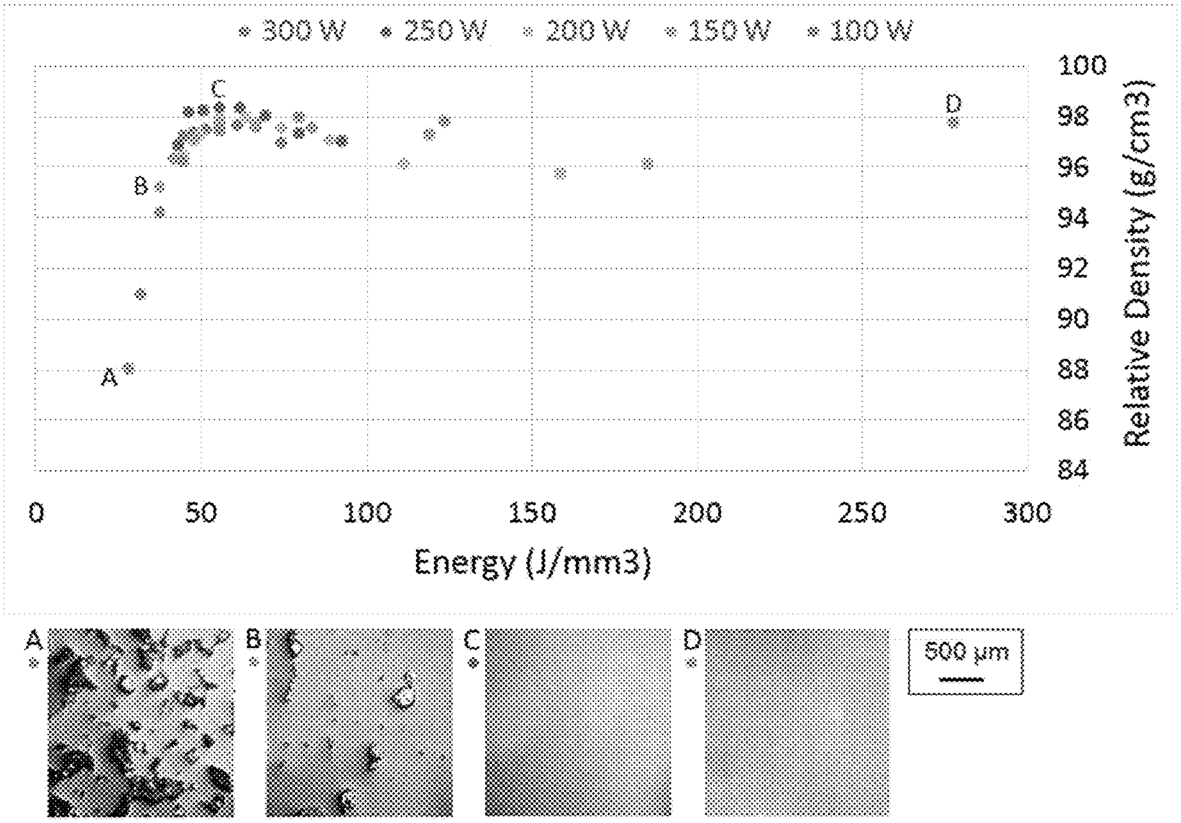
FIG. 40 illustrates relative density of laser-based and powder-bed-based AM nitinol parts as a function of energy density

The main challenge for powder bed AM technologies is to produce a fully dense part from a loose powder bed. An advantage of the Phenix-PXM over other SLM systems is the compaction of the powder bed by a tungsten roller before each layer is processed. The relative density of cuboid blocks (seen in FIG. 38*a*) are expressed as a percentage of maximum theoretical density (6.45 g/cm$^3$) in FIG. 39. FIG. 39 shows the relative density as a function of scan velocity broken down by laser power. Quite predictably, there is a noticeable decrease in relative density for each power input as the scan velocity is increased, corresponding to a lower amount of total energy input. This is particularly evident in the 50 W and 100 W samples. Interestingly, there is also a noticeable decrease in density at lower scan velocities for each power as well. In these cases, the higher input energy leads to melt instabilities, poor surface geometries (wavy structures, FIG. 38*b*), and evaporation effects which affect density. This negatively affects the powder deposition in the subsequent layers and can lead to the creation of cavities within the parts.

In order to quantify multiple parameters at one time, a simple metric for energy density (Equation 1) is often used (Meier and Haberland, 2008). FIG. 39 shows the relative density of SLM NiTi parts as a function of energy density, $\omega_v$, given by:

$$\omega_V = \frac{P}{v_s \cdot \Delta h_s \cdot d_t} \quad \text{(Eq. 1)}$$

where P is laser power, scan velocity is $v_s$, hatch spacing is $\Delta h_s$, and layer thickness is dr. We observed that for input energy densities less than 40 J/mm$^3$, there is an obvious drop off in subsequent part density. The lowest energy density tested (27.7 J/mm$^3$) corresponds to the lowest relative density (88%). The micrograph for this sample does indeed show many large pores throughout the cross-section of the part. A micrograph of a sample manufactured with energy density of 37 J/mm$^3$ shows fewer and smaller pores, but still a relatively substantial amount.

Above 40 J/mm$^3$, virtually all of the samples show high relative density. Among these, is the combination selected as optimal (P=250 W, $v_s$=1.25 m/s, $\omega_v$=55.5 J/mm$^3$). This sample has a measured relative density of 98% and the micrograph confirms that it is free of any visible pores. Although there are other parametric combinations which result in fully dense parts, it is significant that this combination has a relatively low energy density, which will help to minimize impurity pickup during processing.

Figure 41:
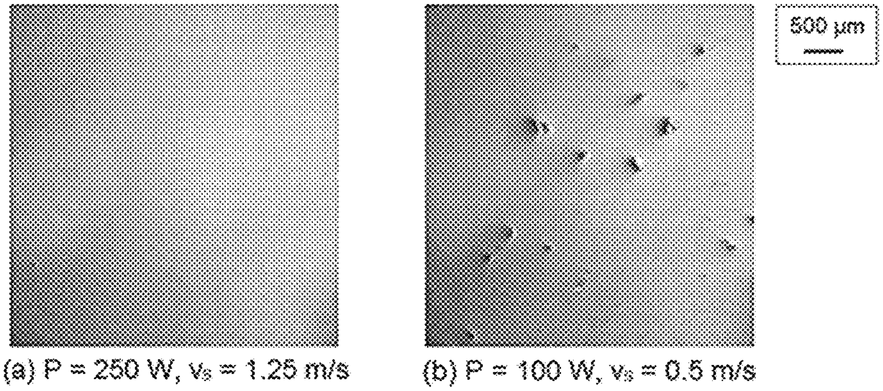
FIG. 41 illustrates a comparison of pore formation in two laser-based and powder-bed-based AM nitinol parts manufactured with the same energy density: 55.5 J/mm$^3$

It is important to consider that while the energy density is a useful metric to characterize general trends, it is a relatively simple metric and many other factors are at play during the SLM process. Not every combination of parameters that have the same energy density will produce the same results. As an example, FIG. 41 compares micrographs of two parts manufactured with the same energy density by different combinations of process parameters. Density measurements and microscopy confirm that the (a) combination of parameters results in a more dense part than the (b) combination. Nonetheless, it is shown that energy density is extremely useful in predicting general trends while varying multiple process parameters.

To analyze the effect of hatch spacing, twelve samples were produced with different hatch distances. The smallest hatch spacing was set to 60 μm and then subsequently increased in 25% iterations. All of the parts were manufactured with otherwise constant process parameters (P=250 W, $v_s$=1.25 m/s, $d_s$=30 μm).

Figure 42:
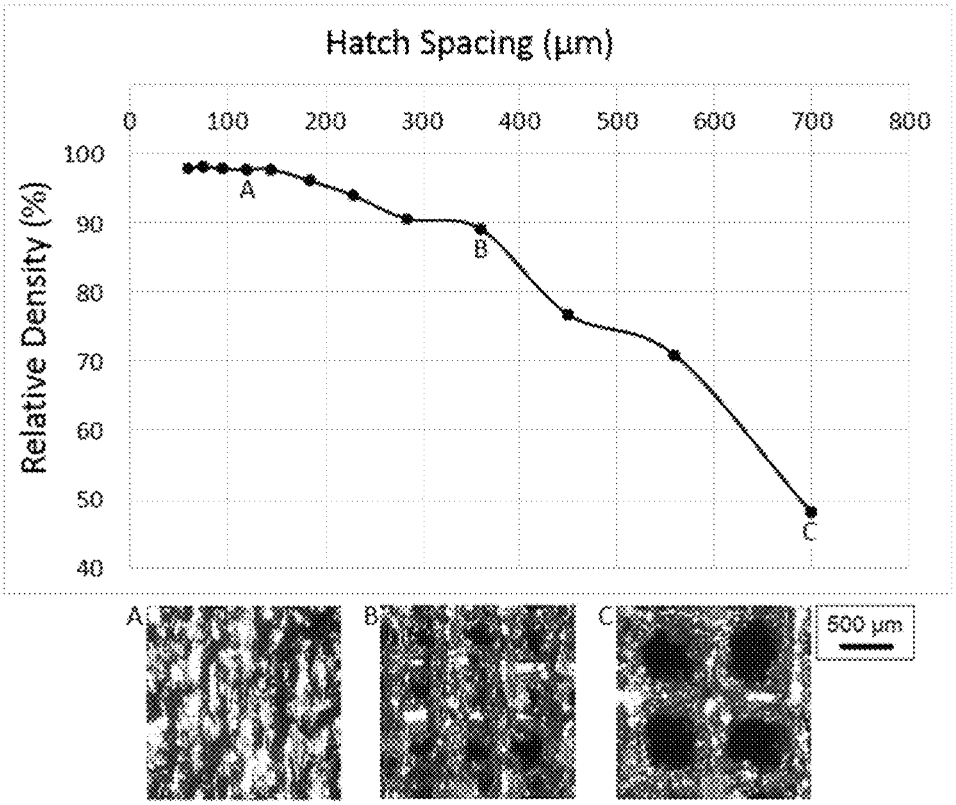
FIG. 42 illustrates an effect of hatch spacing on the relative density of laser-based and powder-bed-based AM nitinol parts.

FIG. 42 shows the effect of varying hatch spacing while using the optimal parameter setup (P=250 W, $v_s$=1.25 m/s, $d_s$=30 μm) on relative density. It is shown that with these process parameters, hatch spacing between 60 μm and 145 μm can be used to produce fully dense parts (>98% relative density). Further increasing of the hatch spacing starts to yield lower density parts. This is due to the lack of overlap between adjacent tracks. Based on these results, which show that 120 μm hatch spacing is sufficient to produce a fully dense part, but is not very far from the point where relative density starts to decline (>140 μm). We determined that 120 μm is the ideal hatch spacing to use with this parameter setup.

Effect of Process Parameters on Impurity Pickup

Chemical impurity pickup during SLM processing is a concern for mechanical, functional, and biocompatibility properties. The NiTi alloy is very reactive during melt-based additive manufacturing and easily forms $Ti_4Ni_2O$ oxides during processing (Khalil-Allafi et al., 2002). This is highly undesirable as minor compositional variances and microstructural defects can have drastic effects on the phase transformation behavior of NiTi. Furthermore, there are strict standards regulating the maximum allowable contents of nitrogen, oxygen, and carbon in NiTi parts which are intended to be used as implantable medical devices (0.05% wt.; ASTM F2063).

Figure 43:
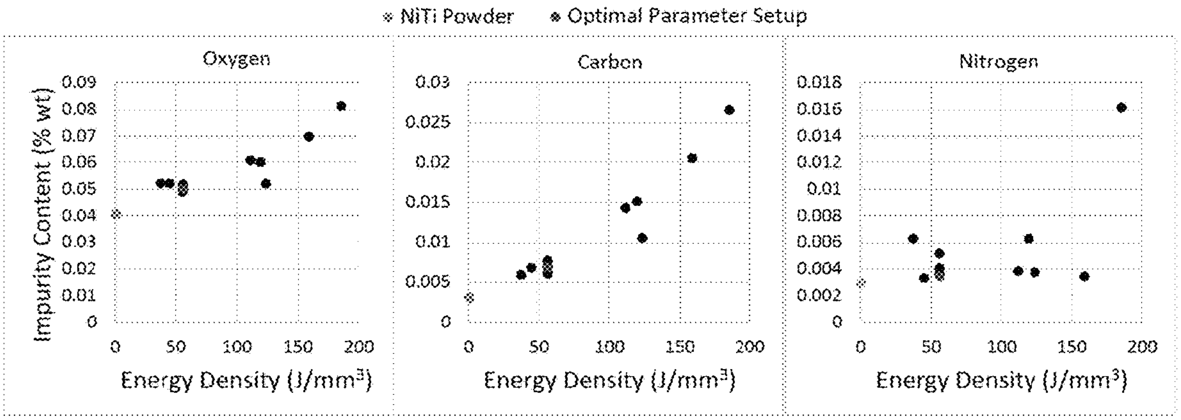
FIG. 43 illustrates oxygen, carbon, and nitrogen impurity pickup in laser-based and powder-bed-based AM nitinol parts.

Ten NiTi samples were manufactured with different combinations of laser power and scan velocity to capture a wide range of energy densities ranging from 44 to 185 J/mm$^3$. FIG. 43 shows a clear trend of increasing oxygen and carbon impurities in the SLM-NiTi parts with increasing energy input. Very little nitrogen was picked up during the process (sans one outlier) and no particular trend is apparent. Using the optimized parameter setup ($\omega_v$=55.5 J/mm$^3$; P=250 W, $v_s$=1.25 m/s, $d_s$=30 μm, $\Delta h_s$=120 μm), it is shown that impurity pickup can be relatively minimized while maintaining high density in the SLM part.

Transformation Characteristics of SLM NiTi

Figure 44:
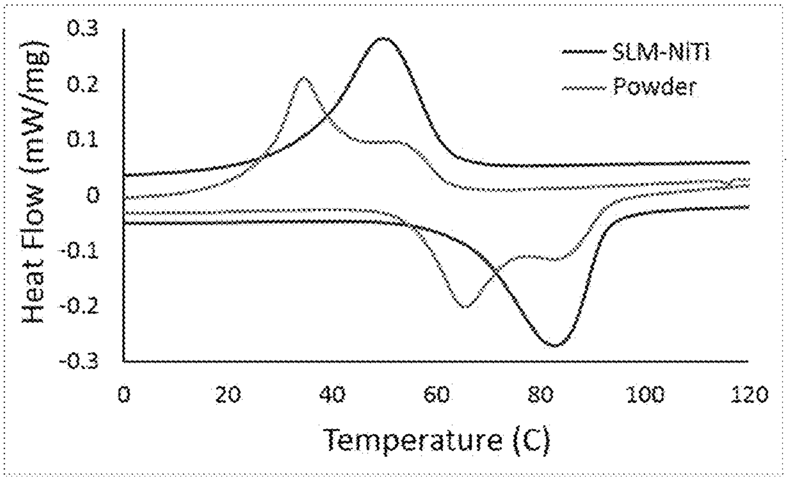
FIG. 44 illustrates transformation temperatures of laser-based and powder-bed-based AM nitinol part and nitinol powder.

As shown in FIG. 44, the SLM process results in slightly increased transformation temperatures compared to the powder. For the SLM part manufactured with the optimal parameter setup, the martensite start ($M_s$) and martensite finish ($M_f$) temperatures were found to be 62° C. and 35° C., respectively. The austenite start ($A_s$) and austenite finish ($A_f$) temperatures were found to be 65° C. and 92° C., respectively. At the peaks, this represents a shift in temperatures to higher values by 16° C. in both the heating and cooling directions, with respect to the transformation temperatures of the powder.

It is believed that the increase in transformation temperatures after SLM can be attributed to nickel evaporation during processing. Due to the extreme sensitivity of the transformation temperatures to alloy composition, a small amount of nickel evaporation can have a significant effect on material properties. For this reason, nickel evaporation and the resulting shift in transformation temperatures should be considered when selecting powder for manufacturing nitinol components by SLM. Moreover, it has been shown by Haberland et al. (2013) and Bormann et al. (2012) that increasing energy inputs lead to greater shifts in transformation temperatures.

Shape Memory Behavior of SLM-Rendered NiTi Parts

Figure 45:
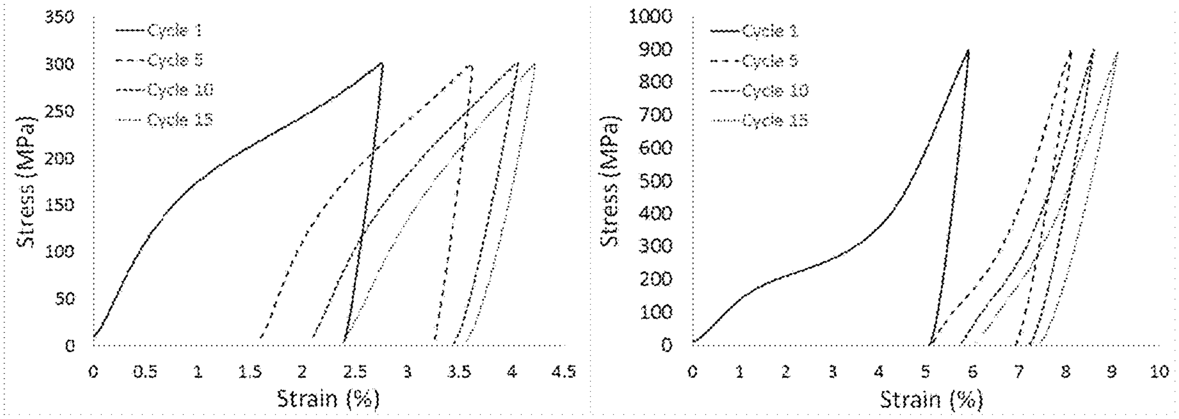
FIG. 45 illustrates shape memory cycling of laser-based and powder-bed-based AM nitinol to 300 MPa (A) and 900 MPa (B).

The shape-memory behavior of SLM-NiTi, evaluated to 300 MPa and 900 MPa, is shown in FIG. 45. As expected, cyclic loading to 900 MPa results in a much higher amount of irreversible strain.

Figure 46:
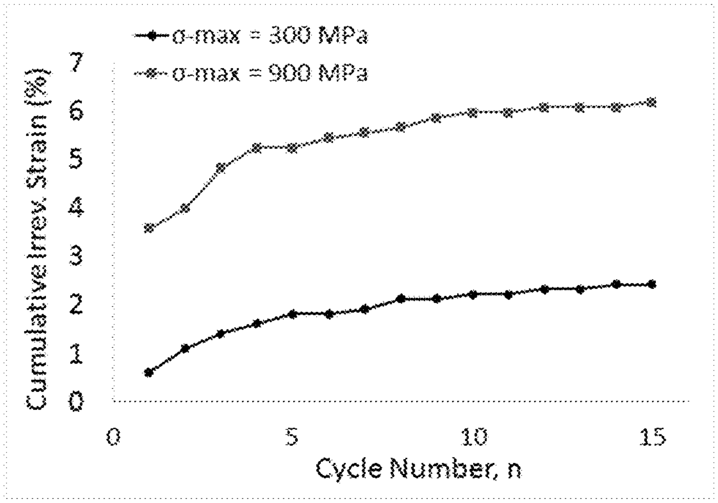
FIG. 46 illustrates cumulative irreversible strain in laser-based and powder-bed-based AM nitinol during cyclic testing to 300 MPa and 900 MPa.

During 900 MPa loading, the specimen accumulated 3.6% irreversible strain in the first cycle alone. By the eighth cycle, a total of 5.6% irreversible strain had accrued, after which the shape memory behavior became a lot more regular. From the ninth to the fifteenth cycle only 0.5% more irreversible strain occurred, resulting in a total irreversible strain of 6.17% for fifteen cycles. Congruent behavior is shown for 300 MPa loading, with total cumulative strain after 15 cycles equaling a much lower value of 2.4%. Accumulation and stabilization of the shape-memory behavior is illustrated in FIG. 46. Haberland et al. (2014) reported similar trends for the behavior of SLM-rendered and conventionally manufactured NiTi parts in cyclic testing.

Complex NiTi Components Produced by SLM

Not only is machining NiTi difficult, but SLM offers a geometric freedom of design that is unobtainable with conventional fabrication techniques. FIG. 46 shows SLM-NiTi structures which were produced with a CAD-designed pore structure and still possess normal shape memory properties. This is a technology which has the ability to drastically influence design methodologies for complex damping and actuation systems. SLM-NiTi could also be used to improve orthopedic implant technology. It is well known that the current metals used in implant technology are often too stiff and therefore cause issues related to stress-shielding. Huiskes et al. (1992) modeled adaptive bone remodeling in the presence of total hip stem implants and showed that lowering the elastic modulus of the implant material to a value similar to cortical bone considerably reduces the amount of long-term bone loss.

Figure 47:
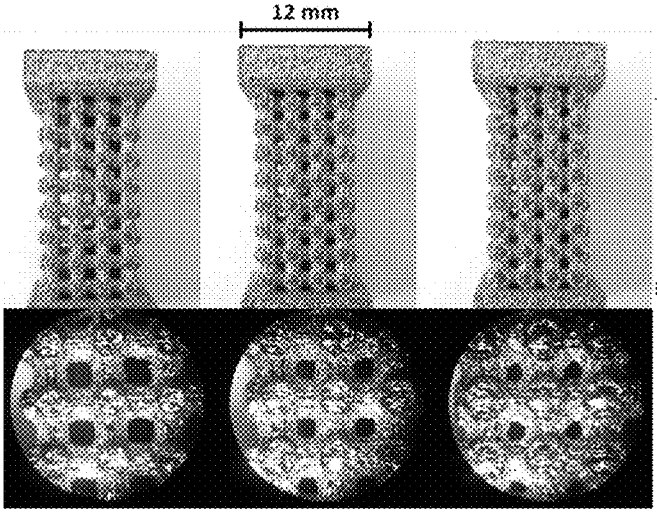
FIG. 47 illustrates porous laser-based and powder-bed-based AM nitinol structures; from left to right: (A) 58% porosity, (B) 45% porosity, (C) 32% porosity. Note: this porosity was the result of build parameters that are currently unknown to the CAD software in which these parts were drafted.

FIG. 47 shows that by introducing orthogonal porosity to SLM-NiTi specimens (in the martensitic state), the effective elastic modulus can be reduced to the range found in cortical bone.

4. Conclusion

The effect of varying process parameters during selective laser melting of NiTi was studied. Compared with previously published studies on SLM of NiTi, the Phenix-PXM system used in this work had a much more powerful laser, allowing for a larger parametric study. An initial study of the quality of single tracks allowed the optimization of build parameters for further analyses. Very high energy inputs were shown to result in severe keyholing and very low energy inputs were not capable of sustaining a continuous melt. For three-dimensional parts it is shown that, in general, relative density increases with increasing energy input (lower scan velocity and/or higher laser power). However, it is also shown that too high energy inputs can also lead to pore formation within the part, thus reducing its density. Thus, low and high: energy, track speed, and laser power settings can result in less than maximal part density. Based on this study, the optimal build parameters for SLM rendering of maximally dense NiTi parts on a Phenix-PXM machine are determined to result from an energy density of $\omega_v$=55.5 J/mm$^3$ (P=250 W, $v_s$=1.25 m/s, $d_s$=30 μm, $\Delta h_s$=120 μm). Interestingly, these parameters are well out of the range of previously published studies, which were limited to devices with a 100 W laser. A single track manufactured with the optimal setup determined in this study has a width of approximately 163 μm, resulting in a 36% overlap between adjacent tracks. We show that impurity content and transformation temperatures both have a tendency to increase post-SLM. However, the impurity pickup and transformation temperature shifts from pre-fabrication models can be minimized by operating at optimal (i.e., sub-maximal) input energies. Given the importance of these parameters, it is important to accounted for them during SLM part rendering. Finally, the shape memory behavior of SLM-rendered NiTi parts is validated through cyclic compression testing. The ability to reliably design and produce parts with complex geometries and predicted shape memory behavior is demonstrated in this study.

Section V: 3D Printing and the Effect of Part Orientation

Additive manufacturing (AM) of metals is a highly complex activity due to a high number of process parameters (e.g., laser power, scanning velocity, focusing, etc.) and process variables (noble gas flow, powder size and distribution, etc.) as well as a high number of process design variations (scanning regime, support structures, number of parts in each process, etc.). As a result, the set-up and design of metal AM process has to be done individually for each part through mostly an iterative procedure involving trial-and-error. Hence, a first-time-right production even for well-experienced users is often not possible. This is true even if the process parameters are optimized for a material. Because in addition to the process parameters other factors like part geometry and part orientation play a significant role in success of manufacturing using AM. Both, however, are strongly associated with each other: the orientation must follow the geometry. If a part is not properly oriented the resulting AM produced parts will have insufficient quality and the process could fail due to several reasons. These adverse effects are explained here and summarized schematically in FIG. 48.

Dimensional accuracy and defects: Because of the layer-based processing, certain geometries can be produced more accurately than the others. Due to layering, overhangs as well as surfaces with a flat inclination angle and downward concave surfaces tend to sag slightly despite the existence of the support structures. Other factors that lead to inaccuracy are the staircase effect and the slight inhomogeneous shrinkage in different directions. The other causes of dimensional inaccuracy particularly are warp and distortion. AM metal parts are usually characterized by high residual stresses due to non-uniform heat conduction, high thermal gradients, and heat build-ups during processing. Especially, large layer cross sections and large disparities or jumps in cross section dimensions of successive layers are critical for heat build-ups and high residual stresses. In severe cases, these stresses can introduce cracks. To avoid inaccuracy and defects due to warp and distortion therefore, it is essential to choose proper part orientation to minimize large and/or disparate layer cross sections.

Surface quality: AM parts usually have insufficient surface qualities which do not meet the requirements of a ready-to-use part. Hence, a surface finishing of the part is required. In addition, it is well known that orientation affects surface quality. AM parts exhibit inhomogeneous surface morphologies due to the staircase effect and surface orientation. In addition, surfaces attached to support structures require extensive finishing. This becomes even more important if these surfaces are functional faces or internal faces where the support structures cannot be removed. To find proper orientation therefore one has to consider different surface morphologies as a result of AM as well as the part design for subsequent removal of support structures.

Anisotropy: Metallic AM parts are characterized by microstructural anisotropy due to inhomogeneous heat conduction effects and mechanical anisotropy due to the layer-based processing. Normally parts have reduced strength in the processing direction. Orientation therefore should be adjusted to avoid processing the part in the critical load direction.

Residual stresses: Residual stresses not only affect part quality due to warp and distortion, they could also lead to process failure. While processing, peeling off of single layers (curling) or tearing off both the part from support structures and the support structures from the substrate can result from residual stresses. As a consequence, deposition of a new powder layer is impossible and the process fails and has to be stopped. By variation of the scanning regime (e.g., stripes or checkerboard), it is quite possible to reduce thermal gradients locally. But this method is not always applicable for complex geometries. To reduce high thermal gradients it is necessary to consider heat conduction for the entire part. In addition, intricate and thin areas of the part cannot be produced properly with stripes or checkerboard patterns. Minimization of residual stresses and high thermal gradients is possible with thermal process control or local adjustment of process parameters based on thermal simulation of the AM process. However, this is a very elaborate procedure, which has to be done individually for each part. In addition, only very simple simulation approaches are available, which are only useful for very simple geometries. An application for arbitrary and/or complex part geometries is not possible today. Also, most of the commercial AM systems do not allow for a local in-situ process parameter adjustment. On the other hand, optimization of part orientation could well address the issue of residual stresses for complex parts.

Build time: The cost of an AM production mainly depends on part size and not necessarily on the part complexity. It is worth noting that the build time due to the layering principle is essentially determined by the height of the part, which corresponds to part size and its orientation. Hence, orientation could lead to reducing production costs and hence cost is a major factor while optimizing orientation of parts.

In summary, in AM part orientation has a crucial effect on both part quality and process quality. Even though the effect of part orientation is well known, there is no automatic solution available in the market to orient parts for fabrication in AM processes. The adverse effects enumerated immediately above can be significantly mitigated by optimal part orientation. The selection of optimal orientation however is not trivial. This is partly due to the fact that orientation affects several aspects of the part and process quality and these effects create optimization trends that are not necessarily in the same direction. This difficulty significantly increases with part complexity. As a result, the common practice is that an operator decides about part orientation only based on personal experience and knowledge. So far, there are no guidelines or software tools, which methodologically assist the operator in this decision. Especially in production of complex parts like the tool holders with internal structures, which is the scope of this project, this decision is challenging. Our technology provides a holistic computer-aided optimization of part orientation to assist the operator in AM metal process preparation. This approach will be implemented at the interface between CAD modeling and the AM-specific steps of data preparation (support generation, slicing, hatching). Therefore, this approach is not limited to a particular AM system. This approach can clearly close the existing gap and will represent an important step to increase effectiveness and productivity of AM processes for metals.

Figure 48:
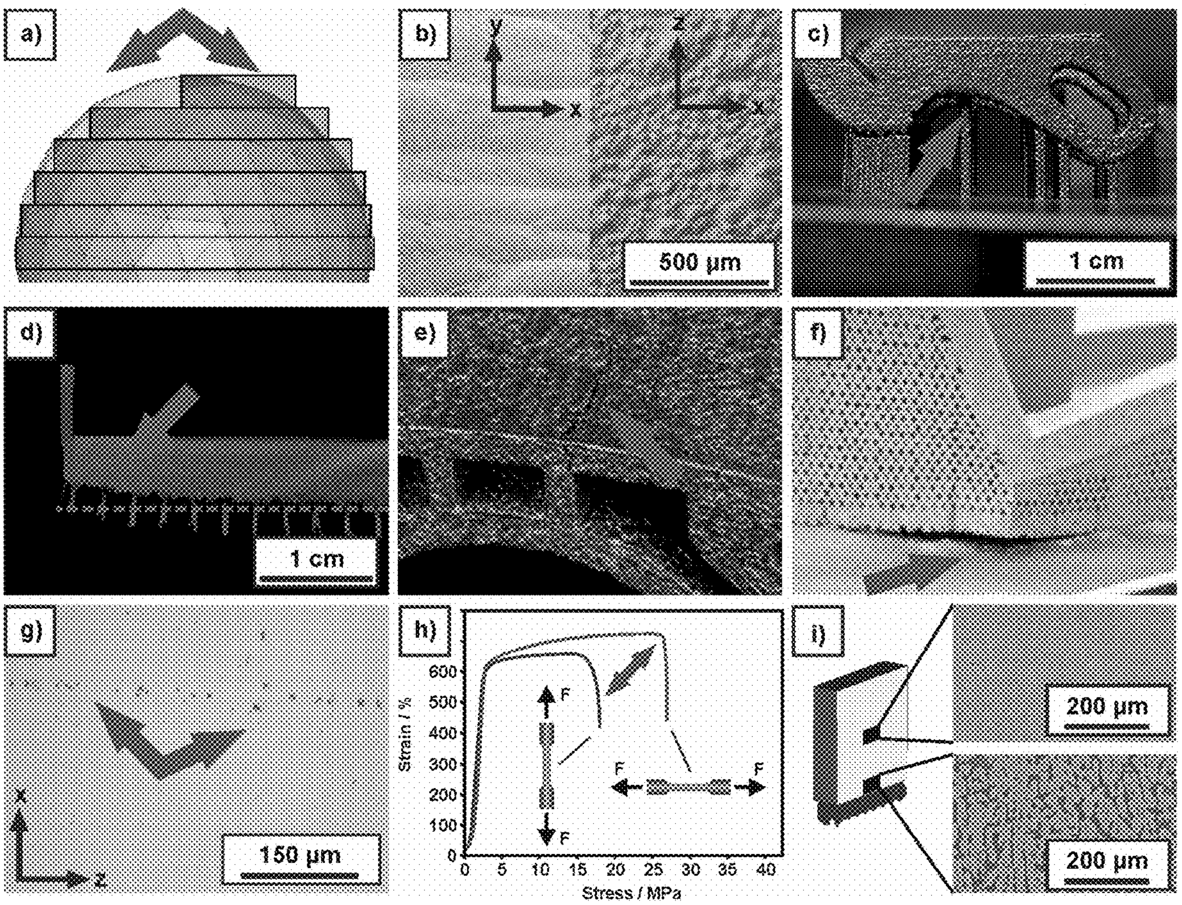
FIG. 48: Orientation related effects and process faults in SLM: Schematic showing staircase effect (a), SEM micrographs of AM NiTi showing different surface topologies depending on face orientation (b), AM Ti6Al4V part showing deviation from dimensional accuracy and rough surface on declined face (c), cross section of a micro-CT scan showing significant distortion of an AM 316L part due to residual stresses (d), crack formation in an AM part due to residual stresses (Zäh and Branner 2010) (e), residual stresses in AM part tearing off support from base plate (Zäh and Branner 2010) (f), micrograph showing periodic pore formation in an AM 316L part (g), mechanical anisotropy in AM 316L tensile testing (Meier and Haberland 2008) (h), SEM micrographs showing different microstructures in same AM NiTi part due to different rates of solidification (Meier et al. 2009) (i).
Figure 49:
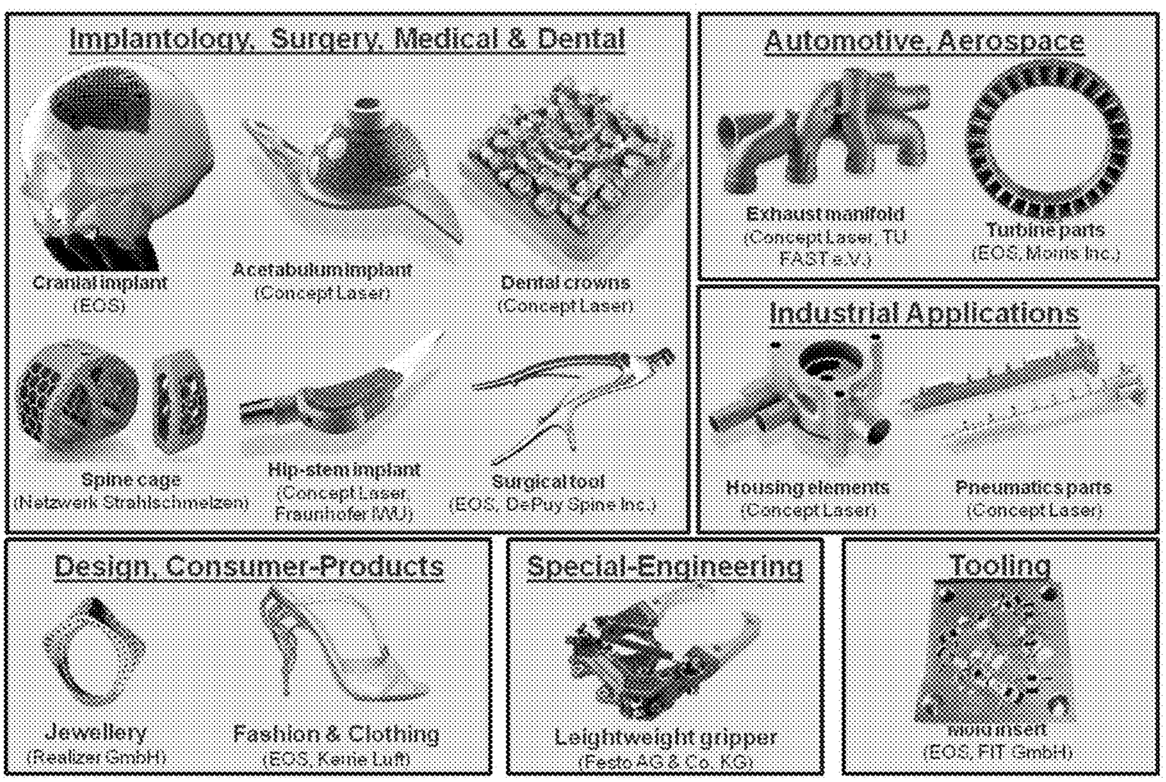
FIG. 49 illustrates AM metal parts and markets.

Our technology will significantly improve the AM process of metals and to open up new perspectives by developing and using innovative metal parts produced by AM because today, a substantial analysis and decision of an optimized part orientation for AM is not available. Today, AM is not yet ready to produce any complex metal part economically and effectively. The reason is that for complex metal parts, currently no AM technology offers a first-time-right production package. Instead, trial-and-error is a necessary step to process AM metal parts. However, the market and the number of applications for AM metal increase significantly year by year. FIG. 48 shows several examples for such AM metal parts and several markets where AM metal parts are applied.

As described before, there is a strong need to optimize part orientation for AM of metals. There are multiple criteria for this optimized part orientation and quite often they are contrary. Without computer tools, considering all these criteria for complex part geometries is nearly impossible. There have been efforts at developing such computer tools since the 1990's. Today, a variety of research publications is available that deal with computational optimization of part orientation as an important element in the process preparation. The existing computational tools however have limitations as described below.

- No approach is commercially available. All of these solutions are exclusive and only available to the respective research groups. In addition, most of these approaches are only in a state of mathematical theory.
- To date, none of these approaches is applied to complex geometries and inner structures. Some of the approaches are only applicable to specific types of faces (e.g., convex faces). It is obvious that these approaches are very limited and cannot accommodate the "freedom of design" which should be provided by AM. Complex geometries with internal structures are even more challenging to manufacture and therefore of particular interest for a solution to optimize parts' orientation.
- No approach offers the possibility of interaction with the operator. The operator simply has to accept the suggested orientation although it may not be the optimized orientation for the entire part. Therefore, none of these approaches is able to take into account particular local requirements.
- Most of these approaches focus on Stereolithography, Fused Deposition Modeling or Selective Laser Sintering of polymers. Due to substantially different techniques, materials, influences (e.g., thermal gradients are significantly higher in AM of metals) these approaches are not applicable to Selective Laser Melting of metals.
- Most of these approaches focus exclusively on single criteria (e.g., shortening of build time or minimizing support areas). There is no holistic approach, which considers the high number of influences and requirements mentioned before.

It is clear that there is a strong need for an optimization approach to orient complex metal parts for AM fabrication. Our technology is a multi-objective approach to optimize part orientation in respect to the following criteria (design variables, constrains and targets) and loading conditions:

- Accuracy: The dimensional accuracy relies on several parameters, which is considered in our technology to achieve the highest dimensional accuracy. Deviations from the desired geometry are firstly caused by the difference between the triangulated *.STL model and the sliced model due to the staircase effect which increasingly appears at curved and inclined surfaces. Our technology minimizes the volume difference of both models by adjusting the orientation. In addition, inhomogeneous shrinkage will be considered as well as face orientations, which are typically susceptible to deviation from the desired geometry. Therefore, the model will be orientated to minimize overhangs, faces with a flat inclination angle and downward concave surfaces to avoid inaccuracy by local sagging.
- Surface quality: In regard to surface morphology and quality our technology takes into account the effect of orientation on different morphologies according to the face orientation (vertical walls, horizontal planes and inclined faces), staircase related effects (see dimensional accuracy) as well as areas which have to be supported during processing as these surfaces are usually characterized by inhomogeneous and poor surface qualities.
- Support structures: In terms of support structures, our technology minimizes the areas that have to be supported. This leads to minimizing the need for subsequent finishing. In addition, our technology considers the accessibility and functionality of these areas to significantly reduce or even completely avoid support structures that are attached to faces where they cannot be removed after processing (e.g., internal faces). Our technology therefore orientates the model to minimize or even avoid support structures where they will lead to a decrease in the quality of functional and/or optical surfaces.

Anisotropy: Our technology takes into account that the mechanical strength is typically better along the layers than perpendicular to layers (building direction). Our technology optimizes the orientation according to the intended use of the part and the load conditions especially for intricate elements (e.g., thin walls) where only a few hatches fill the cross sections and systematic pore agglomerations might be a high risk for failure.

Heat management: Heat management is one of the most important criteria for success of an AM process. Inhomogeneous temperature distribution, high temperature gradients and heat build-ups result in thermal stresses, which can lead to distortion and warp. These not only degrade the part quality (e.g., dimensional accuracy, mechanical properties), they also can cause process failures (curling, tearing off the part from substrate or supports). Our technology pays special attention to the heat management. Without special simulation software and extensive computing an exact evaluation is impossible. However, there are some knowledge-based guidelines that will be implemented. As a rule, large layer cross sections, large disparities or jumps in cross section dimensions of successive layers as well as layer cross sections which are built onto powder (and supports) are critical areas for heat build-ups and can result in warp and curling. Therefore, our technology minimizes or even avoids these geometrical features by shifting the inclination angle to an optimized part orientation.

Economy: Our technology addresses is related to economic aspects. For efficient AM processing the number of layers has to be reduced by the choice of an appropriate part orientation.

Figure 50:
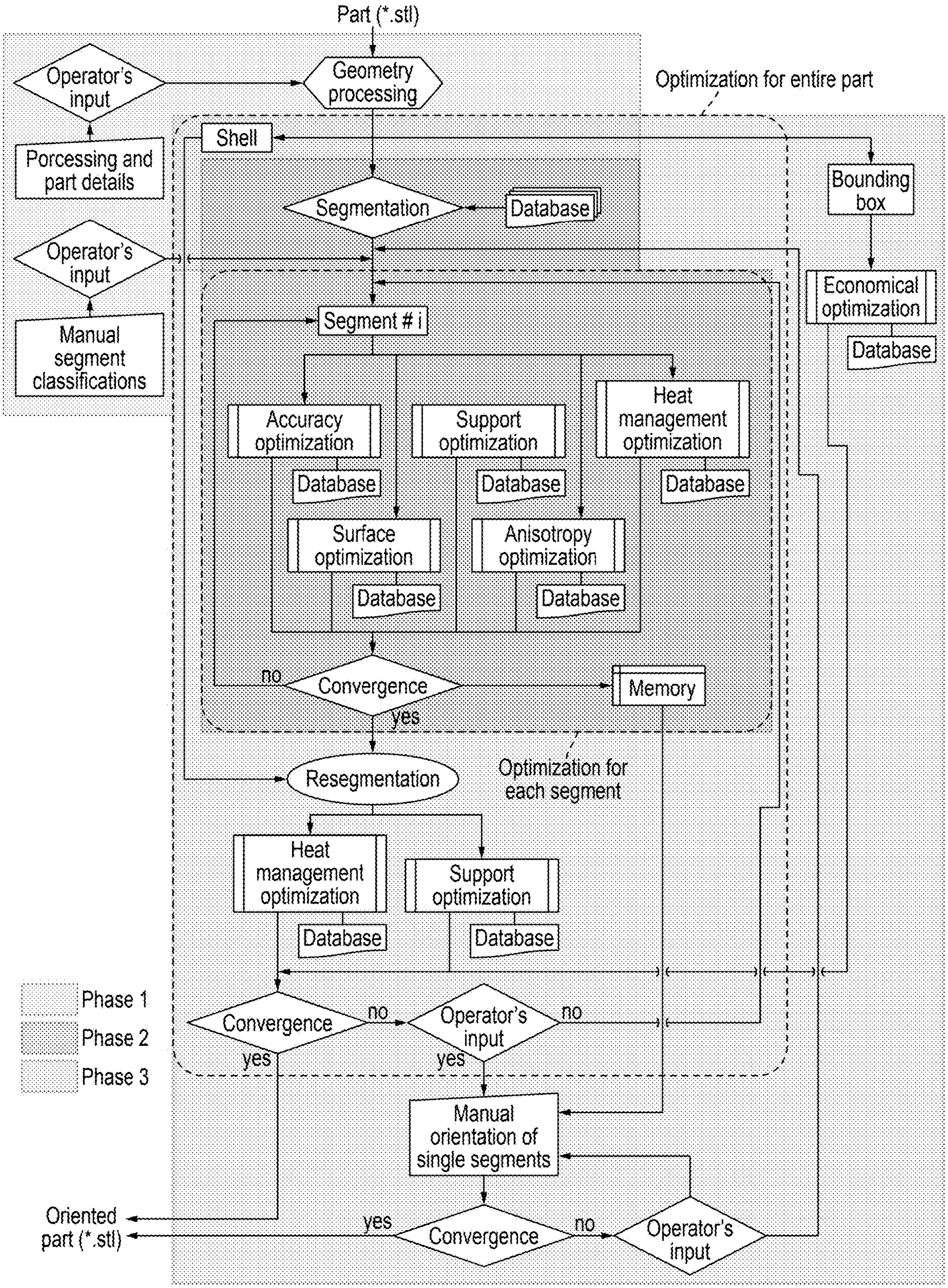
FIG. 50 is a flowchart showing the targeted structure of an optimization approach to part orientation for AM.

Our technology considers simultaneously these six usually conflicting criteria in a multi-objective optimization approach using desired algorithms at different stages of the optimization. Our technology therefore undergoes three phases. After definition of the general geometry of the product, requirements and boundary conditions such as load, fit, tolerances (phase 1), our technology reduces the part complexity by decomposition of the entire part because even for our holistic approach it is almost impossible to meet all criteria for finding an optimized part orientation among infinite possible orientations with increasing part complexity. In addition to the decomposition, in phase 2 each segment orientation is optimized individually and finally, in phase 3, our technology recomposes the part. The three phases are described below and FIG. 50 schematically shows the targeted structure of our multi-objective optimization technology:

1. Boundary Condition Definition: This phase takes the entire geometry of the product and allows the operator to add information about processing (e.g. layer thickness), material, constraints, requirements and objectives (e.g., load conditions in use). The purpose of this phase is to have all relevant information and data before moving onto the detailed design.
2. Detailed Design Optimization: This phase of the program will dive into the detailed design of the product using AM process. The product shape, which contains the design of the desired part, will be divided into simple geometric sub-models without losing important design features and the position of the sub-models in the entire part. Decomposition or segmentation has two advantages in our technology for part orientation: 1) every feature of the part will be considered in selecting the orientation, and 2) Reduction of complexity easily allows the operator to interact with the optimization approach if it is required. Therefore, phase 2 of our technology starts with segmentation of the entire complex geometry in simple reference geometries. Each segment will then be analyzed according to the design variables, design and performance target criteria explained before (accuracy, surface quality, support connection, anisotropy and heat management). The segmentation will allow the optimization to search for an optimum solution much faster, will consider more details and will let the user define more design variables because the finite element models of each segment are much smaller than the total geometry. Our technology chooses an appropriate orientation for each segment by iteratively changing its spatial orientation. For each segment our algorithms consider orientation-dependent characteristics and properties stored in a property database. To create these database entries we will produce simple reference geometries in different sizes and orientations and perform analyses in terms of accuracy, surface quality, structural anisotropy (mechanical testing) and economical aspects. The result of this phase will be a system of segments with optimal orientations.
3. Final Design Validation: In this step all segments will be recombined with respect to their individually optimized orientation. Our technology then performs a second optimization loop, which incorporates the individual segment orientations and optimizes the orientation for the whole assembly. It is extremely unlikely that all individual optimized orientations will lead directly to a single solution for the entire part. Therefore, the optimization selects the best fitness function. Also, individually optimized orientations cannot account for economic aspects for processing the entire part. More importantly, this second optimization considers the heat management of the entire part because heat conduction in the entire geometry is different from that of each segment. While the first optimization aims to orientate segments in terms of minimizing large layer cross sections, the second optimization then considers large jumps and disparities in cross sections as well as large layer cross sections after recombining all segments. In addition, support structures might require a different design and arrangement when considering the entire part (e.g., accessibility, internal faces). Therefore, the second optimization will also consider this criterion.

The advantages that our invention offers include:

Use of a holistic design approach that considers economic aspects (build time, finishing effort) and optimizes the component quality and process reliability.

Integration of a database that is based on comprehensive experiments to account for precise optimization.

Consideration of complex geometries and internal features by segmentation without neglecting the entire structure complexity. Our technology optimizes locally but also identifies typical areas of heat build-up and thermal gradients and incorporates this into the optimization.

The possibility of manual intervention. This is because as in complex parts an ideal orientation, which accounts for all demands, usually does not exist. Our technology is a multi-objective optimization, which suggests an optimized orientation. The user can accept directly or, in the case of local preferences determine an alternative according to those preferences. First, the operator will submit input variables before starting the optimization process. These input variables include processing details (e.g., layer thickness, AM system specific characteristics . . . ) as well as general part details (purpose, type and directions of load . . . ). This information will be considered once for each segment and in once for the entire part. After segmentation but before starting the first optimization the operator then can determine special requirements for individual segments. Here, because of the segmentation the operator has the opportunity to add priority to local features. He can rank the design variables. For example, certain areas can be characterized as functional areas with the highest quality standards. Finally, after having passed the optimizations (each segment and the entire part) there will be a suggestion of an optimized part orientation. It is likely that at a high part complexity not all of the criteria are met for each segment. If the suggested solution orientation is not acceptable for a specific segment the operator has the ability of intervention. Therefore, our technology uses a memory in the process which the operator can use to change the orientation of the entire part based on a single segment which he thinks is of more importance. In both optimization loops the operator has control over the suggested design orientation. The operator can also suggest a design orientation as an input design for consideration in the next loop of optimization.

A versatile multi-objective optimization methodology and facilitates AM processes for metals.

Our technology provides the following value to AM metal processing:

Increasing process reliability by reducing orientation related failures

Saving cost by reducing waste of material (material for trial-and-error, failure of parts)

Saving cost by reducing production time

Saving costs by reducing efforts for finishing

Improving part quality (strength, surface, accuracy)

Various features and advantages of the invention are set forth in the following claims.

What is claimed is:

1. A method of fabricating a patient-specific implant comprising the steps of:

acquiring, using an electronic processor, a 3D CT scan of an anatomic structure of a patient;

preparing, using the electronic processor, a cross-sectional model of masticatory muscles of the patient based on the 3D CT scan;

determining, using the electronic processor, a stress and strain profile for the anatomic structure, wherein the anatomic structure is positioned within a portion of at least one organ of a patient, and wherein the anatomic structure is a mandible bone;

wherein determining the stress and stress profile for the anatomic structure comprises determining, using the electronic processor, forces of each of the masticatory muscles using a predetermined bite force;

designing, using the electronic processor, a patient-specific implant for a segment of the mandible bone, wherein a stress and strain profile for the patient-specific implant matches the stress and strain profile and a 3D geometry for the mandible bone from a normal anatomy; and fabricating the patient-specific implant using additive manufacturing.

2. The method of claim 1, wherein the patient-specific implant further comprises autologous, allogeneic or alloplastic tissue.

* * * * *